(12) United States Patent
Frechet et al.

(10) Patent No.: US 7,097,856 B2
(45) Date of Patent: Aug. 29, 2006

(54) DENDRIMERIC SUPPORT OR CARRIER MACROMOLECULE

(75) Inventors: Jean J. Frechet, Oakland, CA (US); Rolf H. Ihre, Stockholm (SE)

(73) Assignee: The Regents of the University of California, Oakland, CA (US)

( * ) Notice: Subject to any disclaimer, the term of this patent is extended or adjusted under 35 U.S.C. 154(b) by 403 days.

(21) Appl. No.: 09/963,858

(22) Filed: Sep. 25, 2001

(65) Prior Publication Data

US 2002/0123609 A1 Sep. 5, 2002

Related U.S. Application Data

(60) Provisional application No. 60/236,561, filed on Sep. 29, 2000.

(51) Int. Cl.
*A61K 9/34* (2006.01)
*A61K 47/06* (2006.01)

(52) U.S. Cl. ............. 424/486; 514/772; 549/370; 528/272; 536/23.1

(58) Field of Classification Search ............. 424/486; 514/772; 549/370; 528/272; 536/23.1
See application file for complete search history.

(56) References Cited

U.S. PATENT DOCUMENTS 5,418,301 A 5/1995 Hult et al.
5,714,166 A * 2/1998 Tomalia et al. ............. 424/486
6,114,458 A 9/2000 Hawker et al.

FOREIGN PATENT DOCUMENTS

WO WO 97/45474 A1 12/1997
WO WO 99/00439 A1 1/1999

OTHER PUBLICATIONS

Magnusson et al. Macromolecules 2000, 33, 3099-3104.*
Annby, U. et al., "Benzylidene Protected Bis-MPA, A Convenient Dendrimer Building Block," *Tetrahedron Letters*, Elsevier Science Publishers, Amsterdam, NL, 39:3217-3220 (1998).
Trollsas, M. et al., "Hyperbranched Poly(epsilon-caprolactone)s," *Macromolecules*, 31:3439-3445 (1998).
Trollsas, M. et al., "Highly Functional Branched and Dendri-Graft Aliphatic Polyesters through Ring Opening Polymerization," *Macromolecules*, 31:2756-2763 (1998).
Trollsas, M. et al., "Versatile and Controlled Synthesis of Star and Branched Macromolecules by Dendrimeric Initiation," *Macromolecules*, 30:8508-8511 (1997).

* cited by examiner

Primary Examiner—Jezia Riley
(74) Attorney, Agent, or Firm—Morgan, Lewis & Bockius LLP

(57) ABSTRACT

The present invention provides a family of dendrimers that are useful as supports, vectors, carriers or delivery vehicles for a variety of compounds in biomedical and technological applications. In particular, the macromolecules may be used for the delivery of drugs, genetic material, imaging components or other functional molecule to which they can be conjugated. An additional feature of the macromolecules is their ability to be targeted for certain organs, tumors, or types of tissues.

33 Claims, 9 Drawing Sheets

DENDRIMERIC SUPPORT OR CARRIER MACROMOLECULE

CROSS-REFERENCE TO RELATED APPLICATIONS

This application claims priority to U.S. Provisional Application Ser. No. 60/236,561, filed on Sep. 29, 2000, the disclosure of which is incorporated herein by reference in its entirety for all purposes.

BACKGROUND OF THE INVENTION

Dendrimers are polymers of spherical or other three-dimensional shapes that have precisely defined compositions and that possess a precisely defined molecular weight. Dendrimers can be synthesized as water-soluble macromolecules through appropriate selection of internal and external moieties. See, U.S. Pat. Nos. 4,507,466 and 4,568,737, incorporated by reference herein. The first well-defined, symmetrical, dendrimer family were the polyamidoamine (PAMAM) dendrimers, which are manufactured by the Dow Chemical Company. Since the synthesis and characterization of the first dendrimers, a large array of dendrimers of diverse sizes and compositions has been prepared. See, for example, Newkome, G R, Moorefield, C N and Voegtle, F. "Dendritic Molecules" VCH, Weinheim, 1996; and Liu M. and Frechet J. M. J., *Pharm. Sci. Tech. Today* 2(11):393 (1999).

Dendritic macromolecules are characterized by a highly branched, layered structure with a multitude of chain ends. Dendrimers are particularly well defined with a very regular and almost size monodisperse structure, while hyperbranched polymers are less well defined and have a broader polydispersity. Dendritic macromolecules are usually constructed from $AB_x$ monomers. Hyperbranched polymers are generally obtained via a polymerization reaction that generally takes place in a single series of propagation steps. Dendrimers are generally obtained by multistep iterative syntheses using either a divergent (Tomalia et al, U.S. Pat. Nos. 4,435,548; 4,507,466; 4,558,120; 4,568,737; 5,338,532) or a convergent growth approach (Hawker et al., U.S. Pat. No. 5,041,516).

Dendrimers have been conjugated with various pharmaceutical materials as well as with various targeting molecules that may function to direct the conjugates to selected body locations for diagnostic or therapeutic applications. See, for example, WO 8801178, incorporated by reference herein, see also a review by Liu M. and Frechet J. M. J., *Pharm. Sci. Tech. Today* 2(11):393 (1999) Dendrimers have been used to covalently couple synthetic porphyrins (e.g., hemes, chlorophyll) to antibody molecules as a means for increasing the specific activity of radiolabeled antibodies for tumor therapy and diagnosis. Roberts et al., *Bioconjug. Chemistry* 1:305–308 (1990); Tomalia et al., U.S. Pat. No. 5,714,166.

Rehnberg et al. (WO 99/00439) describe a method of preparing polyester dendrimers from an acetal protected 1,3-diol carboxylic acid monomer. The disclosed method relies on a carbodiimide mediated coupling of the monomer to a hydroxyl-containing initiator molecule. Ester formation via carbodiimide coupling of the monomer to the initiator molecule produces N-acyl urea-containing side products as well as the desired dendrimer. In addition the reaction with dicyclohexyl carbodiimide produces a very large amount of dicyclohexyl urea which is very difficult to remove from the desired dendrimer product. The formation of the side products is particularly problematic for the multistep synthesis of a polymeric species such as a dendrimer; the N-acyl urea side product formed in a first step reacts in a subsequent step adding a new generation to both the desired dendrimer core and to the side product. The similarity in properties between the side product and the desired dendrimer makes separation of the species difficult, and economically unfeasible for the large-scale preparation of dendrimers. As dendrimers are under intense evaluation as delivery vehicles for therapeutic and diagnostic agents, the presence of the N-acyl urea side products as well as any dicyclohexylurea impurity is seen as a serious impediment to understanding the pharmacokinetics and pharmacodynamics of these important agents, and will surely hamper their progress towards regulatory approval.

In view of the above, a method of preparing polyester dendrimers and related dendritic polymers free of urea side products, and conjugates of these dendrimers with diagnostic, therapeutic and analytic agents would represent a significant advance in the development of dendrimer-based pharmaceutical and analytical agents. Surprisingly, the present invention provides such a method and compounds produced by the method.

SUMMARY OF THE INVENTION

Applicants have discovered a method of preparing dendrimers, which utilizes an anhydride, preferably derived from a protected 1,3-diol carboxylic acid monomer. The method is appropriate for the preparation of a wide array of dendrimers and dendrimer conjugates, which are substantially free of coupling reagent derived side products. In contrast to prior methods in which the carboxylic acid moiety undergoes carbodiimide activation in situ, in the present invention, the anhydride is formed and purified prior to its use to elaborate the dendrimer core. Surprisingly, the dendrimers prepared by the method of the invention are of such purity that they are generally isolated as solids.

The method of the invention is practiced with essentially any anhydride of a carboxylic acid without limitation. Applicants have discovered that the use of an isolated, purified anhydride as the reactive building block in dendrimer formation, in contrast to previous methods, provides products having a surprisingly high level of structural homogeneity. Moreover, the method of the present invention provides dendrimers that are of a high degree of purity, being substantially free of reaction side products, such as those derived from carboxyl activating reagents (e.g., dicyclohexylcarbodiimide).

In presently preferred embodiments, the invention provides polyester and polyamide dendrimers, which are highly pure. Exemplary dendrimers of the invention are based upon on diverse polymeric or oligomeric dendrimer core molecules having pendant hydroxyl groups. Analogous dendrimers based upon core molecules with pendent reactive amine and sulfhydryl moieties are also provided. Representative core molecules include nucleic acids; poly(alkylene oxides), e.g., star and linear; polysaccharides and synthetic polymers. The invention also provides dendrimers in which the core is a fluorophore, chromophore, therapeutic agent, diagnostic agent or the like. The dendrimers of the invention are useful carriers for diverse agents, including analytical, therapeutic and diagnostic agents. Also provided is an intermediate anhydride, the use of which in the methods of the invention provides dendrimers of greater purity than are available through the use of other intermediates.

The dendrimers of the invention are particularly useful in rendering water-soluble normally insoluble drugs or other agents. Moreover, the dendrimers of the invention have a low level of toxicity. The dendrimers are able to release drugs in cancer cells and certain of the dendrimers, e.g., the PEO poly(ethylene oxide) (PEO)-based dendrimers, are able to penetrate cells. Thus, the invention also provides a biological compartment defined by a membrane or particle in which a dendrimer of the invention is encapsulated. Exemplary biological compartments include cells and organelles.

The dendrimers of the invention can be formulated for a variety of modes of administration, e.g., intravenous and oral. Also provided are conjugates of the dendrimers with an exemplary anticancer drug, doxorubicin.

An exemplary fourth generation hydroxyl functional aliphatic ester dendrimer 10 based on bis-hydroxymethyl propanoic acid is highly soluble in water (200 mg/ml). No adverse effects on cell metabolism are observed at concentrations of this dendrimer as high as 40 mg/mL. Standard in vivo experiments on mice determined that the $LD_{50}$ dose of this dendrimer is well above 1 g/kg body mass, confirming the lack of cytotoxicity and the biocompatibility of this dendritic aliphatic ester compound. Furthermore, standard biodistribution studies in mice showed that the aliphatic ester dendrimers of the invention are excreted from the body, via the kidneys, and not accumulated in the body.

The carriers of the invention are prepared by an unexpectedly efficient process for divergent growth of a dendrimer through anhydride acylation (e.g., esterification, amidation) of the pendent groups on the core and the previous generation of the dendrimer. Also provided are acetal and ketal protected diol-containing anhydride monomers that are useful in preparing the dendrimers of the invention.

Other objects and advantages of the present invention will be apparent from the detailed description and examples that follow.

DETAILED DESCRIPTION OF THE INVENTION AND THE PREFERRED EMBODIMENTS

Definitions

Figure 1A:
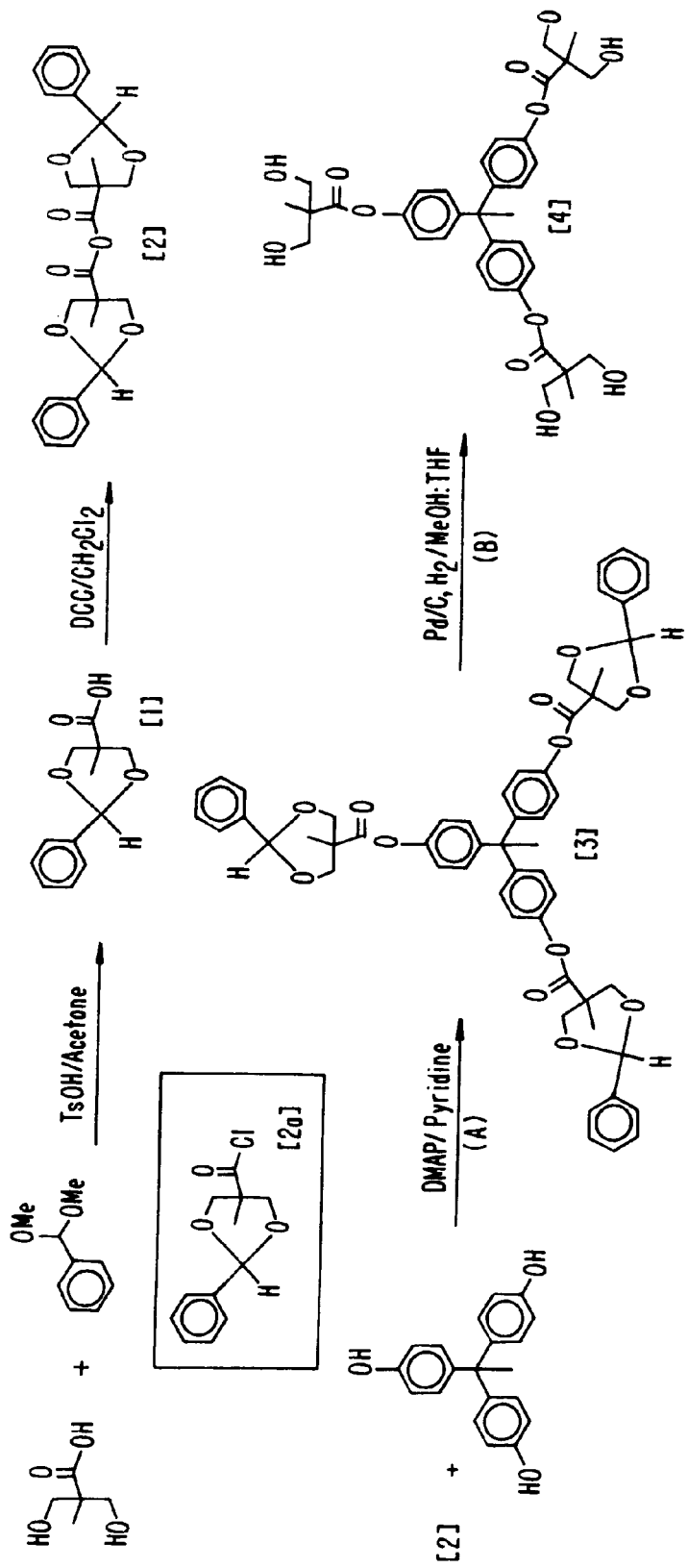
FIG. 1 is an exemplary reaction scheme for preparing a fourth generation dendrimer of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references, see, generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

As used herein, the term "dendrimer," refers to regular dendrimers, as this term is generally used in the art, and also to related dendritic structures such as dendronized polymers, dendritic stars, dendritic linear hybrids, and the like.

The terms "core molecule" and "core moiety" are used interchangeably to refer to the point of origin of the dendrimers of the invention. Useful cores include pendent "active groups" (e.g., amine, hydroxyl, sulfhydryl) within their structure. The active groups are acylated by an anhydride of the invention, effectively adding a generation onto the dendrimer growing out of the core.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid but, which functions in a manner similar to a naturally occurring amino acid.

"Therapeutic agent" or "drug" refers to any chemical or biological material, compound, or composition capable of inducing a desired therapeutic effect when properly administered to a patient. Some drugs are sold in an inactive form or "pro-drug" that is converted in vivo into a metabolite with pharmaceutical activity. For purposes of the present invention, the terms "therapeutic agent" and "drug" encompass both the inactive drug and the active metabolite.

As used herein, the term "leaving group" refers to a portion of a substrate that is cleaved from the substrate in a reaction.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule.

Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$ NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, (C$_1$–C$_8$)alkyl and heteroalkyl, unsubstituted aryl and heteroaryl, (unsubstituted aryl)-(C$_1$–C$_4$)alkyl, and (un-substituted aryl)oxy-(C$_1$–C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$–C$_6$)alkyl.

As used herein, the term "heteroatom" is meant to include oxygen (O), nitrogen (N), sulfur (S) and silicon (Si).

"Substantially free of coupling reagent derived side product," as used herein refers to products having levels of coupling reagent derived side products that are from about 5% to about 0.01%, more preferably from about 1% to about 0.1% of the dendrimer composition. An exemplary coupling reagent is dicyclohexylcarbodiimide. Exemplary coupling reagent derived side products include, but are not limited to dicyclohexyl urea and N-acyl urea. The presence of such impurities are readily ascertained by the use of elemental analysis and nuclear magnetic resonance spectroscopy for low resolution analyses, and mass spectrometry, liquid chromatography, and combinations thereof including liquid-chromatography-mass spectrometry for high resolution analyses.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical meth ods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may be in aggregated or micellar forms, meaning that instead of discrete molecules, assemblies thereof may be used that "disassemble" in vivo, the aggregation may be done purposely or by a self-assembly process.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

INTRODUCTION

The present invention provides a method of preparing polyester dendrimers, which leads to highly pure dendrimers that are substantially free of urea-containing impurities. The dendrimers of the invention are of such purity that they are easily isolated as stable solids.

Applicants have recognized that a preformed, purified anhydride, which is substantially free of coupling reagent derived impurities is a versatile intermediate that provides exceptional yields of pure polyester dendrimers. As such, the present invention represents a significant advance over prior methods of preparing polyester dendrimers.

Prior to the present invention, art-recognized methods of preparing polyester dendrimers relied on the in situ activation of the 1,3-diol carboxylic acid building block. For example, the carboxylic acid was activated using dicyclohexyl carbodiimide. Unrecognized by the prior methods, the use of in situ activation, particularly with a carbodiimide, in the dendrimer growth step is problematic. The use of a carbodiimide in the growth step leads to the formation of dicyclohexyl-derived side products (e.g., dicyclohexyl urea, N-acyl urea), which participate in subsequent dendrimer growth steps, resulting in a complex mixture of urea-free and urea-containing dendrimers, the separation of which is impractical or impossible. Prior methods failed to recognize that the urea side products were produced, and the difficulty inherent in separating the side products from the desired dendrimer. Thus, the art fails to suggest any method useful to either prevent the formation of the side products or to remove them from the desired dendrimer. An example of the propagation of the N-acyl urea-containing dendrimer side products in prior methods is set forth in Scheme 1.

Scheme 1

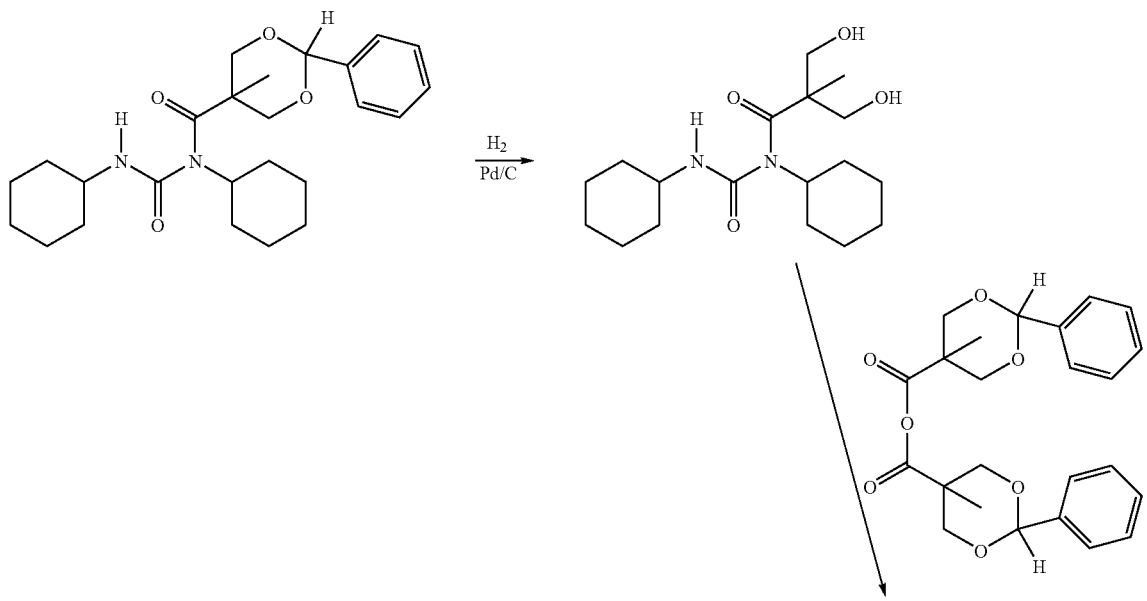

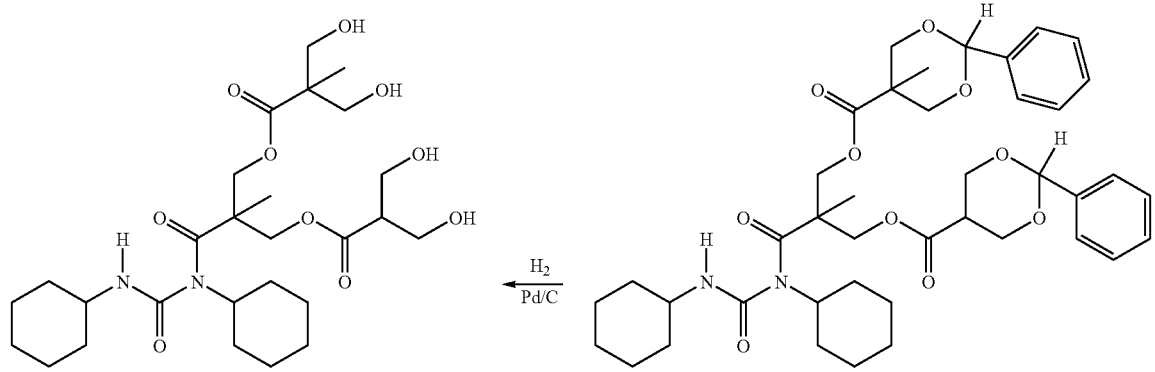

-continued

The dendrimers of the invention have unexpected combinations of properties not found in other polyester, polyamide or polyether dendrimers. In particular, the dendrimers prepared by the methods of the invention are surprisingly pure in view of the results achieved using prior methods. Moreover, the dendrimers exhibit high water solubility, unexpectedly low toxicity towards cells, and they are eliminated from the body through normal pathways such as through the urine.

The properties of the present dendrimers are in contrast to the well-known PAMAM poly(amidoamine) dendrimers or ASTRAMOL poly(propyleneimine) dendrimers that have significant toxicity, in part as a result of their easy transformation into ionically charged species. Unlike the amine- and imine-based dendrimers, the polyester and polyamide dendrimers of this invention remain uncharged across wide range of pH values. The neutrality of the present dendrimers is a property that is useful in the application of the dendrimers as carriers or vectors for therapeutic applications. The polyester dendrimers of this invention are also distinct from known polyether dendrimers that exhibit less favorable solubility profiles, cannot be degraded by hydrolysis, and have significantly higher toxicities.

Many drugs are inherently hydrophobic and hence have limited solubility or ability to be dispersed in an aqueous medium, which reduces their bioavailability and makes them difficult to formulate or administer reducing their usefulness. Similarly, a number of potentially useful bioactive molecules are not sufficiently stable, or have a too short half-life in biological media for successful treatment, which also limits their use. As a result of these and other problems of pharmacokinetics, bioavailability, specificity, etc., there is a need to develop molecules that can help in the transport or delivery of bioactive or functional substances. As an example, one of the more interesting areas of pharmaceutical research today is gene-therapy where a disease like such as cystic fibrosis may be treated by incorporating missing genes into the cell nucleus. However, it is generally difficult to actually deliver the gene into the cell nucleus without using viral vectors, which, in many cases, are connected with side effects, as a result the practical application of gene-therapy is hampered.

One object of the present invention is the preparation of well-defined, water soluble or water-dispersible, biocompatible macromolecular carriers that may be used for the transport or delivery of active substances including for example drugs, genetic material, proteins, imaging aids, etc. Other applications of the same materials include their use as vectors or carriers in Magnetic Resonance Imaging (MRI), in sensors, and in diagnostics. Furthermore, the macromolecular carrier may be designed to incorporate a specific function such as the complexation of an active substance or metal complex, the targeting of specific tissue or organs, the ability to form larger micellar entities for encapsulation, the ability to undergo a biodegradation or bioerosion process, or the ability to interact with an external stimulus such as a source of radiation. The materials of this invention are designed for one or more modes of delivery including for example intravenous and oral. Given its high capacity, the macromolecular entity may be utilized to deliver a high payload of therapeutic or functional agent to the desired target.

A feature of the dendrimers of the present invention is the multivalency that may be expressed in a multiplicity of functionalities capable of interaction, functional complexation or binding through covalent or non-covalent linkages with one or more functional entities (drug, genetic material, protein, imaging aid, targeting moiety, steric stabilizing moiety, sensing or diagnostics moiety, solubilizing moiety, etc.). One preferred implementation of the dendrimers makes use of a dendritic macromolecule with suitable chain-ends and core or focal point functionalities. The core or focal functionality of the dendritic macromolecule may itself be oligomeric or polymeric. The dendritic macromolecule may be bound to other moieties or ligands used to confer steric stabilization, solubility, specific targeting, protection from rapid degradation or other property used for therapeutic, imaging, sensing, or diagnostics application. In a particularly preferred embodiment, the dendritic macromolecule may be attached to one or more oligomeric or polymeric molecules such as oligo- or poly-ethylene oxide for modification of its solubility, biocompatibility, steric stabilization, increased therapeutic effect or bioavailability, ability to form micellar structures, or ability to interact favorably or penetrate cells.

THE COMPOSITIONS

The present invention provides intermediates, which are useful in preparing the dendrimers of the invention. In one aspect, the invention provides an isolated, purified, symmetrical anhydride of a protected 1,3-diol carboxylic acid. The anhydride is preferably an easily handled, stable solid. Unlike previous methods, the anhydride is prepared and purified prior to its use in the methods of the invention. Thus, the present invention provides an anhydride that is substantially free of contaminating side products.

An exemplary anhydride of the invention has the structure:

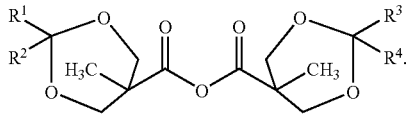

In which, $R^1$, $R^2$, $R^3$, and $R^4$ are members independently selected from substituted or unsubstituted alkyl, substituted or unsubstituted heteroalkyl and substituted or unsubstituted aryl. In a preferred embodiment, $R^1$, $R^2$, $R^3$, and $R^4$ are independently selected $C_1$–$C_6$ unsubstituted alkyl group, more preferably methyl, ethyl or propyl. In yet another exemplary embodiment, $R^1$ and $R^3$ are both H. In a preferred embodiment, the anhydride is a solid that is substantially free of coupling reagent side products.

In another aspect, the present invention provides an anhydride having the structure:

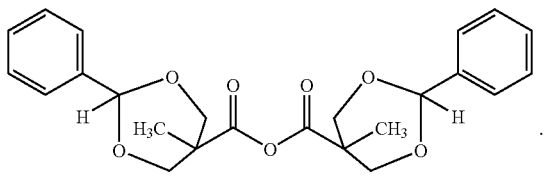

The anhydride is substantially free of coupling reagent side products, particularly dicyclohexyl urea and N-acyl urea products. The anhydride is preferably an easily handled, stable solid. In an exemplary embodiment, the solid anhydride is prepared by combining a protected 1,3-diol carboxylic acid with a coupling reagent, such as dicyclohexylcarbodiimide, in an organic solvent. After a selected reaction period, the desired anhydride is precipitated from the reaction mixture by adding the reaction mixture to a non-polar hydrocarbon solvent (e.g., hexane). The pure, solid anhydride is preferably isolated in a yield of greater than about 70%, more preferably greater than 80%, even more preferably greater than 85% and still more preferably greater than about 90%.

Figure 1B:
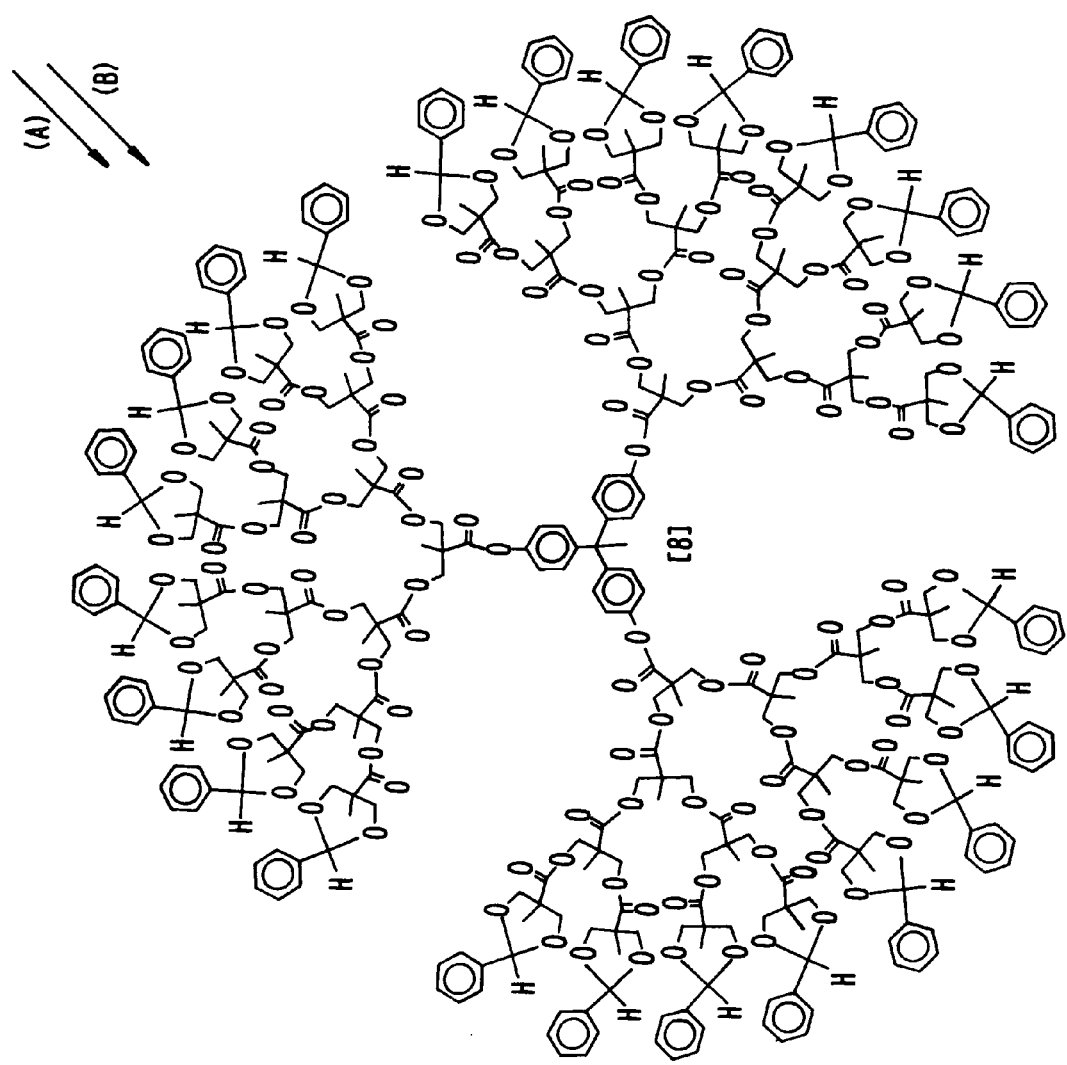
Figure 1C:
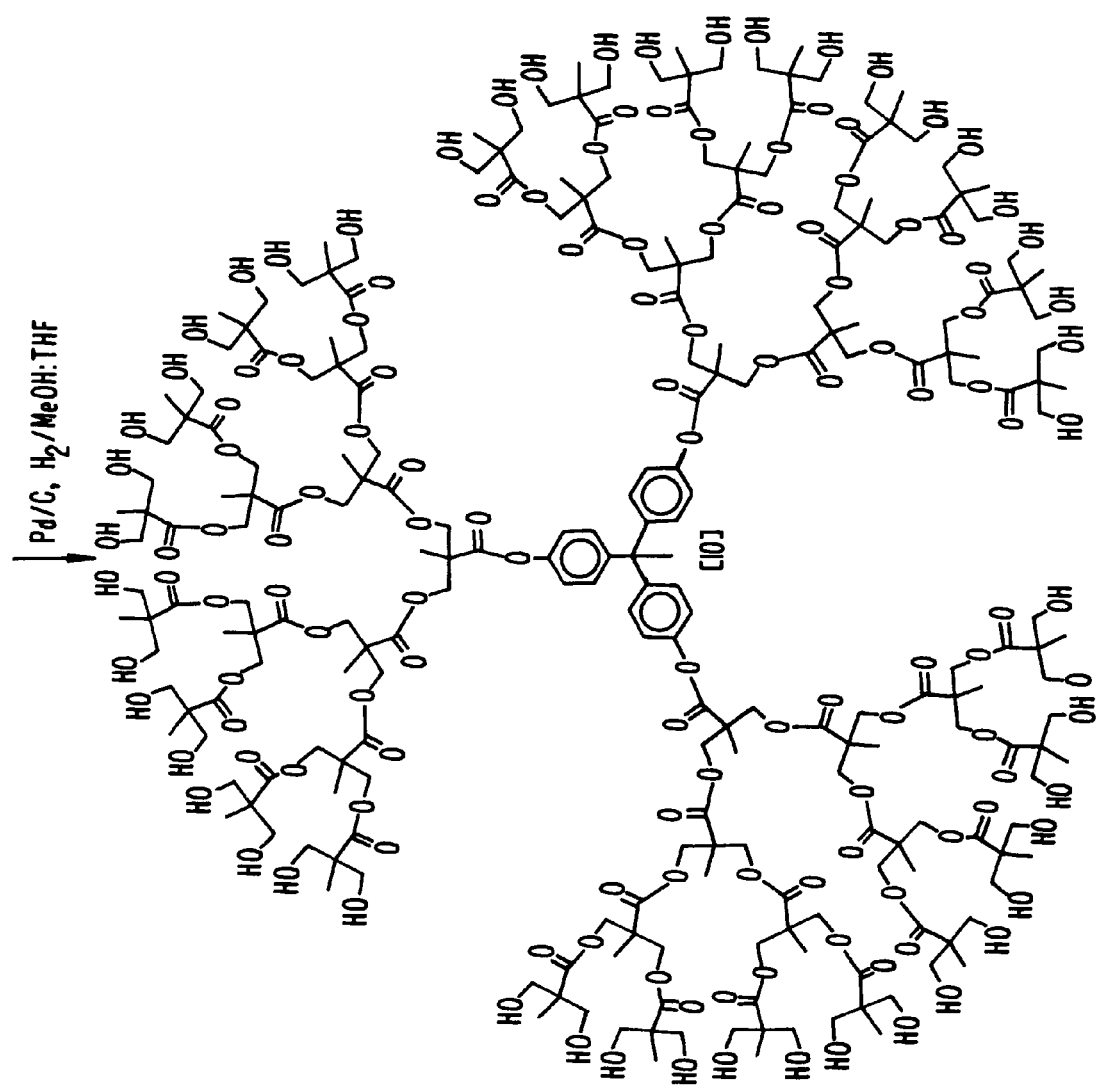

In an exemplary embodiment, with reference to FIG. 1, the 1,3-diol moiety of bis-MPA was protected to afford a benzylidene-protected molecule 1 by reaction of bis-MPA with benzaldehyde dimethyl acetal and a catalytic amount of p-toluenesulfonic acid (TsOH). Direct protection with aldehydes such as benzaldehyde or ketones such as acetone can also be achieved. Molecule 1 was transformed into the corresponding anhydride molecule 2 by reaction with N,N'-dicyclohexylcarbodiimide (DCC) acting as a condensation or dehydrating agent. Alternative condensation agents well know in the art can also be used. In this and in presently preferred embodiments, the pure anhydride is obtained as a crystalline solid. An alternative to molecule 2 is the corresponding acid chloride molecule 2a. The anhydride molecule 2 (or the corresponding acid chloride molecule 2a is used for reactions, e.g., esterification or amidation reactions with a core moiety or focal molecule containing a reactive functionality, e.g., a hydroxyl, and amino, or a thiol group.

The Dendrimers

The present invention also provides dendrimers that include one or more subunits having the structure:

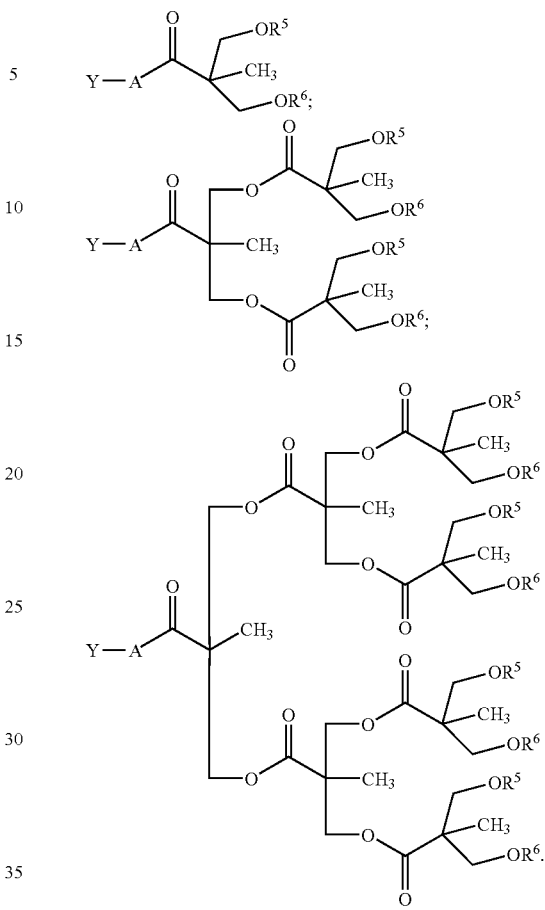

Those of skill in the art will appreciate that higher generation dendrimers incorporating one or more of the subunits presented above, are within the scope of the invention. The structures above are set forth to illustrate different embodiments of the invention, not to suggest any limitation on the scope of the structures provided by the invention.

In the formulae presented above, $R^5$ and $R^6$ represent members that are independently selected from the group consisting of H, diagnostic agents, therapeutic agents, analytical agents, and moieties comprising a reactive group. Alternatively $R^5$ and $R^6$ are components of a protecting group for a diol. When $R^5$ and $R^6$ form a diol protecting group, in general, $R^5$ and $R^6$ together with the oxygen atoms to which they are attached form a structure, which is a member selected from the group:

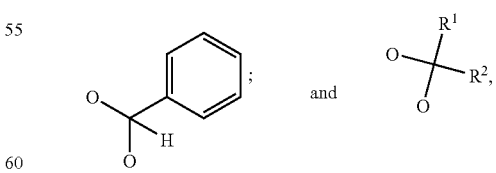

in which $R^1$, and $R^2$ are preferably substituted or unsubstituted alkyl, substituted or unsubstituted heteroalkyl and substituted or unsubstituted aryl In each of the dendrimer formulae displayed above, A is an active group residue, which is a member selected from NH, S and O. An active group that is a $C_1$–$C_6$ alkyl amine is also within the scope of the present invention.

Y is H, or it is a core moiety. The core moiety is an organic species having at least one active functional group, which serves as a locus of acylation by the anhydride. The core moiety can be strictly structural in nature, or it can have desirable characteristics of its own, separate from its structural function.

The core moiety can be derived from a macromolecule containing one or more reactive hydroxyl, amino, or thiol groups. The core can be derived from derivatives of poly (ethylene oxide), e.g., monoalkyl-poly(ethylene oxide) with one hydroxyl group, or a poly(ethylene oxide) with two hydroxyl groups (telechelic poly(ethylene oxide)), or a star poly(ethylene oxide) with three, four, or more hydroxyl groups. The core can also be derived from poly(ethylene oxide) molecules with amino or other reactive group chain ends instead of hydroxyl chain ends (see, for example, Shearwater Polymers Inc. catalog 2000).

In one embodiment, the core moiety is a polymer or oligomer that is "decorated" with multiple active functional groups that provide a locus of attachment for the dendrimeric subunits of the invention. In another embodiment, the core moiety is selected from bioactive groups and reporter groups. Exemplary bioactive groups include therapeutic agents. Reporter groups include diverse species, such as fluorophores, chromophores, diagnostic agents and the like.

Exemplary polymeric or oligomeric core moieties include, nucleic acids, linear poly(alkylene oxides), star poly(alkylene oxides), polysaccharides, poly(amino acids), and poly(hydroxy) species. Core moieties can also be based upon substituted or unsubstituted alkyl, substituted or unsubstituted heteroalkyl, substituted or unsubstituted aryl and substituted or unsubstituted heteroaryl groups.

Exemplary hydroxyl-containing polymers of use in practicing the present invention, including, but not limited to, single hydroxyl terminated poly(caprolactone) or telechelic or star hydroxy terminated poly(caprolactone); hydroxy terminated poly(lactic acid) or telechelic or star poly(lactic acid); hydroxy terminated poly(tetrahydrofuran) or telechelic or star poly(tetrahydrofuran); hydroxy-terminated or telechelic poly(salicylic acid); poly(hydroxystyrene); poly (hydroxycaprolactone); poly(hydroxymethylcaprolactone); poly(hydroxyethylcaprolactone) and other polycaprolactones containing hydroxy pendant groups; and polyamides or polypeptides containing tyrosine, serine, threonine, or hydroxyproline moieties.

Figure 4:
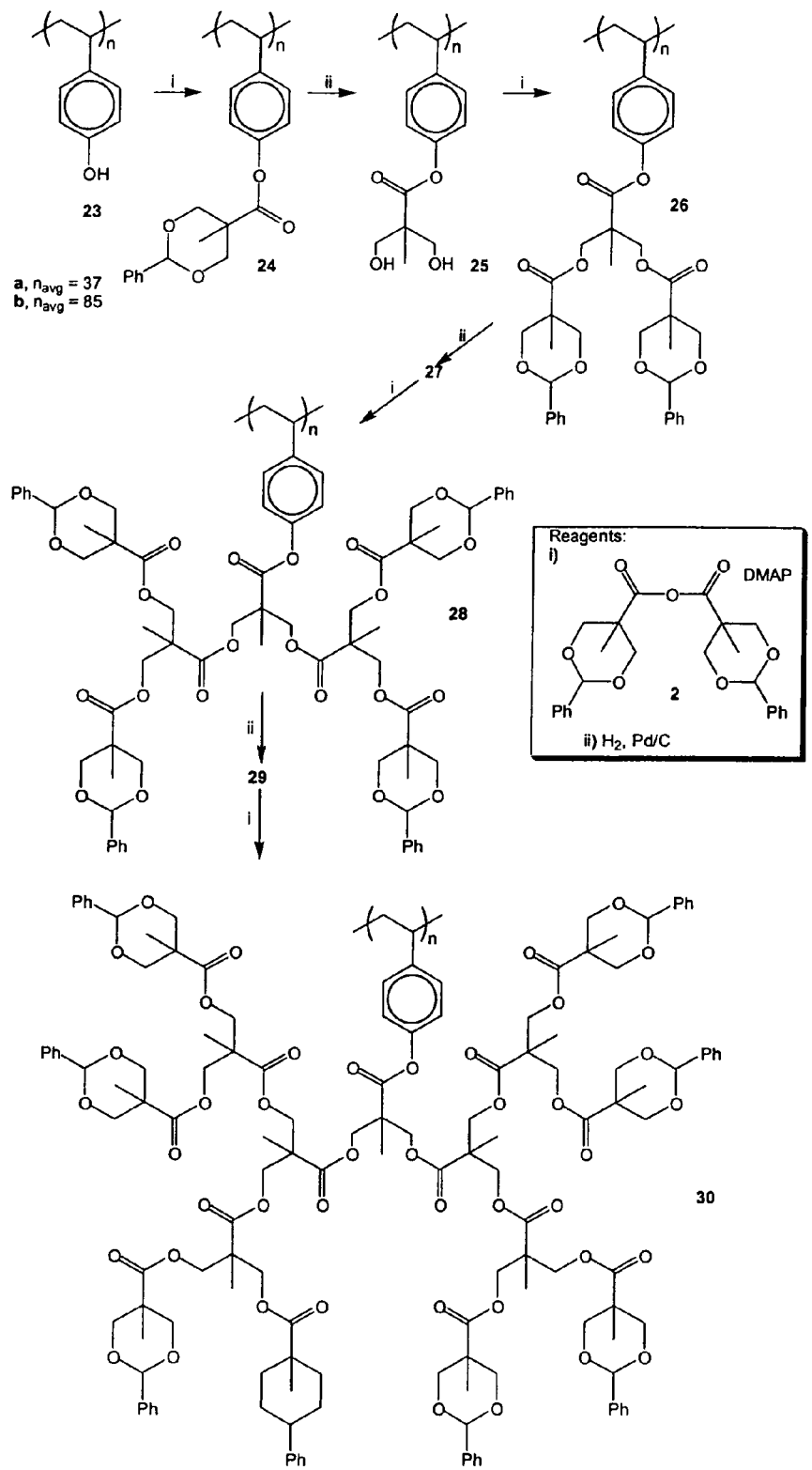
FIG. 4 is an exemplary synthetic scheme for the dendronization of a polymeric core moiety.

Referring to FIG. 4, in an exemplary embodiment, a dendrimer of the invention is assembled upon a poly(hydroxystyrene) core. Poly(hydroxystyrene) 23 is acylated with anhydride 2, producing ester 24, which is subsequently deprotected by hydrogenolysis to afford diol 25. The second generation dendrimer is prepared upon the core formed by diol 25, by acylating this compound with anhydride 2, producing ester 26, which is deprotected, forming diol 27. The third generation dendrimer is formed upon the core of compound 27, as discussed above, affording protected third generation dendrimer 30, which is optionally deprotected and submitted to one or more further rounds of elaboration, functionalized with an agent (e.g., therapeutic, diagnostic, etc.), or both.

A further component of this invention involves water-soluble branched macromolecules in which the core itself is a macromolecule that may be linear, star, or branched. In a preferred implementation the dendrimer is grown to a generation number of 1 through 5 and the core component is a linear or star-like poly(ethylene oxide). In a preferred implementation of this invention, the poly(ethylene oxide) core carries from one to twelve dendrons attached to it. The molecular weight of the poly(ethylene oxide) is typically in the range 500 to 1,000,000, preferably 1,000 to 100,000 and most preferably 5,000 to 60,000.

In an exemplary embodiment, a well-defined poly(ethylene oxide) is used as a core moiety in the preparation of the polyester dendrimer. Alternatively, aliphatic polyester dendrons are grafted onto the terminal groups of an end reactive core poly(ethylene oxide) macromolecule. The function of the poly(ethylene oxide) core is to act as a water-soluble core molecule for the dendrimer; an additional function of the poly(ethylene oxide) core is to increase the molecular weight of the dendrimer to increase its body circulation time, for example when injected intravenously; another function of the poly(ethylene oxide) core is to increase the solubility of the dendrimer both before and after conjugation with a drug or other active moiety; another function of the poly (ethylene oxide) (PEO) core is to participate in any desired micellization process; another function of the poly(ethylene oxide) core is to act as a steric stabilizer, another function of the poly(ethylene oxide) core is to protect the dendrimer from unfavorable or destructive interactions with the immune system; yet another function of the PEO core is in the attachment of an active (e.g., targeting) moiety at one or more of its chain ends, while one or more dendrons are attached to one or more of its other chain-ends.

Figure 2A:
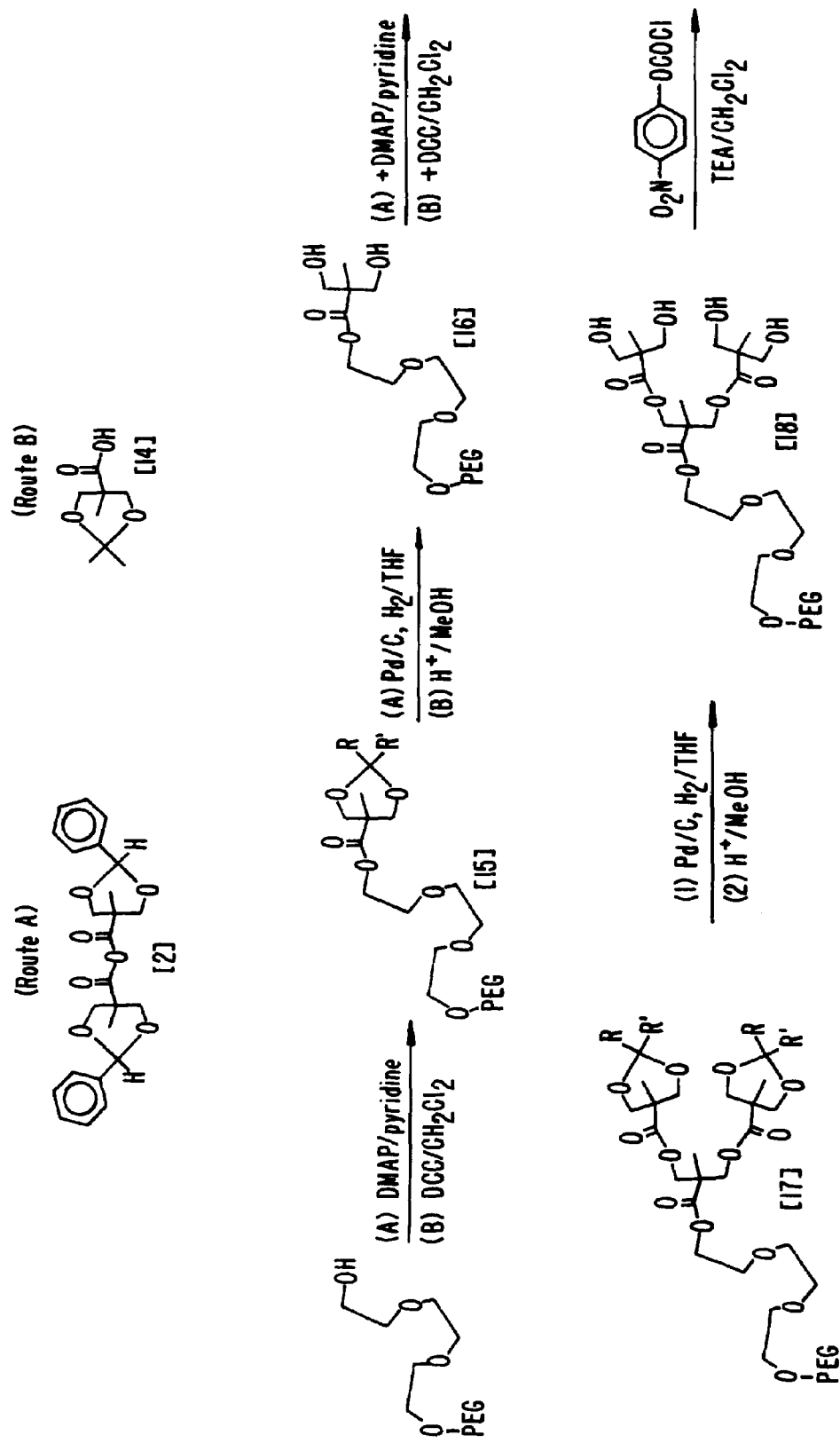
FIG. 2 is an exemplary reaction scheme for preparing a PEO-based drug-dendrimer conjugate of the invention.
Figure 2B:
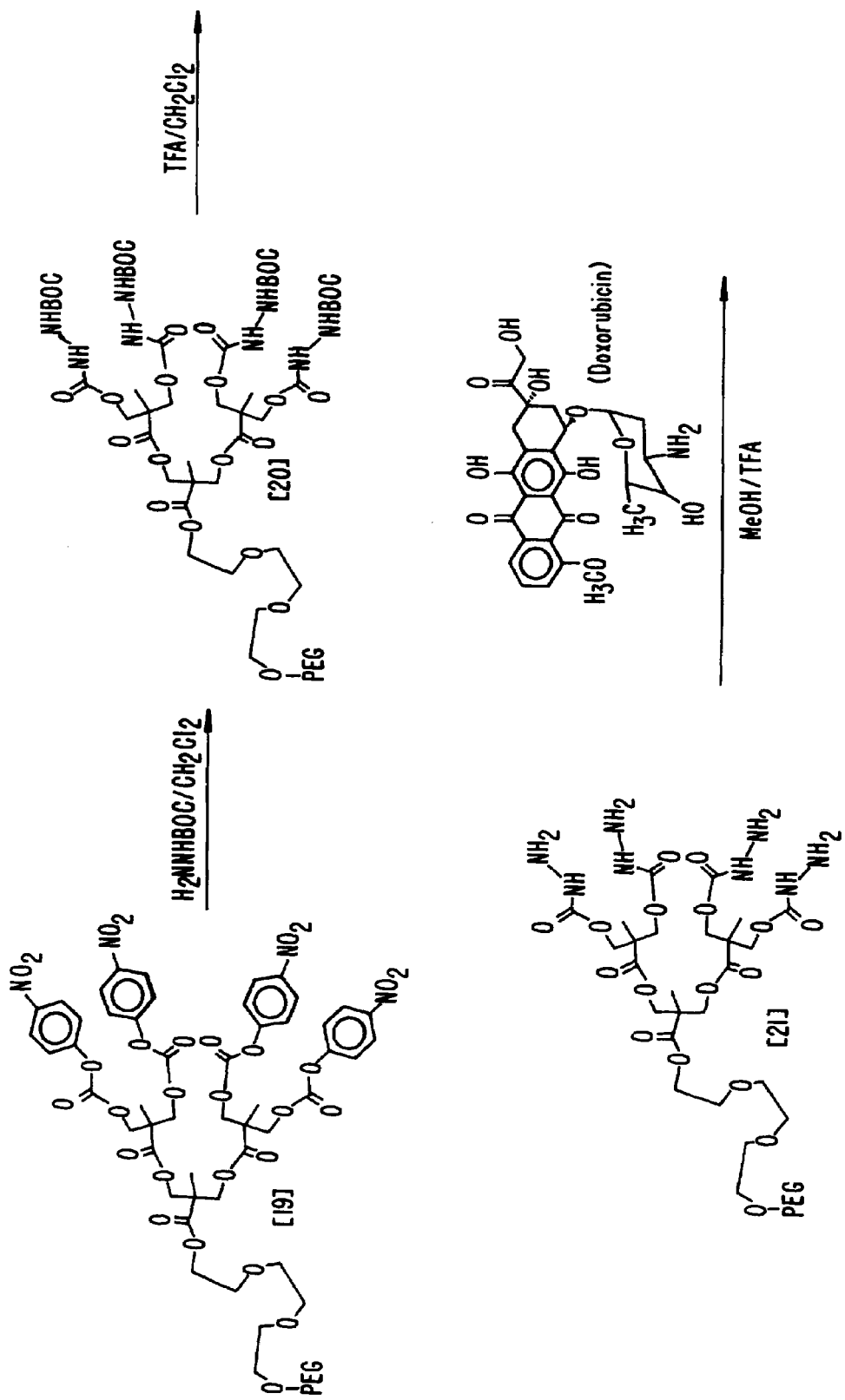
Figure 3A:
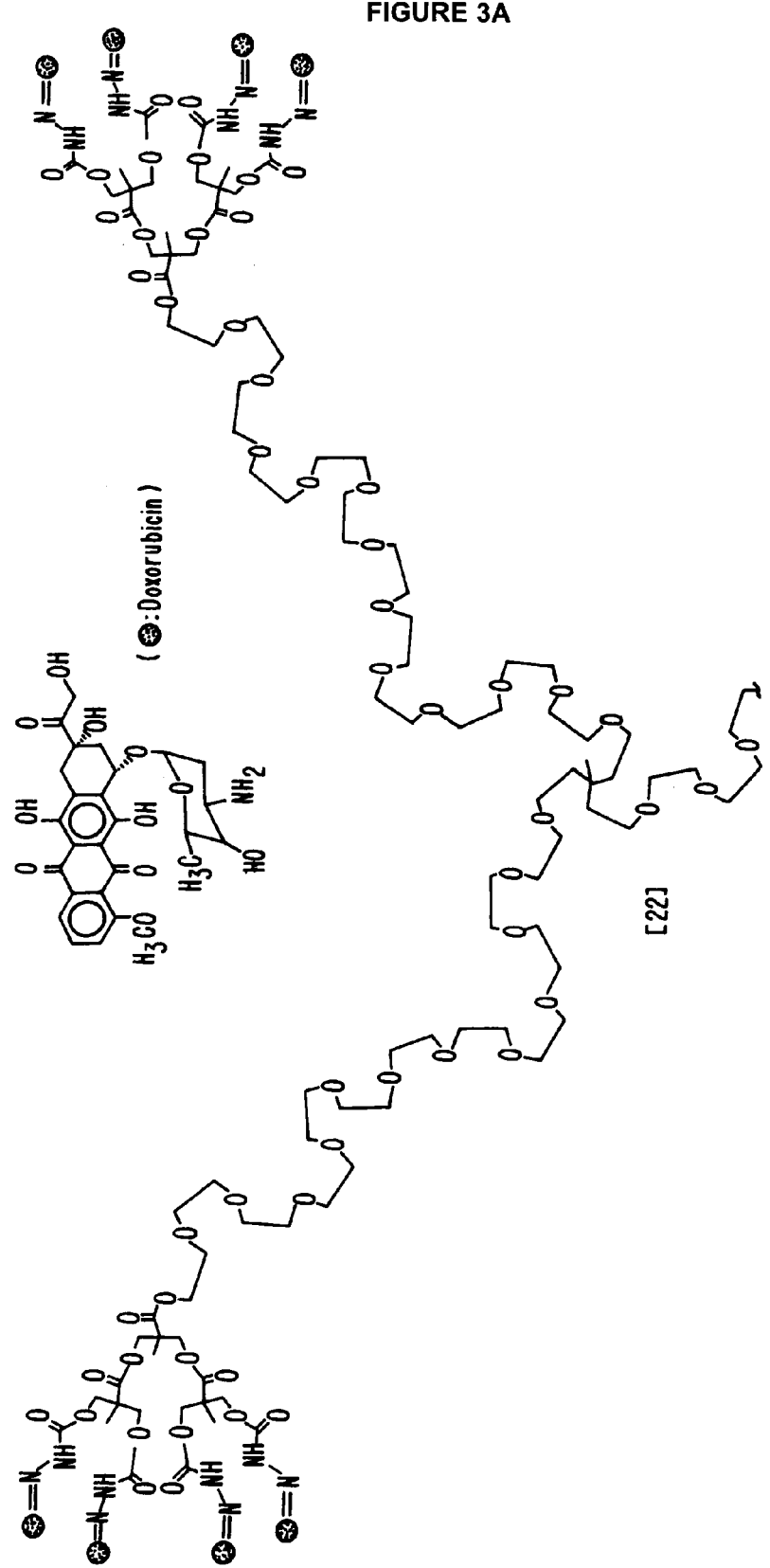
FIG. 3 is an exemplary synthetic scheme for coupling doxorubicin to a dodecahydrazide functional dendritic carrier of the invention.
Figure 3B:
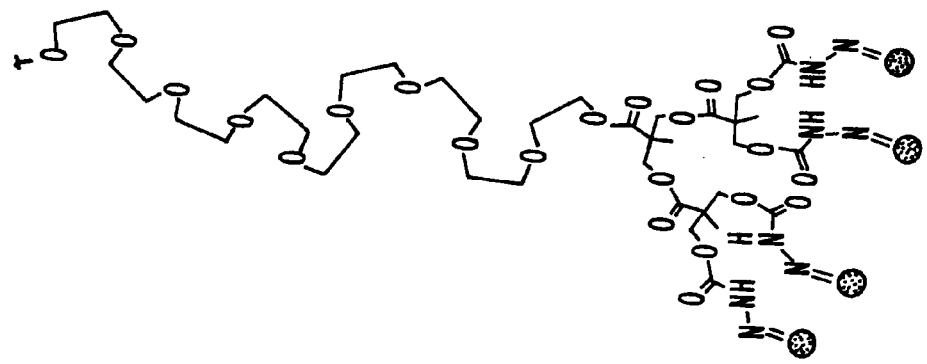

In an exemplary embodiment, a three-arm star poly(ethylene oxide), with a molecular weight of 20,000 Dalton and a polydispersity of 1.03 is the trifunctional core moiety in the divergent growth of aliphatic ester dendrimers. In the divergent synthesis of aliphatic ester dendrimers with poly (ethylene oxide) cores, two different synthetic approaches can be used as outlined in FIG. 2. For clarity of illustration, the structure of the starting poly(ethylene oxide) in FIG. 2 is simplified to show only three monomer units forming one of its chain ends connecting to a generic poly(ethylene oxide). This general schematic representation is understood to represent a linear or star-like poly(ethylene oxide) as defined earlier in this specification; in the case of a star-like poly (ethylene oxide), the structure is understood to contain several of the chain-ends shown in the Scheme. In route (A), the previously described anhydride coupling involving 2 is used in the divergent growth of higher generation dendrons from the hydroxyl functional poly(ethylene oxide) chain ends. In route (B), the 1,3-diol moiety of bis-hydroxymethyl-propanoic acid is first masked by an acetonide group (structure 14). The stepwise growth is enabled by DCC coupling using DMAP as a catalyst. In both approaches a modest excess of reagent is preferably used in the synthesis of the next higher generation to ensure a full coupling of all hydroxyl groups. Both route (A) and (B) result in well-defined dendritic aliphatic ester-poly(ethylene oxide) hybrids in high yields. Route (A) also offers optional deprotection either via hydrogenolysis or via hydrolysis. Despite its polyester component, this poly(ethylene oxide) core dendritic macromolecule 18 is highly water-soluble and is even less cytotoxic than the previously evaluated hydroxyl functional aliphatic ester dendrimer.

If desired, the functionalization reactions are stopped at an intermediate stage in which not all of the reactive groups of a star or branched poly(ethylene oxide) or of the growing dendron are reacted. In such cases less regular structures are obtained. Alternatively, partial reaction can be carried out using less anhydride 2 in the coupling step.

It will be apparent to those of skill in the art that other poly(ethylene oxide) architectures such as linear poly(ethylene oxide), star poly(ethylene oxide) with more than three branches, and branched poly(ethylene oxide) of different molecular weights can also be used as cores in the synthesis of poly(ethylene oxide)-core aliphatic ester dendrimers.

When the core moiety is a polysaccharide, it is preferably a member selected from cyclodextrin, starch, hydroxyethyl starch, chitosan and dextran. By way of exemplification, cyclodextrins are a group of cyclic oligosaccharides produced by numerous microorganisms. Cyclodextrins have a ring structure, which has a basket-like shape. This shape allows cyclodextrins to include many kinds of molecules into their internal cavity. See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978. Cyclodextrins are able to form inclusion complexes with an array of organic molecules including, for example, adamantane, drugs, pesticides, herbicides and agents of war. See, Tenjarla et al., *J. Pharm. Sci.* 87:425–429 (1998); Zughul et al., *Pharm. Dev. Technol.* 3:43–53 (1998); and Albers et al., *Crit. Rev. Ther. Drug Carrier Syst.* 12:311–337 (1995). The cyclodextrin moiety can be attached directly to the dendrimeric moiety or it can be attached through a spacer arm. See, Yamamoto et al., *J. Phys. Chem. B* 101:6855–6860 (1997). Methods to attach cyclodextrins to other molecules are well known to those of skill in the chromatographic and pharmaceutical arts. See, Sreenivasan, K. *J. Appl. Polym. Sci.* 60:2245–2249 (1996).

Exemplary poly(amino acids) and polyamides include those that incorporate lysine, tyrosine, serine, cysteine, arginine, histidine and combinations thereof within their structures, although poly(amino acids) that do not incorporate these amino acids are within the scope of the invention. (note the wording I used above where. In an exemplary embodiment, a poly(amino acid) or polyamide is used to add one or more residues containing OH or NH or SH pendant groups with other amide forming moieties.

Figure 5:
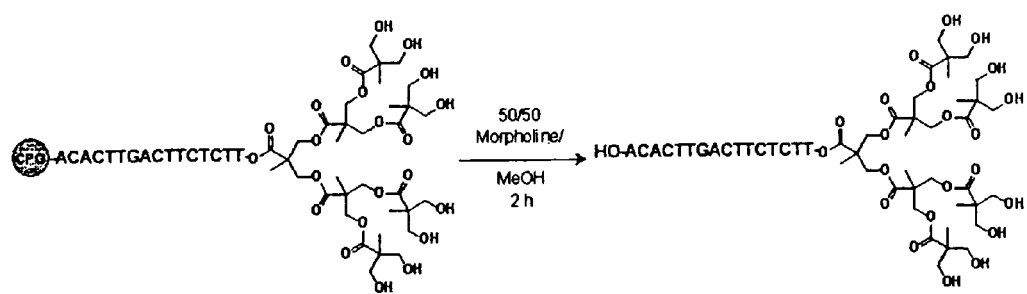
FIG. 5 is an exemplary nucleic acid-dendrimer conjugate.

When the core moiety is a nucleic acid, the dendrimer is preferably attached through the 3'- or 5'-terminal hydroxy moiety, although it may also be attached to one or more exocyclic amine residues. The dendrimer can also be appended to a phosphate group or a derivative thereof through, e.g., and ester or amide linkage. The attachment of the dendrimer to more than one of the above-recited attachment points is within the scope of the invention. FIG. 5 sets forth an exemplary nucleic acid-dendrimer conjugate of the invention.

In a further preferred embodiment, the present invention provides a dendrimer with a core moiety that is derived from an aromatic alcohol. The aromatic polyol can be mono- or poly-cyclic, substituted or unsubstituted. Moreover, the aromatic polyol can be carbocyclic or heterocyclic. An exemplary core derived from an aromatic polyol has the structure:

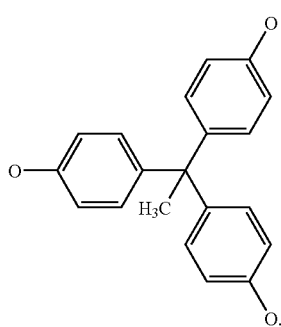

Additional examples of small molecule cores include pentaerythritol, mannitol, simple sugars such as glucose, fructose, sucrose, cellobiose, maltose, $NH_2$—$(CH_2)_n$—$NH_2$ or branched amines, such as those shown below in which n=2–6:

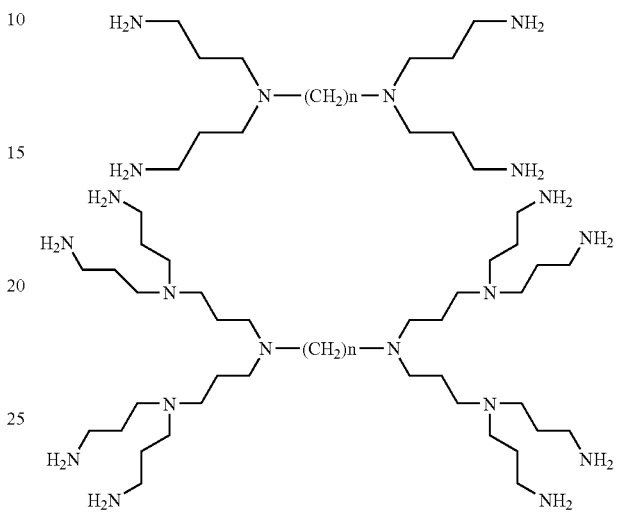

Other exemplary macromolecular cores derived from species with multiple active groups include, e.g., vinyl polymers such as poly(hydroxyethyl methacrylate), poly (vinylphenol); poly(hydroxyethyl acrylate), poly(N-2-hydroxypropylmethacrylamide), poly(diallylamine), and condensation polymers, such as poly(hydroxymethylcaprolactone), poly(4-hydroxyethylcaprolactone).

Still further exemplary macromolecular cores derived from species containing multiple amino groups include linear or branched polyethyleneimine, aninated polysaccharides such as chitosan, linear or branched polymers of amino acids such as poly(lysine), poly(amidoamine) dendrimers, and poly(propyleneimine) dendrimers.

In another embodiment, Y is itself a dendrimeric moiety, such that a dendrimer of a higher generation is formed.

In other embodiments, Y is the "core" of the dendrimer and Y is a therapeutic, analytical or diagnostic agent. Most preferably, Y is a nucleic acid. $R^9$ and $R^{10}$ represent members independently selected H and the species discussed above in the context of the core moiety. In a preferred embodiment, $R^9$ and $R^{10}$ are independently selected from H and poly(ethylene oxide).

The generations of the dendrimer are built up by repeated acylation/deprotection cycles until a dendrimer of the desired generation having the desired $R^5$ and $R^6$ groups. In addition to the anhydrides set forth above, the invention provides dendrimers in which anhydrides of other carboxylic acids are utilized. Exemplary anhydrides include that of protected amino benzoic acid (e.g, t-BOC protected), or of a protected amino acid (e.g., Cbz beta alanine). The protected amino acid anhydrides are used to terminate the dendrimer of to build up intermediate layers.

By way of example, Scheme 2 sets forth the synthesis of a beta alanine terminated dendrimer of the invention:

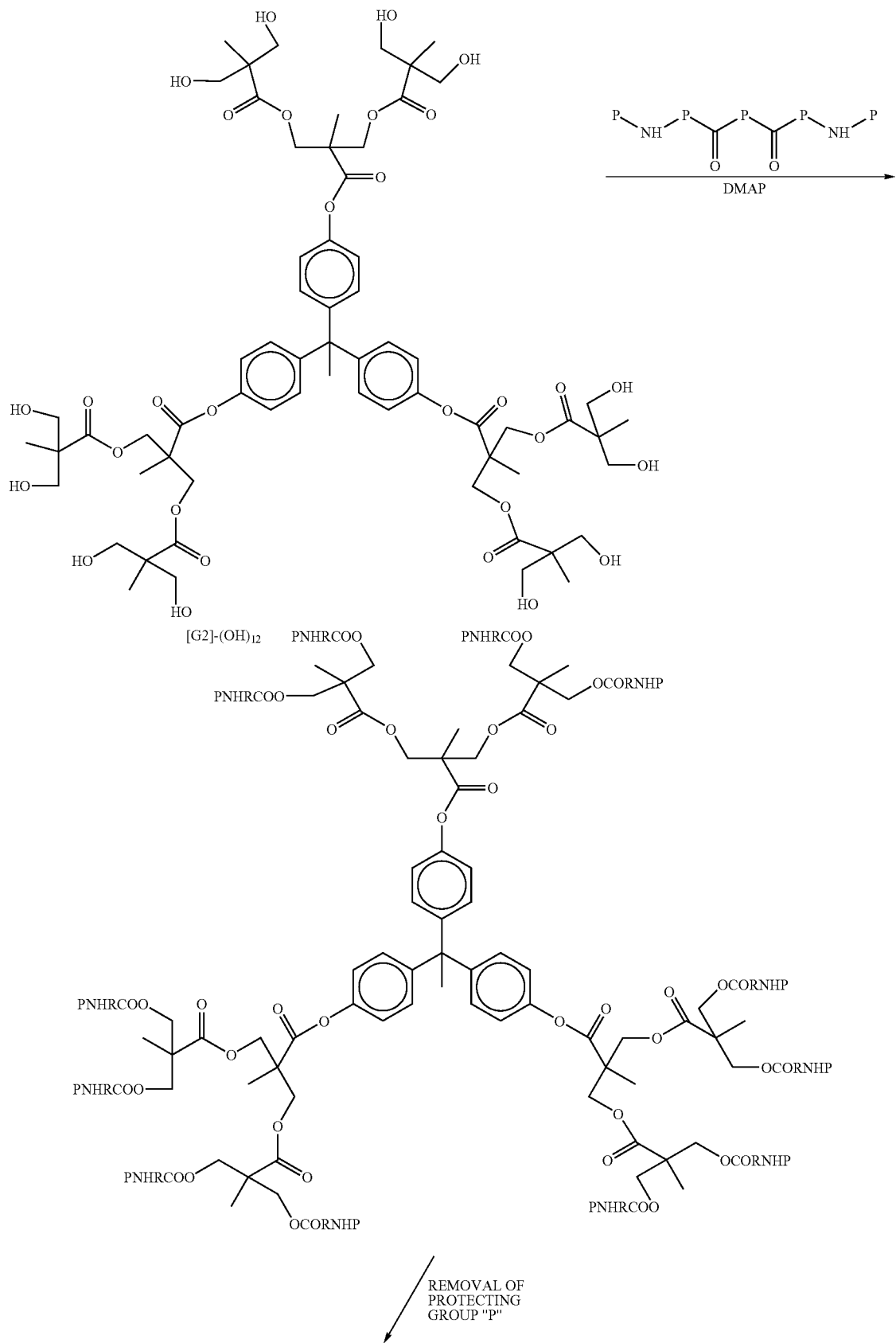
Scheme 2

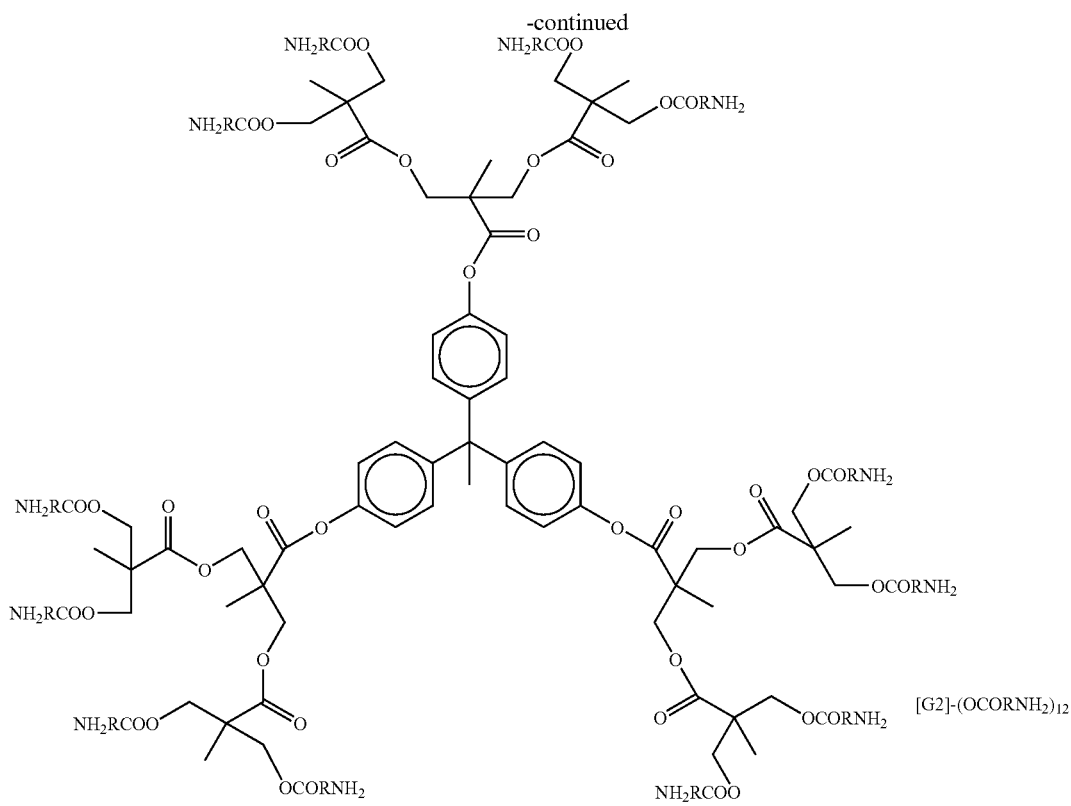

[G2]-(OCORNH$_2$)$_{12}$ in which R is substituted or unsubstituted aryl, substituted or unsubstituted alkyl, substituted or unsubstituted aralkyl; and P is an amino protecting group. As set forth in Scheme 2, a first generation, deprotected dendrimer of the invention is contacted with the N-protected, symmetrical anhydride of beta alanine, thereby acylating the reactive hydroxyl groups of the first generation dendrimer. The protecting groups are removed from the amine groups of the beta alanine, forming a dendrimer terminated with reactive amine groups.

For example anhydrides of amino-acids in which the amino group is protected by a amine protecting group such as t-BOC, Fmoc, carbobenzyloxy (Cbz), or other amine protecting group used commonly in the preparation of oligo or polypeptides can be used (see, e.g., PRINCIPLES OF PEPTIDE SYNTHESIS by M. Bodansky, Springer Verlag, NY 1984, pages 82–111; and PROTECTIVE GROUPS IN OGANIC SNTHESIS" by T. W. Greene and P. G. M. Wuts, 2nd Ed, Wiley, NY 1991, Pages 309–397). Such protecting groups can later be removed under conditions that do not affect the ester linkages of the dendritic molecules to expose free amino groups. For example the Cbz group is removed by hydrogenolysis, and the Fmoc group by reaction with mild base such as piperidine or morpholine.

The amino acids that can be used in the present invention include not only natural amino acids but also synthetic amino acids, both aromatic or aliphatic as exemplified by the anhydrides of protected amino acids set forth below:

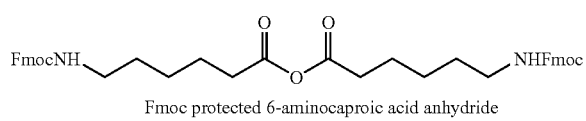

Fmoc protected 6-aminocaproic acid anhydride

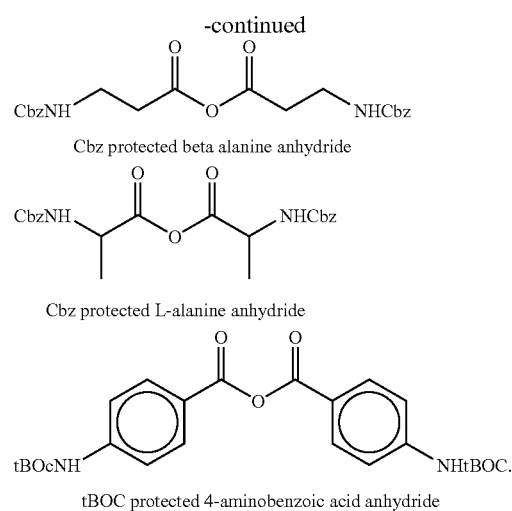

Cbz protected beta alanine anhydride

Cbz protected L-alanine anhydride tBOC protected 4-aminobenzoic acid anhydride

The present invention also provides pharmaceutical formulations of the compounds of the invention. The formulations preferably include a compound of the invention in combination with a pharmaceutically acceptable diluent, excipient or the like. The pharmaceutical formulations are preferably substantially free of N-acyl urea side products.

The dendrimers of the present invention are useful for delivering therapeutic, diagnostic and analytical agents both extra- and intra-cellularly. Thus, in another preferred embodiment, the invention provides a biological compartment having a dendrimer located inside the compartment. The compartment is defined by a membrane, and is selected from cells and organelles. The biological compartment of the invention can be from any organism. Moreover, the dendrimers can be delivered to the cell interior by any method known in the art, e.g. passive or active transport, electroporation, osmotic disruption, etc.

The individual components of the dendrimer, particularly the protecting groups, therapeutic groups, diagnostic groups and analytical groups are described in greater detail below.

Diagnostic Agents

In a presently preferred embodiment, $R^{19}$ and $R^{20}$ are diagnostic agents. Exemplary diagnostic agents that are incorporated into the dendrimers of the invention include, for example, MRI contrast agents, X-ray contrast agents, CT contrast agents, PET contrast agents, ultrasonography contrast agents, fluorescent agents, chromophoric agents and radioisotopes.

The embodiment of the invention in which the diagnostic agent is a contrast agent is illustrated by reference to metal chelate-based contrast agents. The focus on metal chelates is intended as illustrative rather than limiting. Those of skill in the art will appreciate that many contrast agents other than metal chelates can be conjugated to the dendrimers of the invention (e.g. particles, iodinated aryl compounds, nitroxides, etc.).

An array of metal chelates is known in the art. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279–312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

In a preferred embodiment, the diagnostic agent is a metal complex of polyaminocarboxylate chelating agent such as ethylenediaminetetraacetic acid (EDTA) or diethylenetriaminepentaacetic acid (DTPA). In an exemplary embodiment, the diagnostic agent is attached to an amine-derivatized dendrimer of the invention or a linker group attached to the dendrimer, for example, by utilizing a commercially available anhydride (e.g., DTPA-bis-anhydride; Aldrich Chemical Co., Milwaukee, Wis.).

In another preferred embodiment, the analytical agent is a cyclodextrin or modified cyclodextrin. Cyclodextrins are a group of cyclic oligosaccharides produced by numerous microorganisms. These basket shaped polysaccharides are able to form inclusion complexes with an array of organic molecules including, for example, adamantane, drugs, pesticides, herbicides and agents of war. See, Tenjarla et al., *J. Pharm. Sci.*, 87: 425–429 (1998); Zughul et al., *Pharm. Dev. Technol.*, 3: 43–53 (1998); and Albers et al., *Crit. Rev. Ther. Drug Carrier Syst.*, 12: 311–337 (1995); Szejtli, CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

In still further exemplary embodiments, the diagnostic agent is a biomolecule such as a protein, nucleic acid, peptide or an antibody. Biomolecules useful in practicing the present invention can be derived from any source. The biomolecules can be isolated from natural sources or they can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Moreover, antibody fragments containing the recognition component can be used, rather than the whole antibody. Peptides and nucleic acids can also be used and these can be isolated from natural sources or they can be wholly or partially synthetic in origin.

In those embodiments wherein the diagnostic moiety is an enzyme or antibody, the protein can be tethered directly to a dendrimer component or via a linker group through any reactive peptide residue available on the surface of the protein. In preferred embodiments, the reactive groups are amines or carboxylates. In particularly preferred embodiments, the reactive groups are the ε-amine groups of lysine residues.

Diagnostic agents that are antibodies can be used to recognize numerous species of diagnostic interest, e.g., proteins, peptides, nucleic acids, saccharides or small molecules such as drugs, herbicides, pesticides and the like. Methods of raising antibodies for specific molecules are well known to those of skill in the art. See, U.S. Pat. No. 5,147,786, issued to Feng et al. on Sep. 15, 1992; U.S. Pat. No. 5,334,528, issued to Stanker et al on Aug. 2, 1994; U.S. Pat. No. 5,686,237, issued to Al-Bayati, M. A. S. on Nov. 11, 1997; and U.S. Pat. No. 5,573,922, issued to Hoess et al on Nov. 12, 1996. Methods for attaching antibodies to other molecules, such as the dendrimers of the invention are also known in the art. See, for example, Delamarche et al. *Langmuir,* 12:1944–1946 (1996), Hermanson, BIOCONJUGATE TECHNIQUES, Academic press, San Diego, 1996.

ANALYTICAL AGENTS

As there is often a degree of overlap between the analytical application of a probe and its diagnostic function, the discussion above regarding diagnostic agents and the discussion, which follows, are generally relevant to each other. For most diagnostic or analytical uses it preferred that the dendrimer is provided with a label for the detection of the dendrimer or the structure, which takes up or is otherwise associated with the dendrimer. Alternatively, a combination of labeled and unlabelled dendrimer may be employed. The substance used as label is selected from any substance which is in itself detectable or which can be reacted with another substance to produce a detectable product. Thus, the label may be selected from radioactive isotopes, enzymes, chromophores, fluorescent or chemiluminescent substances, and complexing agents. Also, as discussed above, the present invention provides dendrimers in which the core moiety is a fluorophore, fluorogenic material or a chromophore or chromogenic species. Thus, the following discussion is generally applicable to both agents conjugated to dendrimers of the invention and to the core moiety of dendrimers of the invention. The focus of the following paragraphs on the use of detectable agents as labels conjugated to dendrimers is for clarity of illustration and does not limit the use of such agents in the present invention.

Non-limiting examples of enzymes useful as labels are β-galactosidase, urease, glucose oxidase, carbonic anhydrase, peroxidases (e.g. horseradish peroxidase), phosphatases (e.g. alkaline or acid phosphatase), glucose-6-phosphate dehydrogenase and ribonuclease.

Enzymes are generally not in themselves detectable, but must be combined with a substrate to catalyze a reaction the end product of which is detectable. Thus, a substrate may be added to the labeled dendrimer resulting in a colored, fluorescent or chemiluminescent product or in a color change or in a change in the intensity of the color, fluorescence or chemiluminescence. Examples of substrates which are useful as substrates for the enzymes mentioned above are $H_2O_2$, p-nitrophenylphosphate, lactose, urea, β-D-glucose, $CO_2$, RNA, starch, or maleate. The substrate may be combined with, e.g. a chromophore which is either a donor or acceptor of light energy Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803–808 (1982); Levine et al., *Comp. Biochem. Physiol.*, 72B:77–85 (1982)), yellow fluorescent protein from *Vibrio fischeri* strain (Baldwin et al., *Biochemistry* 29:5509–15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226–35 (1993)), and the like.

The compounds, probes and methods discussed herein are generally representative of the compositions of the invention and the methods in which such compositions can be used. The following discussion is intended as illustrative of selected aspects and embodiments of the present invention and it should not be interpreted as limiting the scope of the present invention.

A non-limiting list of fluorescent agents is provided in Table 1.

TABLE 1

4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:

coumarin
7-amino-4-methylcoumarin (AMC, Coumarin 120)
7-amino-4-trifluoromethylcouluarin (Coumarin 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate TABLE 1-continued 4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

pyrene
pyrene butyrate
succinimidyl 1-pyrene butyrate
quantum dots
Reactive Red 4 (Cibacron™ Brilliant Red 3B-A)
rhodamine and derivatives:

6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives There is a great deal of practical guidance available in the literature for selecting appropriate donor-acceptor pairs for particular probes, as exemplified by the following references: Pesce et al., Eds., Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (supra); Ullman et al., U.S. Pat. No. 3,996,345; Khanna et al., U.S. Pat. No. 4,351,760.

Chromophores may be, for example, o-phenylenediamine or similar compounds. These substances may be detected by any means known in the art, e.g. with a spectrophotometer.

Radioactive isotopes may be any detectable isotope, e.g., $^{125}I$, $^{131}I$, $^{3}H$, $^{35}P$, $^{35}S$ or $^{14}C$. The radioactivity may be measured using any method known in the art, e.g., in a γ-counter or a scintillation counter or by autoradiography followed by densitometry.

Therapeutic Agents

In another exemplary embodiment, the present invention provides dendrimers that are derivatized with one or more therapeutic agents. The therapeutic agent may be attached to the dendrimer through the "arms" of the dendrimer or, alternatively, it forms the core moiety of the dendrimer. The use of any therapeutic agent that can be attached to a dendrimer of the invention is within the scope of the present invention.

Exemplary pharmaceutical agents or drugs that may be delivered by the system of the present invention include analgesics, anesthetics, antifungals, antibiotics, antiinflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, corticoids (steroids), antidepressants, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasoconstrictors, vasodilators, vitamins, xanthine derivatives, and the like.

In another exemplary embodiment, the species conjugated to the dendrimer or the core moiety is a therapeutic moiety. The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a target of choice. As such, therapeutic moieties, which are useful in practicing the instant invention include drugs from a broad range of drug classes having a variety of pharmacological activities.

Exemplary classes of useful agents include, but are not limited to, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine);diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The therapeutic agent can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful therapeutic moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Protein and peptide drugs, as well as other amino acid-based drugs, may also be used as therapeutic agents according to the present invention. Protein and peptide drugs are capable of covalently binding to the dendrimer and so can serve as pharmaceutical agents according to the present invention. For example, most protein and peptide drugs possess either an amino, carboxy, hydroxy, or mercapto group that can be used to bind covalently to a the dendrimer or spacer group. According to this aspect of the invention, particularly preferred as protein and peptide drugs include those, which contain either a cysteine or a lysine residue. The mercapto group of cysteine and the $\epsilon$-amino group of lysine can be used as chemical functionality to bind to a dendrimer or spacer group.

In the case of certain protein and peptide drugs, additional chemical functionality can be introduced into the drug by site-directed mutagenesis. For example, protein and peptide drugs, which are not amenable to coupling with a dendrimer can be modified using recombinant DNA techniques. These modifications could entail the replacement of an existing amino acid of the drug with an amino acid or other group, which can be easily coupled to a dendrimer or the addition of amino acid(s) or other group(s) which can be easily coupled to a dendrimer. In some instances, the net charge, charge distribution, or charge localization of the protein itself is modified using recombinant techniques.

Amino acid-based drugs, such as the cephalosporins, will typically have a molecular weight less than about 5000, and preferably, less than about 2500, and more preferably, less than about 1000. Protein and peptide drugs typically have a molecule weight of at least about 100 daltons, and more typically a molecular weight in the range of about 200 to 40,000 daltons. Specific examples of peptides and proteins in this size range include, but are not limited to, those found in, for example Hale, et al., U.S. Pat. No. 5,607,691, Mar. 4, 1997.

Heretofore, nucleotide-based drugs have had limited success as therapeutic agents, in part, because of problems associated with their stability and delivery. Nucleotide-based pharmaceutical agents frequently contain a phosphodiester bond, which is sensitive to degradation by nucleases. Such degradation would be a significant impediment to the use of an oligonucleotide or nucleic acid as a pharmaceutical agent that depends upon the integrity of the sequence for its recognition specificity. Thus, naturally occurring oligonucleotides and nucleic acids often must be chemically modified to render them resistant to nucleases which would degrade them in vivo, or even in vitro unless care is taken to choose appropriate conditions.

The nucleotide-based drugs of the present invention include aptamers, antisense compounds, and triple helix drugs. Typically, a hydroxyl group of a sugar residue, an amino group from a base residue, or a phosphate oxygen of the nucleotide will be utilized as the needed chemical functionality to couple the nucleotide-based drug to the dendrimer. However, one of skill in the art will readily appreciate that other chemical functionalities can be prepared by conventional techniques. For example, the hydroxyl group of the sugar residue can be converted to a mercapto or amino group using techniques well known in the art.

The nucleotide-based drugs typically will have a molecular weight greater than about 350 and may range up to about 100 bases. Examples of nucleotide-based drugs include di- and trinucleotides, such as GS 375, a dinucleotide analog with potential therapeutic activity against the influenza virus (Gilead Sciences, Inc., Foster City, Calif.), aptamers, antisense compounds, and triple helix drugs.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Aptamers possess chemical functionality and thus, can covalently bond to dendrimers, as described herein.

Although a wide variety of molecular targets will be capable of forming non-covalent but specific associations with aptamers, including small molecules drugs, metabolites, cofactors, toxins, saccharide-based drugs, nucleotide-based drugs, glycoproteins, and the like, generally the molecular target will comprise a protein or peptide, including serum proteins, kinins, eicosanoids, cell surface molecules, and the like. Examples of aptamers include Gilead's antithrombin inhibitor GS 522 and its derivatives (Gilead Science, Foster City, Calif.). See also, Macaya et al. *Proc. Natl. Acad. Sci. USA* 90:3745–9 (1993); Bock et al. *Nature (London)* 355:564–566 (1992) and Wang et al. *Biochem.* 32:1899–904 (1993).

Aptamers specific for a given biomolecule can be identified by using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No. 92/05285; and Ellington and Szostak, *Nature* 346:818 (1990). Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript which is essential for pre-mRNA processing, or to a sequence within the gene itself. This paradigm for genetic control is often referred to as antisense or antigene inhibition.

Antisense compounds are nucleic acids that are designed to bind and disable or prevent the production of the mRNA responsible for generating a particular protein. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching et al. *Proc. Natl. Acad. Sci. U.S.A.* 86:10006–10010 (1989); Broder et al. *Ann. Int. Med.* 113:604–618 (1990); Loreau et al. *FEBS Letters* 274:53–56 (1990); Holcenberg et al. WO91/11535; WO91/09865; WO91/04753; WO90/13641; WO 91/13080, WO 91/06629, and EP 386563).

Antisense compounds can provide a therapeutic function by inhibiting in vivo the formation of one or more proteins that cause or are involved with disease. Antisense compounds complementary to certain gene messenger RNA or viral sequences have been reported to inhibit the spread of disease related to viral and retroviral infectious agents (See, for example, Matsukura et al. *Proc. Natl. Acad. Sci. USA* 84:7706 (1987), and references cited therein).

Others have reported that nucleic acids can bind to duplex DNA via triple helix formation and inhibit transcription and/or DNA synthesis. Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and prevent the cell from making a target protein. See, e.g., PCT publications Nos. WO 92/10590, WO 92/09705, WO91/06626, and U.S. Pat. No. 5,176,996.

The site specificity of nucleic acids (e.g., antisense compounds and triple helix drugs) is not significantly affected by modification of the phosphodiester linkage or by chemical modification of the oligonucleotide terminus. Consequently, these nucleic acids can be chemically modified; enhancing the overall binding stability, increasing the stability with respect to chemical degradation, increasing the rate at which the oligonucleotides are transported into cells, and conferring chemical reactivity to the molecules. The general approach to constructing various nucleic acids useful in antisense therapy has been reviewed by van der Krol et al., *Biotechniques* 6:958–976 (1988) and Stein et al. *Cancer Res.* 48:2659–2668 (1988).

Accordingly, aptamers, antisense compounds and triple helix drugs also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, e.g., Campbell et al., *J. Biochem. Biophys. Methods* 20:259–267(1990)). Phosphoramidate derivatives of oligonucleotides also are known to bind to complementary polynucleotides and have the additional capability of accommodating covalently attached ligand species and will be amenable to the methods of the present invention. See, for example, Froehler et al., *Nucleic Acids Res.* 16(11):4831 (1988).

In some embodiments the aptamers, antisense compounds and triple helix drugs will comprise O-methylribonucleotides (EP Publication No. 360609). Chimeric oligonucleotides may also be used (Dagle et al., *Nucleic Acids Res.* 18:4751 (1990)). For some applications, antisense oligonucleotides and triple helix may comprise polyamide nucleic acids (Nielsen et al, *Science* 254: 1497 (1991) and PCT publication No. WO 90/15065) or other cationic derivatives (Letsinger et al., *J. Am. Chem. Soc.* 110: 4470–4471 (1988)). Other applications may utilize oligonucleotides wherein one or more of the phosphodiester linkages has been substituted with an isosteric group, such as a 2–4 atom long internucleoside linkage as described in PCT publication Nos. WO 92/05186 and 91/06556, or a formacetal group (Matteucci et al., *J. Am. Chem. Soc.* 113: 7767–7768 (1991)) or an amide group (Nielsen et al., *Science* 254: 1497–1500 (1991)).

In addition, nucleotide analogs, for example wherein the sugar or base is chemically modified, can be employed in the present invention. "Analogous" forms of purines and pyrimidines are those generally known in the art, many of which are used as chemotherapeutic agents. An exemplary but not exhaustive list includes 4-acetylcytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, .beta.-D-mannosylqueosine, 5'methoxycarbonylmethyluracil, 5-methoxyuracil, 2-methylthio-$N^{6}$-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine. In addition, the conventional bases by halogenated bases. Furthermore, the 2'-furanose position on the base can have a non-charged bulky group substitution. Examples of non-charged bulky groups include branched alkyls, sugars and branched sugars.

Terminal modification also provides a useful procedure to modify cell type specificity, pharmacokinetics, nuclear permeability, and absolute cell uptake rate for oligonucleotide pharmaceutical agents. For example, substitutions at the 5' and 3' ends include reactive groups, which allow covalent crosslinking of the nucleotide-based pharmaceutical agent to other species and bulky groups which improve cellular uptake. See, e.g., OLIGODEOXYNUCLEOTIDES: ANTISENSE INHIBITORS OF GENE EXPRESSION, (1989) Cohen, Ed., CRC Press; PROSPECTS FOR ANTISENSE NUCLEIC ACID THERAPEUTICS FOR CANCER AND AIDS, (1991), Wickstrom, Ed., Wiley-Liss; GENE REGULATION: BIOLOGY OF ANTISENSE RNA AND DNA, (1992) Erickson and Izant, Eds., Raven Press; and ANTISENSE RNA AND DNA, (1992), Murray, Ed., Wiley-Liss. For general methods relating to antisense compounds, see, ANTISENSE RNA AND DNA, (1988), D. A. Melton, Ed., Cold Spring Harbor Laboratory, Cold Spring Harbor, N.Y.).

Antisense polynucleotides of various lengths may be delivered, although such antisense polynucleotides typically comprise a sequence of at least about 15 consecutive nucleotides. Examples of antisense compounds include G 1128 (Genta, Inc., San Diego, Calif.), OL(1)p53 (Lynx Pharmaceuticals), Ampligen (Hemm Pharmaceuticals), Isis 1082 and Isis 2105 (Isis Pharmaceuticals, Carlsbad, Calif.). Typically, the triple helix drug will comprise a DNA oligonucleotide in the range of about 20 to 40 bases.

The following sections discuss exemplary methods of forming the conjugates between the dendrimer and the analytical, diagnostic and therapeutic agents. For the purposes of the discussion, each of the three classed of agents, as well as other moieties that are attached to the dendrimer are referred to as "agents."

Methods of Activation

Generally, prior to forming the linkage between the dendrimer and the agent, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the dendrimer or agent can be activated through treatment with phosgene to form the corresponding chloroformate, or p-nitrophenylchloroformate to form the corresponding carbonate.

In an exemplary embodiment, the invention makes use of an agent that includes a carboxyl functionality. Carboxyl groups may be activated by, for example, conversion to the corresponding acyl halide or active ester. This reaction may be performed under a variety of conditions as illustrated in March, supra pp. 388–89. In a preferred embodiment, the acyl halide is prepared through the reaction of the carboxyl-containing group with oxalyl chloride. Those of skill in the art will appreciate that the use of carboxyl-containing agents is merely illustrative, and that agents having many other functional groups can be conjugated to the dendrimers of the invention.

Typically, the agent is linked covalently to a dendrimer using standard chemical techniques through their respective chemical functionalities. Optionally, the dendrimer or agent is coupled to the agent through one or more spacer groups. The spacer groups can be equivalent or different when used in combination. Likewise, if more than one dendrimer is used to produce the agent-dendrimer complex, the dendrimers can be equivalent or different.

The agent-dendrimer complex is prepared by linking an agent to a dendrimer (or optionally to a spacer group which has been or will be attached to a dendrimer) via their respective chemical functionalities. Those of skill in the art will recognize that one can first attach the spacer either to the dendrimer or to the agent. The exemplary chemical functionalities shown in Table 3 can be present on the pharmaceutical agent, spacer, or dendrimer, depending on the synthesis scheme employed. Table 3 provides examples of a first chemical functionality that is a component of either the agent or the dendrimer and a second chemical functionality that is a component of either the agent or the dendrimer. The exemplary linkages set forth in Table 3 are produced by the covalent interaction of chemical functionality 1 and 2.

The groups set forth in Table 3 are also generally representative of "active groups," which are found on core moieties of use in the present invention.

TABLE 3

| Chemical Functionality 1 | Chemical Functionality 2 | Linkage |
|---|---|---|
| Hydroxy | Carboxy | Ester |
|  | Hydroxy | Carbonate |
|  | Amine | Carbamate |
|  | $SO_3$ | Sulfate |
|  | $PO_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362–363, 491, 720–722, 829, 941, and 1172; for carbonates, see, March, supra at 346–347; for carbamates, see, March, supra at 1156–57; for amides, see, March supra at 1152; for ureas and thioureas, see, March supra at 1174; for acetals and ketals, see, Greene et al. supra 178–210 and March supra at 1146; for acyloxyalkyl derivatives, see, PRODRUGS: TOPCAL AND OCULAR DRUG D*ELIVERY*, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355–56, 636–37, 990–91, and 1154; for N-acylamides, see, March supra at 379; for N-Mannich bases, see, March supra at 800–02, and 828; for hydroxymethyl ketone esters, see, Petracek et al. *Annals NY Acad. Sci.*, 507:353–54 (1987); for disulfides, see, March supra at 1160; and for phosphonate esters and phosphonamidates, see, e.g., copending application Ser. No. 07/943, 805, which is expressly incorporated herein by reference.

In certain embodiments, one or more of the active groups are protected during one or more steps of the reaction to assemble the dendrimer or a conjugate of the dendrimer. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

A variety of ketal type linkages may be produced. Ketal type linkages that may be produced in the pharmaceutical agent-dendrimer complexes of the present invention include, but are not limited to, imidazolidin-4-ones, see, PRODRUGS, supra; oxazolin-5-ones, see, Greene et al,. supra at 358; dioxolan-4-one, see, Schwenker et al., Arch. Pharm. (Weinheim) 324:439 (1991); spirothiazolidines, see, Bodor et al. *Int. J. Pharm.*, 10:307 (1982) and Greene et al., supra at 219 and 292; and oxazolidines, see, March supra at 87 and Greene et al, supra at 217–218 and 266–267.

The processes for constructing or modifying nucleotides or nucleic acids are generally well known in the art. These processes are described in the patent and other literature. See, for example, U.S. Pat. Nos. 4,431,739 and 5,013,653. Additionally, nucleic acid construction principles can be exploited using various restriction enzymes which make sequence specific cuts in the nucleic acid to produce blunt ends or cohesive ends, DNA ligases, enzymatic addition of single-stranded ends to blunt-ended DNA, and construction of synthetic DNAs by assembly of short oligonucleotides.

A preferred linkage for peptide and protein pharmaceutical agents may be formed by the reaction of an aldehyde containing dendrimer or spacer group with the terminal amino acid of the pharmaceutical agent. This cyclic derivative serves to stabilize the pharmaceutical agent towards enzymatic action, yet is easily hydrolyzed to release the peptide drug.

Spacer Groups

One or more spacer groups optionally may be introduced between the dendrimer and the pharmaceutical agent. Spacer groups contain at least two chemical functionalities. Typically, one chemical functionality of the spacer group bonds to a chemical functionality of the dendrimer, while the other chemical functionality of the spacer group is used to bond to a chemical functionality of the pharmaceutical agent. Examples of chemical functionalities of spacer groups include hydroxy, mercapto, carbonyl, carboxy, amino, ketone, and mercapto groups. Spacer groups may also be used in combination. When a combination of spacer groups is used, the spacer groups may be different or equivalent.

Preferred spacer groups include, for example, 6-aminohexanol, 6-mercaptohexanol, 10-hydroxydecanoic acid, glycine and other amino acids, 1,6-hexanediol, .beta.-alanine, 2-aminoethanol, cysteamine (2-aminoethanethiol), 5-aminopentanoic acid, 6-aminohexanoic acid, 3-maleimidobenzoic acid, phthalide, .alpha.-substituted phthalides, the carbonyl group, aminal esters, and the like.

The spacer can serve to introduce additional molecular mass and chemical functionality into the agent-dendrimer complex. Generally, the additional mass and functionality will affect the serum half-life and other properties of the agent-dendrimer complex. Thus, through careful selection of spacer groups, agent-dendrimer complexes with a range of serum half-lives can be produced.

Whether coupled directly, or through a spacer, the agent is preferably coupled to the dendrimer via a covalent bond. The covalent bond may be non-reversible, partially reversible, or fully reversible. The degree of reversibility corresponds to the susceptibility of the agent-dendrimer complex to in vivo degradation. As will be apparent to those of skill in the art, such reversible groups can be incorporated at any point within the dendrimer-agent conjugate. The introduction of a spacer arm having a reversible linkage is merely an exemplary embodiment; the bond between the agent and the dendrimer, for example, may also be reversible.

In a preferred embodiment, the bond is reversible (e.g., easily hydrolyzed) or partially reversible (e.g., partially or slowly hydrolyzed). Cleavage of the bond can occur through biological or physiological processes. In other embodiments, the physiological processes will cleave bonds at other locations within the complex (e.g., removing an ester group or other protecting group that is coupled to an otherwise sensitive chemical functionality) before cleaving the bond between the agent and dendrimer, resulting in partially degraded complexes. Other cleavages can also occur, for example, between the spacer and agent and the spacer and dendrimer.

For rapid degradation of the complex after administration, circulating enzymes in the plasma can be used to cleave the dendrimer from the pharmaceutical agent. These enzymes can include non-specific aminopeptidases and esterases, dipeptidyl carboxy peptidases, proteases of the blood clotting cascade, and the like.

Alternatively, cleavage may be brought about by nonenzymatic processes. For example, chemical hydrolysis may be initiated by differences in pH experienced by the complex following delivery. In such a case, the pharmaceutical agent-dendrimer complex may be characterized by a high degree of chemical lability at physiological pH of 7.4, while exhibiting higher stability at an acidic or basic pH in the reservoir of the delivery device. An exemplary pharmaceutical agent-dendrimer complex, which is cleaved in such a process is a complex incorporating a N-Mannich base linkage within its framework.

In most cases, cleavage of the complex will occur during or shortly after administration. However, in preferred embodiments, cleavage does not occur until the complex reaches the pharmaceutical agent's site of action. Furthermore, in some cases, particularly with peptide and protein drugs produced via recombinant expression techniques, one may not desire cleavage of the complex.

The susceptibility of the agent-dendrimer complexes to degradation can be ascertained through studies of the hydrolytic or enzymatic conversion of the complex to the unbound pharmaceutical agent. Generally, good correlation between in vitro and in vivo activity is found using this method. See, e.g., Phipps et al., *J. Pharm. Sciences* 78:365 (1989). The rates of conversion may be readily determined, for example by spectrophotometric methods or by gas-liquid or high pressure liquid chromatography. Half-lives and other kinetic parameters may then be calculated using standard techniques. See, e.g., Lowry et al. MECHANISM AND THEORY IN ORGANIC CHEMISTRY, 2nd Ed., Harper & Row, Publishers, New York (1981).

In an illustrative embodiment, the dendritic PEO hybrid is modified as a drug carrier in which the hydroxyl functional end groups of 18 are modified in order to enable the coupling of a drug moiety. An exemplary drug molecule for conjugation to the dendrimer is the anticancer drug doxorubicin, however, many other drugs, ligands, chromophores, peptides sugars, proteins, DNA and similar bioactive compounds can also be coupled to these hydroxyl functionalized dendritic PEO hybrids either directly or using appropriate functionalization chemistry on 18 and analogs. As outlined in FIG. 2, the hydroxyl chain ends of 18 are reacted with 4-nitrophenyl chloroformate affording the corresponding 4-nitrophenyl carbonate 19 in a high yield after precipitation. Subsequently 19 is reacted with tert-butyl carbazate, using DMAP as a catalyst, yielding a BOC protected dodecahydrazide 20. After exposure to trifluoroacetic acid (TFA) all BOC protective groups were removed and the corresponding hydrazide functional aliphatic ester PEO hybrid 21 is obtained. Doxorubicin is coupled to the hydrazide functional drug carrier via hydrazone linkage by stirring in methanol using TFA as a catalyst. After purification using a LX-20 Sephadex resin the drug conjugate was isolated as a red powder. The drug payload determined can be determined by any method, e.g., UV-measurement. The drug payload is preferably about 20 weight %. In the representative embodiment, set forth above, the drug-modified macromolecule is water soluble in spite of the high loading of the water-insoluble drug moiety.

Using higher generation dendrimers the drug loading can be adjusted further while solubility can also be adjusted by changing the molecular weight of the PEO core. A higher loading of drug is compensated by the use of a higher molecular weight of the PEO core. Standard in vitro experiments using the doxorubicin modified PEO dendrimer showed that the bound drug had little toxicity at physiological pH when compared to free doxorubicin, but that release of the toxic drug from the dendrimer carrier could be achieved with certain types of cancer cells over a period of 72 h. In this example, release of the drug occurs via a hydrolysis reaction that is known to be highly pH sensitive.

Pharmaceutical Formulations

In another preferred embodiment, the present invention provides a pharmaceutical formulation comprising a dendrimer-agent conjugate and a pharmaceutically acceptable carrier.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); anti-arrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the dendrimer with a solid excipient, optionally grinding the resulting mixture, and processing the mixture of granules, after adding suitable auxiliaries, if desired, to obtain tablets or dragee cores. Suitable excipients are, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, poly(ethylene oxide), and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as poly(ethylene oxide).

In an exemplary embodiment, the therapeutic agent includes a carbonyl moiety, such as doxorubicin. In this embodiment, the hydroxyl groups of the parent dendrimer are converted to a hydrazide derivative such as that shown below:

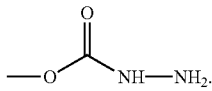

The carbonyl-containing therapeutic moiety is coupled to the dendrimer by reaction with the hydrazide to form a conjugate having a general structure, such as that shown below.

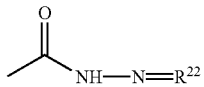

$R^{22}$ is the therapeutic agent. One of skill in the art will appreciate that the above-described conjugation scheme is not exclusive to therapeutic agents and that it is equally applicable to other agents such as diagnostic agents and analytical agents.

In a still further embodiment, the present invention provides a biological compartment having localized therein a dendrimer of any structure according to the invention. Thus, the dendrimer localized within the biological compartment can be, for example, a first, second, third or higher generation species. Representative biological compartments into which the dendrimers of the invention distribute include, but are not limited to, cells and organelles.

The localization of a dendrimer of the invention can be detected by any method known in the art for detecting the presence of an exogenous molecule in a biological compartment. An exemplary detection means relies upon confocal microscopy to detect the presence of a fluorescent dendrimer of the invention within a biological compartment. Other methods of detecting the presence of a dendrimer of the invention within a cellular compartment will be apparent to those of skill in the art.

The Methods

In another aspect, the present invention provides a method of producing a dendrimer, which is substantially free of coupling reagent derived (e.g., dicycloxylcarbodiimide-derived) side products. The method includes contacting the core moiety with an anhydride. The anhydride is formed from a carboxylic acid, which has the structure desired for the subunits of a particular generation of the dendrimer of the invention.

Using the method of the present invention, one can prepare a population of dendrimer molecules of a selected generation, in which less than about 10% of the individual dendrimer molecules in the population include a flaw. Preferably, the method of the invention provides a dendrimer population in which less than about 5%, more preferably less than about 2%, even more preferably less than about 1% of the individual molecules include a flaw. As used herein, the term "flaw" refers to the failure of a reactive functional group on the growing dendrimer to react with an incoming anhydride, thereby resulting in an absence of one or more generations pendent from the non-reacting locus.

Moreover, the method of the invention produces dendrimers that are highly pure, being substantially free of coupling reagent derived side product. For example, unlike those produced by previous methods, the dendrimers of the present invention are generally crystalline solids. The coupling reagent side product preferably accounts for no more than from about 5% to about 0.01%, more preferably from about 1% to about 0.1% of the dendrimer composition. Exemplary coupling reagent derived side products include, but are not limited to, dicyclohexyl urea and N-acyl urea.

In an exemplary embodiment, the method provides for the preparation of a dendrimer having a subunit with the structure:

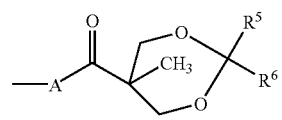

wherein A is an active group residue selected from NH, O, and S on a core moiety. The symbols $R^5$ and $R^6$ represent components of a diol protecting group and are members independently selected from H, substituted or unsubstituted alkyl, substituted or unsubstituted heteroalkyl and substituted or unsubstituted aryl, with the proviso that when $R^5$ is H, $R^6$ is other than H.

The method includes, (a) forming a reaction mixture by contacting a core moiety comprising a reactive functional group, A, with an acylating group in an organic solvent. The acylating group has the structure:

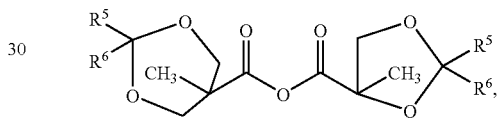

thereby acylating A, and forming the dendrimer. The mixture produced in step (a) is preferably extracted with an aqueous solution, thereby removing impurities. In a preferred embodiment, the acylating agent is a solid that is substantially free of coupling reagent derived side products.

A further preferred embodiment provides for the preparation of the deprotected dendrimer. The method comprises, removing the diol protecting group from the dendrimer formed in step (a), to form a first generation dendrimer comprising a subunit having the structure:

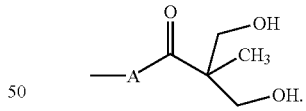

The dendrimers, which include the subunit set forth above are preferably of sufficient purity that they are isolated as solids.

In other preferred embodiments, the steps of acylating the growing dendrimer with additional portions of acylating agent, followed by deprotection allows a dendrimer of the invention of essentially any generation to be assembled.

Referring to FIG. 1, in a preferred divergent procedure for the preparation of aliphatic ester dendrimers, the benzylidene protected anhydride 2, the core molecule 1,1,1-tris (hydroxyphenyl)ethane and DMAP are dissolved in a solvent, e.g., pyridine. After stirring at room temperature for a selected time, the excess anhydride is quenched by adding a small amount of water. After extractive work-up with; $NaHSO_4$, $Na_2CO_3$ and brine, a high yield of the first generation dendrimer 3 is obtained. The divergent growth is easily monitored by either Size Exclusion Chromatography (SEC) or Matrix Assisted Laser Desorption Ionization Time of Flight Mass Spectroscopy (MALDI). Removal of the benzylidene protective group of 3 by hydrogenolysis affords the corresponding hydroxyl functional dendrimer 5 in essentially quantitative yield. According to the preferred general procedure for the preparation of esters and removal of the benzylidene protective group, aliphatic ester dendrimers up the sixth generation 13 with a molecular weight of 30,718 Da. are readily prepared in high yields and purity. Other methods for the removal of the protecting groups include controlled acid hydrolysis, though best yields and purity were obtained using the preferred procedure.

Although the above discussion focuses on the preparation of dendrimers of the invention up to the third generation, it will be apparent to those of skill in the art that the process described above can be repeated any desired number of times to produce a dendrimer of any desired generation. Moreover, the structure of the anhydride can be varied from generation to generation. Alternatively, a mixture of anhydrides can be used to form a generation having a mixed structure.

The materials, methods and devices of the present invention are further illustrated by the examples, which follow. These examples are offered to illustrate, but not to limit the claimed invention.

EXAMPLES

In the following examples the dendrimers will be designated by the structure number N as well as a short hand notation $[Gx]-(F)_n$ in which [Gx] is used to designate the generation number (with x=1, 2, 3, etc) and F is a short hand descriptor of the functional group at the chain ends of the dendrimer (e.g. Bn=benzylidene, OH=hydroxyl) and n is the number of functional groups F in the dendrimer.

Example 1

1.1 Preparation of the benzylidene derivative of bis-MPA: Benzylidene-2,2-bis(methoxy)propanoic Acid (Compound 1)

Bis-MPA 20.00 g (149.11 mmol) and 34.04 g (222.67 mmol) benzaldehyde dimethyl acetal and 1.42 g (7.46 mmol)p-toluenesulfonic acid monohydrate (TsOH) were mixed in 150 mL acetone. The reaction mixture was stirred for 4 h at room temperature. After storage of the reaction mixture in the refrigerator over night the solids were filtered off and washed with cold acetone to give 1 as white crystals: 21.0 g, (64%), Characterization: IR (cm$^{-1}$, thin film from CHCl$_3$): 3400–2300 (br), 1699 (s). $^1$H-NMR (500 MHz, CDCl$_3$): δ 1.11 (s, 3), 3.70 (d, 2, J=11.7), 4.63 (d, 2, J=11.4), 5.49 (s, 1), 7.37 (m, 3), 7.48 (m, 2). $^{13}$C-NMR (500 MHz, CDCl$_3$): δ 17.58, 41.58, 72.65, 100.37, 126.10, 128.01, 128.70, 138.39, 175.58. Mass spectrometry, calculated: [M]$^+$ m/z=222.24; found: TOF MS ES: [M+Na]$^+$=245.10. Elemental analysis, calculated for $C_{12}H_{14}O_4$: C, 64.85; H, 6.35; O, 28.80. Found: C, 64.89; H, 6.52.

1.2 Preparation of the anhydride of benzylidene bis-MPA: Benzylidene-2,2-bis(methoxy)propanoic Anhydride (compound 2)

Benzylidene-2,2-bis(methoxy)propanoic Acid (Compound 1) 20.00 g (90.00 mmol) and 10.21 g (49.50 mmol) N,N'-dicyclohexylcarbodiimide (DCC) were mixed in 100 mL CH$_2$Cl$_2$. The reaction mixture was stirred over night at room temperature. The precipitated DCC-urea was filtered off in a glass filter and washed with a small volume of CH$_2$Cl$_2$. The crude product was purified by precipitating the CH$_2$Cl$_2$ solution into 1000 mL of hexane under vigorous stirring. After filtration anhydride 2 was isolated as white crystals: 17.1 g, (89%) Additional purification by recrystallization affords a product in which no impurities resulting from the presence of DCC by-products can be detected. All analytical data (elemental and spectroscopic) for this compound matched those expected for the assigned structure: IR (cm$^{-1}$, thin film from CHCl$_3$): 3050, 1814 (s), 1746 (s). $^1$H-NMR (300 MHz, CDCl$_3$): δ 1.12 (s, 6), 3.69 (d, 4, J=10.5), 4.66 (d, 4, J=10.5), 5.47 (s, 2), 7.35 (m, 6), 7.45 (m, 4). $^{13}$C-NMR (400 MHz, CDCl$_3$): δ 16.85, 44.18, 73.17, 102.11, 126.27, 128.22, 129.09, 137.56, 169.12. Mass spectrometry, calculated: [M]$^+$ m/z=426.46; found: TOF MS ES: [M+Na]$^+$=449.20. Elemental analysis, calculated for $C_{24}H_{26}O_7$: C, 67.59; H, 6.15; found: C, 67.37; H, 6.30, no trace of nitrogen could be detected.

Example 2

2.1 Preparation of generation 1 $[G1]-(Bn)_3$ (compound 3) and description of a general esterification procedure by anhydride coupling 1,1,1-Tris(hydroxyphenyl)ethane 100 mg (326 μmol) and 20 mg (160 μmol) 4-(dimethylamino)pyridine (DMAP) were dissolved in 4 mL dry pyridine. 556 mg (1.31 mmol) benzylidene-2,2-bis(methoxy)propanoic anhydride (compound 2) was added as a solid to the pyridine solution. The reaction mixture was stirred at room temperature for 20 h. After complete reaction according to MALDI-TOF the excess anhydride (2) was quenched by stirring the reaction mixture with 0.5 mL H$_2$O for 4 h. The organic phase was diluted with 80 mL CHCl$_3$ and extracted two portions of (40 mL) NaHSO$_4$ (1M), two portions of (40 mL) Na$_2$CO$_3$ (10%) and one portion of (40 mL) brine. The organic phase was dried with MgSO$_4$ and evaporated to give 3 as a white solid: 292 mg, (97%). Spectroscopic characterization of the compound by techniques such as NMR and MALDI confirmed its purity and structure: IR (cm$^{-1}$, thin film from CHCl$_3$): 3036, 1755 (s). $^1$H-NMR (300 MHz, CDCl$_3$): δ 1.21 (s, 9), 2.17 (s, 3), 3.75 (d, 6, J=11.4), 4.78 (d, 6, J=11.4), 5.52 (s, 3), 7.04 (d, 6, J=8.7), 7.11 (d, 6, J=9.0), 7.35 (m, 9), 7.46 (m, 6). $^{13}$C-NMR (500 MHz, CDCl$_3$): δ 17.67, 30.84, 42.85, 51.58, 73.50, 101.99, 120.83, 126.20, 128.25, 129.04, 129.62, 137.73, 146.12, 149.03, 172.69. Mass spectrometry, calculated: [M]$^+$ m/z=919.03; found: TOF MS ES: [M+Na]$^+$ =941.56, MALDI-TOF MS [M+Ag]$^+$=1033. Elemental analysis, calculated for $C_{56}H_{54}O_{12}$: C, 73.19; H, 5.92; found: C, 72.91; H, 5.95.

2.2 Preparation of $[G1]-(OH)_6$ (compound 4) and a General Procedure for Removal of the Benzylidene Group $[G1]-(Bn)_3$ (compound 3) 268 mg (292 μmol) was dissolved in 10 mL CHCl$_3$ and then diluted with 10 mL methanol. 50 mg Pd/C (10%) was added to the solution. The apparatus for catalytic hydrogenolysis was evacuated from air and filled H$_2$ three times. After vigorous stirring over night the catalyst was filtered off in a glass filter and carefully washed with methanol. The filtrate was evaporated to give 4 as white crystals: 185 mg, (97%). All analytical data for this compound matched those expected for the assigned structure: IR (cm$^{-1}$, thin film from THF): 3369 (br), 1744 (s). $^1$H-NMR (300 MHz, d$_6$-DMSO): δ 1.18 (s, 9), 2.14 (s, 3), 3.53 (dd, 6, J=10.5, 5.4), 3.65 (dd, 6, J=10.5, 5.4), 4.92 (t, 6, J=10.8), 7.04 (q, 12, J=18.9, 8.7). $^{13}$C-NMR (500 MHz, d$_6$-DMSO): δ 16.92, 30.42, 50.88, 51.27, 64.00, 121.32, 129.17, 145.77, 149.00, 173.63. Mass spectrometry, calcd.: [M]$^+$ m/z=654.71. Found: TOF MS ES: [M+Na]$^+$=677.43. Elemental Anal. Calcd for $C_{35}H_{42}O_{12}$: C, 64.21; H, 6.47. Found: C, 64.12; H, 6.39.

2.3 Preparation of [G2]-(Bn)$_6$ (compound 5)

[G#1]-(OH)$_6$ (4) 328 mg (500 µmol) and 122 mg (1 mmol) 4-(dimethylamino)pyridine (DMAP) were dissolved in 2 mL dry pyridine and then diluted with 6 mL of CH$_2$Cl$_2$. It was followed by the addition of 1.71 g (4.00 mmol) of anhydride (2) as a solid to the reaction mixture. The reaction mixture was stirred at room temperature for 5 h. The excess of anhydride (2) was quenched by stirring the reaction mixture with 2 mL of a 1:1 pyridine/water solution over night. The organic phase was diluted with 100 mL CH$_2$Cl$_2$ and extracted with 2×40 mL NaHSO$_4$ (1M), 2×40 mL Na$_2$CO$_3$ (10%) and 1×40 mL brine. The organic phase was dried with MgSO$_4$ and evaporated to give 5 as a white solid material: 850 mg, (90%). Characterization: IR(cm$^{-1}$, thin film from CHCl$_3$): 3050, 1741 (s). $^1$H-NMR (300 MHz, CDCl$_3$): δ 0.98 (s, 18), 1.42 (s, 9), 1.97 (s, 3), 3.63 (d, 12, J=11.5), 4.52 (s, 12), 4.63 (d, 12, J=11.5), 5.43 (s, 6), 6.80 (d, 6, J=8.9), 6.88 (d, 6, J=8.9), 7.25 (m, 18), 7.39 (m, 12). $^{13}$C-NMR (500 MHz, CDCl$_3$): δ 17.72, 17.17, 42.65, 47.06, 51.39, 65.60, 73.42, 73.49, 101.77, 120.76, 126.11, 128.08, 128.83, 129.55, 137.62, 146.11, 148.45, 171.41, 173.29. Mass spectrometry, calculated.: [M]$^+$ m/z=1880.06; found: MALDI-TOF: [M+Ag]$^+$=1984. Elemental analysis, calculated for C$_{107}$H$_{114}$O$_{30}$: C, 68.36; H, 6.11. Found: C, 68.39; H, 6.26.

2.4 Preparation of 2.4 [G2]-OH$_{12}$ (compound 6)

[G#2]-(Bn)$_6$ (compound 5) (778 mg, 410 µmol) was dissolved in 20 mL of CH$_2$Cl$_2$ and then diluted with 20 mL methanol. 50 mg Pd/C (10%) was added to the solution. The apparatus for catalytic hydrogenolysis was evacuated from air and filled with H$_2$ three times. After vigorous stirring overnight the catalyst was filtered off in a glass filter and carefully washed with methanol. The filtrate was evaporated to give 6 as a white amorphous solid material: 544 mg, (97%). Characterization, IR (cm$^{-1}$, thin film from THF): 3416 (br), 1734 (s). $^1$H-NMR (500 MHz, d$_6$-DMSO): δ 1.09 (s, 18), 1.33 (s, 9), 2.17 (s, 3), 3.44 (d, 12, J=8.5), 3.50 (d, 12, J=10.5), 4.26 (dd, 12, J=22.8, 10.5), 7.11 (m, 12). $^{13}$C-NMR (500 MHz, d$_6$-DMSO): δ 16.83, 17.16, 46.73, 50.49, 51.35, 63.87, 65.17, 121.28, 129.40, 146.21, 148.55, 171.50, 174.23. Mass spectrometry, calculated: [M]$^+$ m/z=1351.41. Found: TOF MS ES: [M+Na]$^+$=1374.61, [M+Na]$^{+2}$=698.28. MALDI-TOF: [M+Ag]$^+$=1447. Elemental analysis, calculated for C$_{65}$H$_{90}$O$_{30}$: C, 57.77; H, 6.71. Found: C, 57.52; H, 6.86.

2.5 Preparation of [G3]-(BN)$_{12}$ (compound 7)

[G#2]-(OH)$_{12}$ (compound 6) (426 mg, 315 µmol) and 154 mg (1.26 mmol) of 4-(dimethylamino)pyridine (DMAP) were dissolved in 3 mL of dry pyridine and then diluted with 6 mL of CH$_2$Cl$_2$. 2.15 g (5.04 mmol) of benzylidene-2,2-bis(methoxy)propanoic anhydride (2) was added as a solid to the reaction mixture. The reaction mixture was stirred at room temperature for 5 h. The excess anhydride (2) was quenched by stirring the reaction mixture with 2 mL of a 1:1 pyridine/water solution overnight. The organic phase was diluted with 100 mL CH$_2$Cl$_2$ and extracted with 2×40 mL NaHSO$_4$ (1M), 2×40 mL Na$_2$CO$_3$ (10%) and 1×40 mL brine. The organic phase was dried with MgSO$_4$ and reduced to approximately 10 mL and precipitated into 200 mL of hexane under vigorous stirring. After decantation the precipitate was re-dissolved in CH$_2$Cl$_2$ and evaporated to give 7 as a white amorphous solid material: 1100 mg, (92%). Characterization, IR (cm$^{-1}$, thin film from CHCl$_3$): 3048, 1742 (s). $^1$H-NMR (300 MHz, CDCl$_3$): δ 0.89 (s, 36), 1.12 (s, 9), 1.22 (s, 18), 2.04 (s, 3), 3.55 (d, 24, J=11.7), 4.15 (dd, 12, J=18.2, 11.2), 4.37 (s, 24), 4.54 (d, 24, J=11.4), 5.38 (s, 12), 6.90 (d, 6, J=9), 7.03 (d, 6, J=9), 7.27 (m, 36), 7.39 (m, 24). $^{13}$C-NMR (500 MHz, CDCl$_3$): δ 14.09, 17.28, 17.61, 17.69, 22.62, 25.24, 31.55, 34.63, 42.53, 46.79, 46.89, 65.13, 65.61, 73.39, 73.46, 101.61, 120.73, 126.13, 128.08, 128.81, 129.68, 137.79, 146.23, 148.49, 170.80, 171.89, 173.17. Mass spectrometry, calculated.: [M]$^+$ m/z=3802.11. Found: MALDI-TOF: [M+Ag]$^+$=3901. Elemental analysis, calculated for C$_{209}$H$_{234}$O$_{66}$: C, 66.02; H, 6.20. Found: C, 66.02; H, 6.39.

2.6 Preparation of [G3]-(OH)$_{24}$ (compound 8)

[G#3]-(Bn)$_{12}$ (7) (942 mg, 248 µmol) was dissolved in 20 mL of CH$_2$Cl$_2$ and then diluted with 20 mL methanol. 50 mg Pd/C (10%) was added to the solution. The apparatus for catalytic hydrogenolysis was evacuated from air and filled H$_2$ three times. After vigorous stirring overnight the catalyst was filtered off in a glass filter and carefully washed with methanol. The filtrate was evaporated to give 8 as a white amorphous solid: 637 mg, (94%). IR (cm$^{-1}$, thin film from THF): 3424 (br), 1732 (s). $^1$H-NMR (500 MHz, d$_6$-DMSO): δ 0.99 (s, 36), 1.19 (s, 18), 1.37 (s, 9), 2.15 (s, 3), 3.42 (m, 24), 4.14 (m, 24), 4.35 (dd, 12, J=26.5, 11), 4.65 (t, 24, J=5.5), 7.05 (d, 6, J=9), 7.12 (d, 6, J=9). $^{13}$C-NMR (500 MHz, d$_6$-DMSO): δ 16.75, 17.03, 17.22, 46.42, 46.60, 50.33, 63.73, 64.60, 65.89, 121.05, 129.49, 146.24, 148.35, 170.98, 171.95, 174.13. Calcd.: [M]$^+$ m/z=2744.81. Found: TOF MS ES: [M+Na]$^+$=2,767.30, [M+Na]$^{+2}$=1,395.23. Elemental analysis, calculated for C$_{125}$H$_{186}$O$_{66}$: C, 54.70; H, 6.83. Found: C, 54.68; H, 7.02.

2.7 Preparation of [G4]-(Bn)$_{24}$ (compound 9)

[G3]-(OH)$_{24}$ (8) (443 mg, 161 µmol) and 157 mg (1.29 mmol) 4-(dimethylamino)pyridine (DMAP) were dissolved in 3 mL of dry pyridine. The mixture was diluted with 6 mL of CH$_2$Cl$_2$, followed by the addition of 2.20 g (5.04 mmol) of benzylidene-2,2-bis(methoxy)propanoic anhydride (2) as a solid. The reaction mixture was stirred at room temperature for 7 h. The excess of (2) was quenched by stirring the reaction mixture with 2 mL of a 1:1 pyridine/water solution overnight. The organic phase was diluted with 100 mL CH$_2$Cl$_2$ and extracted with 2×40 mL NaHSO$_4$ (1cM), 2×40 mL Na$_2$CO$_3$ (10%) and 1×40 mL brine. The organic phase was dried with MgSO$_4$ and reduced to approximately 10 mL and precipitated into 200 mL of hexane under vigorous stirring. After decantation the precipitate was re-dissolved in CH$_2$Cl$_2$ and evaporated to give 9 as a white solid: 1150 mg, (93%). IR (cm$^{-1}$, thin film from CHCl$_3$): 3047, 1741 (s). $^1$H-NMR (300 MHz, CDCl$_3$): δ 0.89 (s, 72), 1.01 (s, 18), 1.17 (s, 36), 1.25 (s, 9), 2.06 (s, 3), 3.52 (d, 48, J=10.8), 4.07 (m, 24), 4.32 (m, 60), 4.52 (d, 48, J=11.4), 5.35 (s, 24), 6.92 (d, 6, J=8.4), 7.07 (d, 6, J=8.7), 7.26 (m, 72), 7.36 (m, 48). $^{13}$C-NMR (500 MHz, CDCl$_3$): δ 17.24, 17.44, 17.63, 17.66, 42.51, 46.49, 46.82, 46.85, 65.01, 65.27, 65.60, 73.36, 73.41, 101.58, 120.77, 126.17, 128.09, 128.82, 137.86, 146.36, 148.55, 170.71, 171.44, 171.85, 173.17. Mass spectrometry, calculated [M]$^+$ m/z=7,646.22. Found: MALDI-TOF [M+Ag]$^+$=7,742. Elemental analysis, calculated for C$_{413}$H$_{474}$O$_{138}$: C, 64.88; H, 6.25. Found: C, 65.05; H, 6.40.

2.8 Preparation of [G4]-(OH)$_{48}$ (compound 10)

[G#4]-(Bn)$_{12}$ (9) (760 mg, 99.4 µmol) was dissolved in 20 mL of CH$_2$Cl$_2$ and then diluted with 20 mL of methanol. 50 mg Pd/C (10%) was added to the solution. The apparatus for catalytic hydrogenolysis was evacuated from air and filled H$_2$ three times. After vigorous stirring overnight the catalyst was filtered off in a glass filter and carefully washed with methanol. The filtrate was evaporated to give 10 as a white solid material: 522 mg, (95%). IR (cm$^{-1}$, thin film from THF): 3439 (br), 1736 (s). $^1$H-NMR (500 MHz, d$_6$-DMSO): δ 0.97 (s, 72), 1.12 (s, 36), 1.18 (s, 18), 1.35 (s, 9), 2.14 (s, 3), 3.44 (m, 48), 4.08 (m, 48), 4.22 (m, 24), 4.36 (dd, 12, J=24.5, 10.0), 4.63 (t, 48, J=5.5), 7.05 (d, 6, J=8.0), 7.12 (d, 6, J=7.5). $^{13}$C-NMR (500 MHz, d$_6$-DMSO): δ 16.73, 16.97, 17.18, 46.27, 46.56, 50.26, 63.69, 64.37, 65.28, 65.56, 121.02, 129.48, 146.25, 148.29, 170.80, 171.49, 171.88, 174.08. Calcd.: [M]$^+$ m/z=5,531.61. Found: TOF MS ES: [M+Na]$^+$=5,553.58, [M+Na]$^{+2}$=2,788.54, [M+Na]$^+$$_3$=1866.94. Anal. Calcd for C$_{245}$H$_{378}$O$_{138}$: C, 53.20; H, 6.89. Found: C, 53.06; H, 7.06.

2.9 Preparation of [G5]-(Bn)$_{48}$ (compound 11)

[G#4]-OH)$_{48}$ (10) (391 mg, 70.7 µmol) and 172 mg (1.41 mmol) 4-(dimethylamino)pyridine (DMAP) were dissolved in 3 mL of dry pyridine and then diluted with 6 mL of CH$_2$Cl$_2$. 1.95 g (4.59 mmol) of benzylidene-2,2-bis(methoxy)propanoic anhydride (2) was added as a solid to the reaction mixture. The reaction mixture was stirred at room temperature for 7 h. The excess anhydride (2) was quenched by stirring the reaction mixture with 2 mL of a pyridine/water solution (1:1) overnight. The organic phase was diluted with 100 mL CH$_2$Cl$_2$ and extracted with 2×40 mL NaHSO$_4$ (1M), 2×40 mL Na$_2$CO$_3$ (10%) and 1×40 mL Brine. The organic phase dried with MgSO$_4$ and reduced to approximately 10 mL and precipitated into 200 mL of hexane under vigorous stirring. After decantation the precipitate was re-dissolved in CH$_2$Cl$_2$ and evaporated to give 11 as a white solid: 972 mg, (90%). IR (cm$^{-1}$, thin film from CHCl$_3$): 3050, 1738 (s). $^1$H-NMR (500 MHz, CDCl$_3$): δ 0.83 (s, 144), 1.00 (s, 36), 1.15 (s, 90), 1.34 (s, 9), 2.01 (s, 3), 3.49 (d, 96, J=10.5), 4.06 (m, 60), 4.31 (m, 120), 4.49 (d, 96, J=10.5), 5.32 (s, 48), 6.95 (d, 6, J=7), 7.06 (d, 6, J=7), 7.24 (m, 144), 7.36 (m, 96). $^{13}$C-NMR (500 MHz, CDCl$_3$): δ 17.25, 17.47, 17.60, 17.65, 42.47, 46.41, 46.48, 46.76, 47.00, 51.72, 64.93, 73.29, 73.34, 101.52, 120.81, 126.18, 128.07, 128.80, 137.93, 146.37, 148.65, 170.65, 171.41, 171.83, 173.15. Calcd.: [M]$^+$ m/z=15,334.29. Found: MALDI-TOF MS: [M+Ag]$^+$=15,518. Anal. Calcd for C$_{821}$H$_{954}$O$_{282}$: C, 64.31; H, 6.27. Found: C, 63.12; H, 6.24.

2.10 Preparation of [G5]-(OH)$_{96}$ compound 12)

[G#5]-(Bn)$_{48}$ (11) (300 mg, 19.6 µmol) was dissolved in 20 mL of CH$_2$Cl$_2$ and then diluted with 20 mL methanol. 50 mg Pd/C (10%) was added to the solution. The apparatus for catalytic hydrogenolysis was evacuated from air and filled H$_2$ three times. After vigorous stirring overnight the catalyst was filtered off in a glass filter and carefully washed with methanol. The filtrate was evaporated to give 12 as a white solid: 200 mg, (92%). IR (cm$^{-1}$, thin film from THF): 3419 (br), 1734 (s). $^1$H-NMR (300 MHz, d$_6$-DMSO): δ 0.97 (s, 144), 1.13 (s, 108), 1.21 (s, 18), 1.35 (s, 9), 2.11 (s, 3), 3.40 (m, 192), 4.05 (m, 180), 4.56 (m, 96), 7.04 (d, 6, J=7), 7.10 (d, 6, J=7). $^{13}$C-NMR (500 MHz, d$_6$-DMSO): δ 16.80, 17.05, 17.29, 46.23, 46.28, 50.29, 63.74, 64.00, 64.35, 65.04, 121.13, 129.52, 146.34, 148.39, 170.79, 171.50, 171.95, 174.15. Calcd.: [M]$^+$ m/z=11,105.07. Found: TOF MS ES: [M+Na]$^{+2}$=5,571.71, [M+Na]$^{+3}$=3,724.09, [M+Na]$^{+4}$=2,799.73. Anal. Calcd for C$_{485}$H$_{762}$O$_{282}$: C, 52.45; H, 6.92. Found: C, 51.42; H, 6.94.

2.11 [G6]-(Bn)$_{96}$ (compound 13)

[G#5]-(OH)$_{96}$ (12) (402 mg, 36.2 µmol) and 132 mg (1.09 mmol) of 4-(dimethylamino)pyridine (DMAP) were dissolved in 3 mL dry pyridine and then diluted with 6 mL of CH$_2$Cl$_2$. 1.85 g (4.34 mmol) of benzylidene-2,2-bis(methoxy)propanoic anhydride (2) was added as a solid to the reaction mixture. The reaction mixture was stirred at room temperature overnight and the excess anhydride (2) was quenched by stirring the reaction mixture with 2 mL of a pyridine/water solution (1:1) overnight. The organic phase was diluted with 100 mL CH$_2$Cl$_2$ and extracted with 2×40 mL NaHSO$_4$ (1M), 2×40 mL Na$_2$CO$_3$ (10%) and 1×40 mL Brine. The organic phase was dried with MgSO$_4$ and reduced to approximately 10 mL and precipitated into 200 mL of hexane under vigorous stirring. After decantation the precipitate was re-dissolved in CH$_2$Cl$_2$ and evaporated to give 13 as a white amorphous solid: 800 mg, (92%). IR (cm$^{-1}$, thin film from CHCl$_3$): 3051, 1741 (s). $^1$H-NMR (500 MHz, CDCl$_3$): δ 0.79 (s, 288), 0.99 (s, 72), 1.12 (s, 144), 1.23 (s, 18), 1.36 (s, 9), 1.92 (s, 3), 3.42 (d, 192, J=10.5), 4.05 (m, 132), 4.28 (m, 240), 4.44 (d, 192, J=10.5), 5.28 (s, 96), 6.93 (d, 6, J=7), 7.00 (d, 6, J=7), 7.23 (m, 288), 7.34 (m, 192). $^{13}$C-NMR (500 MHz, CDCl$_3$): δ 17.25, 17.54, 17.64, 42.41, 46.34, 46.69, 64.81, 73.22, 101.41, 126.20, 128.04, 128.76, 138.00, 171.43, 171.81, 173.12. Calcd.: [M]$^+$ m/z=30,710.56. Found: MALDI-TOF MS: [M+Ag]$^+$=30,783. Anal. Calcd for C$_{1637}$H$_{1914}$O$_{570}$: C, 64.02; H, 6.28. Found: C, 63.86; H, 6.13.

As will be apparent to those of skill in the art, in each of the above-recited procedures, the benzylidene anhydride can be replaced by the analogous isopropylidene analog, the preparation of a representative example of which is set forth below.

2.12 Preparation of the isopropylidene ketal of bis-MPA anhydride: isopropylidene-2,2-bis(methoxy)propanoic anhydride A suspension of 10.0 g (57.4 mmol, 2.0 equiv.) of the isopropylidene ketal of bis-MPA, isopropylidene-2,2-bis(methoxy)propanoic acid, compound 14 (itself prepared according to the procedure described by Ihre, H.; Hult, A.; Frechet, J. M. J. and Gitsov, I. in *Macromolecules* 1998, 31, 4061–4068) in 30 mL of dichloromethane was treated with a solution of DCC (5.92 g, 28.7 mmol, 1.0 equiv.) in 10 mL of dichloromethane. The reaction mixture was stirred at room temperature for 4 hours. The urea DCC by-product (DCU) was filtered off in a glass filter and was washed with a small amount of dichloromethane. Hexane (20 mL) was added to the filtrate to precipitate more DCU and the resulting suspension was filtered through a glass filter. The organic phase was evaporated to give 9.23 g (97%) of the anhydride as a viscous oil. Following further purification to remove all traces of DCC by-products, the product is obtained as a white amorphous solid. Characterization: IR (cm$^{-1}$, thin film): 1815 (s), 1746 (s). $^1$H NMR (500 MHz, CDCl$_3$): δ 1.19 (s, 3), 1.35 (s, 3), 1.40 (s, 3), 3.65 (d, 2, J=12.0), 4.16 (d, 2, J=12.0). $^{13}$C NMR (CDCl$_3$): δ 17.71, 21.59, 25.70, 43.75, 65.75, 98.45, 169.59. Mass spectrometry, calculated: [M+H]$^+$ (C$_{16}$H$_{27}$O$_7$) m/z=331.1756. Found: FABHR-MS: [M+H]$^+$ m/z=331.1747. Elemental Analysis: Calculated. for C$_9$H$_{26}$O$_7$: C, 58.2;, H, 7.93. Found: C, 58.6; H, 7.76. No nitrogen was detected by elemental analysis.

Example 3

3.1 Preparation of the isopropylidene ketal of bis-MPA: Isopropylidene-2,2-bis(methoxy)propanoic Acid (compound 14)

Bis-MPA 10.00 g (74.55 mmol) and 13.8 ml (111.83 mmol) 2,2-dimethoxypropane and 0.71 g (3.73 mmol) p-toluenesulfonic acid monohydrate were dissolved in 50 mL acetone. The reaction mixture was stirred for 2 h at room temperature. After neutralizing the catalyst by adding a NH$_3$/EtOH (8 N) solution the solvent was evaporated at room temperature. The residue was then dissolved in (250 ml) ethyl acetate and extracted with two portions of (20 ml) water. The organic phase was dried with MgSO$_4$ and evaporated to give 14 as white crystals: 12.0 g, (92%). All analytical data for this compound matched those expected for the assigned structure.

Example 4

4.1 Preparation of PEO-([G1]-(Acetonide)$_3$ (compound 15) and a General Esterification Procedure by DCC Coupling Isopropylidene-2,2-bis(methoxy)propanoic acid (14) 520 mg (3 mmol), 2.0 g (100 μmol) tri-arm star PEO with a molecular weight of 22550 and a polydispersity of 1.02 and 120 mg (1 mmol) DMAP were dissolved in 5 ml CH$_2$Cl$_2$. 620 mg (3 mmol) of DCC was added. After stirring at room temperature for 15 h the DCC-urea was filtered off in a glass filter and washed with a small volume of CH$_2$Cl$_2$. The crude product was purified by precipitation into diethyl ether to give 15 as a white solid: 1.86 g, (87%). All analytical data for this compound matched those expected for the assigned structure.

4.2 PEO-([G1]-(OH)$_6$ (compound 16) and a General Procedure for Removal of the Acetonide Protective Group PEO-([G1]-(Acetonide)$_3$ (15) 1.24 g (61 μmol) was dissolved in 20 mL methanol. 0.5 mL H$_2$SO$_4$ (2M) was added and the reaction mixture was stirred overnight at room temperature. After neutralizing the catalyst using a NH$_3$/EtOH (8 N) solution, the precipitated ammonium sulfate was filtered off in a glass filter and carefully washed with methanol. The methanol solution was precipitated into diethyl ether to give 16 as a white solid: 770 mg, (62%). All analytical data for this compound matched those expected for the assigned structure.

4.3 Preparation of PEO-([G2]-Acetonide)$_6$ (compound 17)

PEO-([G1]-(OH)$_6$ (16) 2.96 g (145 μmol), 180 mg (1.45 μmol) DMAP, 760 mg (4.34 mmol) isopropylidene-2,2-bis(methoxy)propanoic acid (14) and 900 mg (4.24 mmol) DCC were allowed to react according to the general esterification procedure by DCC coupling in 20 mL of dry CH$_2$Cl$_2$. 17 was isolated as a white solid after precipitation into diethyl ether: 2.84 g, (92%). All analytical data for this compound matched those expected for the assigned structure.

4.4 Preparation of PEO PEO-([G2]-(OH)$_{12}$ (compound 18)

PEO -([G2]-(Acetonide)$_6$ (17) 2.71 g (130 μmol) and 0.5 mL H$_2$SO$_4$ (2M) were allowed to react according to the general procedure for the removal of the acetonide protective group in 20 mL of methanol. 18 was isolated as a white solid after precipitation into diethyl ether: 2.25 g, (84%). All analytical data for this compound matched those expected for the assigned structure.

4.5 Preparation of PEO-([G2]-(4-nitrophenyl carbonate)$_{12}$ (19)

PEO-([G2]-(OH)$_{12}$ (18) 1.07g (51 μmol) and 240 mg (3.05 mmol) pyridine were dissolved in 4 mL of CH$_2$Cl$_2$. 610 mg (3.05 mmol) 4-nitrophenyl chloroformate were added and the reaction mixture was stirred overnight at room temperature. After precipitation of the reaction mixture into diethyl ether 19 was isolated as a white solid: 900 mg, (77%). All analytical data for this compound matched those expected for the assigned structure.

4.6 Preparation of PEO-([G2]-(t-butylcarbazate)$_{12}$ (20)

PEO-([G2]-(4-nitrophenyl carbonate)$_{12}$ (19) 840 mg (36 μmol) and 20 mg (146 μmol) DMAP were dissolved in 6 mL of benzene. 290 mg (2.19 mmol) tert-butylcarbazate was added and the reaction mixture was stirred over night at room temperature. After precipitation of the reaction mixture into diethyl ether 20 was isolated as a white solid: 690 mg, (84%). All analytical data for this compound matched those expected for the assigned structure.

4.7 Preparation of PEO-([G2]-hydrazide)$_3$ (21)

PEO-([G#2]-(t-butylcarbazate)$_{12}$ (20) 620 mg (27 μmol) was dissolved in 2 mL of CH$_2$Cl$_2$. 2 mL of trifluoroacetic acid (TFA) was added and the reaction mixture was stirred over night at room temperature. After precipitation of the reaction mixture into diethyl ether 21 was isolated as a white solid: 360 mg, (61%). All analytical data for this compound matched those expected for the assigned structure.

4.8 Preparation of PEO-([G2]-(DOX)$_{12}$ (22)

PEO-([G2]-(hydrazide)$_{12}$ (21) 840 mg (36 μmol), 95 mg (164 μmol) Doxorubicin and one drop of TFA were dissolved in 3 mL of CH$_2$Cl$_2$ and stirred over night at room temperature. The crude product was purified using a LH-20 Sephadex resin and methanol as eluent. After evaporation of the methanol the primary fraction was dissolved in water and lyophilized to give 22 as a red powder: 690 mg, (84%).

Example 5

Example 5 details the dendronization of polymers, using polystyrene as an exemplary dendrimer core moiety.

5.1 General Procedure for Dendronization Via Reaction of Polymeric Pendant Groups with Anhydride 2

The polymer sample with pendant hydroxyl, thiol, or amino groups was dissolved in pyridine to a concentration of approximately 0.02M. The solution was then treated with 1–1.5 equivalents of the acid anhydride monomer 2 and a catalytic amount of dimethylaminopyridine (DMAP). The flask was sealed and stirred overnight. The reaction mixture was precipitated into methanol to precipitate the dendronized polymer.

5.2 General Procedure for the Hydrogenolysis of Benzylidene Protecting Groups The benzylidene protected polymer sample was dissolved in a mixture of THF/methanol and the catalyst Pd/C was added. The reaction mixture was placed in a Parr pressure vessel and stirred overnight under 10 atm of H$_2$. The reaction mixture was filtered over celite to remove the Pd/C catalyst. The filtrate was evaporated to afford the desired polymer with deprotected pendant hydroxyl groups.

5.3 Synthesis of Generation 1 Dendronized poly(p-hydroxystyrene) by Reaction with Anhydride 2

1.0 g of poly(p-hydroxystyrene) with molecular weight 10,000 [MALDI-TOF Mn=10,200, PDI=1.07] was added to a dry round bottom flask equipped with a magnetic stir bar, and dissolved in pyridine to a concentration of approximately 0.02M (1.7M per repeat unit). The solution was then treated with 5.3 g of the acid anhydride 2 (1.5 equivalents per repeat unit), as previously prepared, and 0.3 g of DMAP catalyst (0.3 equiv. per repeat unit). The flask was sealed and stirred overnight. The reaction mixture was precipitated into methanol to afford a white powder in 99% yield; $^1$H NMR (CD$_3$Cl, δ, ppm, TMS) 0.9–1.1 (br, 3), 1.1–2.2 (br, 3), 3.4–3.6 (br, 2), 4.6–4.8 (br, 2), 5.3–5.5 (br, 1), 6.1–6.9 (br, 4), 7.1–7.3 (br, 3), 7.3–7.5 (br, 2). $^{13}$C NMR (CDCl$_3$, δ, ppm, TMS) 17.8 (CH$_3$), 39–41 (CH), 42.5 (C), 43–46 (CH$_2$), 73.2 (CH$_2$), 101.7 (CH), 120–121 (CH), 126.2 (CH), 128.1 (CH), 128–129 (CH), 128.9 (CH), 138.0 (C), 142–144 (C) 148–149 (C) 172–173 (C); MS (MALDI-TOF): (m/z), Mn=27,300, PDI=1.03.

5.4 Deprotection of Generation 1 Dendronized poly(p-hydroxystyrene) by Hydrogenolysis of the Benzylidene Protecting Groups The benzylidene protected polymer sample prepared in 5.3 (0.3 g) was dissolved in 50/50 THF/methanol and added to a vial containing a stir bar. Pd/C (10 mg) was added to the sample and the vial was placed in a Parr pressure vessel and stirred overnight under 10 atm of $H_2$. The reaction mixture was filtered over celite to remove the Pd/C catalyst. The filtrate was evaporated to afford a clear glass in 99% yield. $^1$H NMR (CD$_3$SOCD$_3$, δ, ppm, TMS) 1.1–1.2 (br, 3), 1.1–2.2 (br, 3), 3.5–3.6 (br, 2), 3.6–3.7 (br, 2), 4.8–5.0 (br, 2), 6.2–7.0 (br, 4). $^{13}$C NMR (CDCl3, δ, ppm, TMS) 16.9 (CH3), 39–41 (CH), 43–46 (CH$_2$), 50.7 (C), 63.9 (CH$_2$), 121–122 (CH), 128–129 (CH), 128.9 (CH), 142–144 (C) 148–149 (C) 173–174 (C); MS (MALDI-TOF): (m/z), Mn=19,300, PDI=1.09.

5.5 Preparation of Generation 2 Dendronized poly(p-hydroxystyrene) by Reaction with Anhydride 2

This polymer was prepared as described in 5.3 by esterification of the deprotected generation 1 dendronized polymer with the acid anhydride. The polymer was obtained in 93% yield. $^1$H NMR (CDCl$_3$, δ, ppm, TMS) 0.6–0.9 (br, 6), 0.9–2.2 (br, 6), 3.3–3.7 (br, 4), 4.2–4.7 (br, 8), 5.2–5.4 (br, 2), 6.0–6.9 (br, 4), 7.0–7.3 (br, 6), 7.3–7.5 (br, 4). $^{13}$C NMR (CDCl$_3$, δ, ppm, TMS) 17.8 (CH$_3$), 39–41 (CH), 42.5 (C), 43–46 (CH$_2$), 73.2 (CH$_2$), 101.7 (CH), 120–121 (CH), 126.2 (CH), 128.1 (CH), 128–129 (CH), 128.9 (CH), 138.0 (C), 142–144 (C) 148–149 (C) 172–173 (C); MS (MALDI-TOF): (m/z), Mn=54,700, PDI=1.03.

5.6 Deprotection of Generation 2 Dendronized poly(p-hydroxystyrene) by Hydrogenolsis of the Benzylidene Protecting Groups This polymer was prepared by hydrogenolysis of the generation 2 dendronized polymer of 5.5. Yield: 94%. $^1$H NMR (CD$_3$SOCD$_3$, δ, ppm, TMS) 0.8–2.2 (br, 12), 3.4–3.5 (br, 2), 3.5–3.6 (br, 2), 4.1–4.4 (br, 4), 4.6–4.8 (br, 4), 6.1–7.2 (br, 4). $^{13}$C NMR (CD$_3$SOCD$_3$, δ, ppm, TMS) 16.8 (CH$_3$), 17.3 (CH$_3$), 46.6 (C), 50.4 (C), 63.9 (CH$_2$), 64.8 (CH$_2$), 120–121 (CH), 128–129 (CH), 142–144 (C) 148–149 (C) 171–172 (C), 174.2 (C); MS (MALDI-TOF): (m/z), Mn=40,300, PDI=1.05

5.7 Preparation of Generation 3 Dendronized poly(p-hydroxystyrene) by Reaction with 2

This polymer was prepared as described in 5.5 by esterification of the deprotected generation 2 dendronized polymer with the acid anhydride 2. The polymer was obtained in 96% yield. $^1$H NMR (CDCl$_3$, δ, ppm, TMS) 0.3–1.8 (br, 24), 3.2–3.8 (br, 8), 3.9–4.9 (br, 20), 5.3–5.5 (br, 4), 6.1–6.9 (br, 4), 7.1–7.3 (br, 12), 7.3–7.5 (br, 8). $^{13}$C NMR (CDCl$_3$, δ, ppm, TMS) 17.3 (CH$_3$), 17.6 (CH$_3$), 17.8 (CH$_3$), 42.4 (C), 46.6 (C), 46.8 (C), 64.9 (CH$_2$), 73.2 (CH$_2$), 101.4 (CH), 120–121 (CH), 126.2 (CH), 128.1 (CH), 128.9 (CH), 128.9 (CH), 137.0 (C), 148–149 (C) 170.8 (C), 171.9 (C), 173.2 (C); MS (MALDI-TOF): (m/z), Mn=109,600, PDI=1.02.

Example 6

Example 6 details the preparation of dendrimers of the invention, which are based upon a nucleic acid core.

6.1 Dendrimer Coupling to DNA Strand to a Pre-formed Dendrimer Through its Focal Point 6.1a First Generation Dendrimer: DNA-[G-1]-OH$_2$ Single stranded DNA, having a sequence of TTC TCT TCA GTT CAC A (5' to 3'), was synthesized on a 1 μmole scale using UltraMILD phosphoramidites from Glen Research. The final trityl deprotection step was omitted from the synthesizer, and the samples were stored on the CPG (controlled pore glass) resin. The CPG-bound DNA beads were transferred to a fritted 1.5 mL disposable chromatography column (BioRad) and fitted with a Teflon stopcock. Reagents were added via syringe, and the reactions were terminated via filtration. The beads were washed with CH$_3$OH, a 5% solution of 4-dimethylamino pyridine (DMAP) in CH$_3$OH, and then flushed with additional CH$_2$Cl$_2$. Deprotection of the 5' dimethyoxytrityl (DMT) group under acidic conditions of 3% trichloroacetic acid (TCA) in CH$_2$Cl$_2$ offered a free hydroxy moiety at the terminus. Formation of the [G-1] conjugate was accomplished by adding 0.5 M acetonide anhydride 2 and 0.5 M DMAP in methylene chloride. Subsequent removal of the acetonide protecting group under acidic conditions of 10% TCA in ethylene glycol afforded the [G-1] diol. The DNA-dendrimer conjugates were cleaved from the solid phase resin under basic conditions of 1:1 morpholine:methanol for 2 h at 60° C. and purified by reverse-phase HPLC. The identity of the conjugate was confirmed by MALDI-TOF MS. Thermal denaturation studies demonstrated that the conjugate hybridized with a complementary strand of DNA. No appreciable difference in the melting temperature was observed as compared with an unmodified strand. Thermal Denaturation: $T_{m, native}$ 52.3° C., $T_{m, G1}$ 52.3° C. MALDI-TOF MS: (m/z) 4898 (M–H)

6.1b Second Generation Dendrimer: DNA-[G-2]-OH$_4$

The DNA sample was prepared as described in 6.1a to generate the 5' hydroxy terminus. Esterification with 0.5 M of an acetonide-protected [G-2] dendron having a carboxylic acid at the focal point was accomplished using 0.5 M 1,3-diisopropylcarbodiimide (DIC) and 0.5 M DMAP in methylene chloride for 12 h. Acetonide deprotection and subsequent cleavage from the resin was then performed as described in 6.1a. The identity of the conjugate was confirmed by MALDI-TOF MS. The conjugate exhibited thermal behavior similar to the native strand. Thermal Denaturation: $T_{m, G2}$ 52.4° C. MALDI-TOF MS: (m/z) 5131 (M–H).

6.1c Third Generation Dendrimer: DNA-[G-3]-OH$_8$

Bead preparation and DMT removal were executed on the same sequence as described in 6.1a. The beads were then subjected to 0.5 M of an acetonide-protected [G-3] dendron having a carboxylic acid at the focal point, 0.5 M DIC, and 0.5 M DMAP, all in CH$_2$Cl$_2$, for 12 h. The acetonide groups were removed under acidic conditions to yield eight hydroxyl functionalities at the periphery. Cleavage from the resin was accomplished as described in 6.1a. The identity of the conjugate was confirmed by MALDI-TOF MS. Hybridization occurred with a melting temperature equivalent to that of the unmodified strand. Thermal Denaturation: $T_{m, G3}$ 52.3° C. MALDI-TOF MS: (m/z) Calc. 5596 (M–H). Found: 5590 (M–H).

6.2 Divergent Synthesis of a DNA-Dendrimer Conjugate

In this approach a DNA strand is used as a core for the growth of a dendrimer affording a DNA dendrimer conjugate. The growth in this example is carried out through the first, second, third to the fourth generation dendrimer. Growth could be continued further to higher generations.

6.2a Preparation of Fourth Generation DNA Dendrimer Conjugate by Divergent Growth Using the Anhydride Derivative of Isopropylidene bis-MPA: $T_{16}$-[G-4]-Acetonide$_8$.

A DNA strand composed of sixteen deoxythymidine residues was prepared on solid phase, as described in 6.1a. After DMT removal, the beads were subjected to coupling conditions of 1 M acetonide anhydride of bis-MPA and 1 M DMAP in methylene chloride. Deprotection of the acetonide was accomplished using 10% TCA in ethylene glycol. Coupling and deprotection steps were repeated to produce [G-2], [G-3], and [G-4] conjugates. After each coupling step, a small sample of beads was cleaved from the resin under basic conditions of 1:1 morpholine:methanol for 2 h at 60° C. and purified by reverse-phase HPLC. The identity of these acetonide-protected conjugates was confirmed by MALDI-TOF MS. [G-1]: (m/z) Calc. 4965 (M–H). Found: 4966 (M–H). [G-2]: (m/z) Calc. 5231 (M–H). Found: 5232

(M–H). [G-3]: (m/z) Calc. 5779 (M–H). Found: 5776 (M–H). [G-4]: (m/z) Calc. 6862 (M–H). Found: 6863 (M–H).

Example 7

7.1 Preparation of a beta-alanine terminated [G2] dendrimer 0.2 mmole of [G2]-(OH)$_{12}$, (as obtained in example 2) is treated with 0.4 mmol of DMAP and 3.6 mmol of the anhydride of Cbz protected beta-alanine anhydride and allowed to react according to the general esterification procedure by anhydride coupling in 6 mL of dry pyridine. The desired Cbz protected modified [G2] is isolated as a glass after precipitation. Analysis of the product confirms that it has the expected structure. The corresponding [G-2] with twelve terminal amino group is then obtained by hydrogenolysis of the Cbz groups using Pd/C as the catalyst.

7.2 Preparation of a t-BOC protected 4-aminobenzoic acid terminated [G2] dendrimer 0.2 mmole of [G2]-(OH)$_{12}$, is treated with 0.4 mmol of DMAP and 3.6 mmol of the anhydride of t-BOC protected 4-aminobenzoic acid anhydride and allowed to react according to the general esterification procedure by anhydride coupling in 10 mL of dry pyridine. The desired t-BOC protected modified [G2] is isolated as a solid after precipitation. Analysis of the product confirms that it has the expected structure.

Example 8

As used herein PEO-Mono refers to PEO with one OH; PEO-di refers to PEO with two OH (this is actually also PEG) and PEO-Tetra refers to a star PEO with four OH.

8.1 PEO-Mono-[G-1]-Bn$_1$

The monomethylether PEO alcohol (Mn=5,500, polydispersity=1.03, 10.00 g, 2.00 mmoles, 1 equiv) was dissolved in 30 mL of CH$_2$Cl$_2$. The benzylidene anhydride 2 was added (1.71 g, 4.00 mmoles, 2.0 equiv), followed by the addition of DMAP (0.10 g, 0.80 mmoles, 0.40 equiv). After stirring the reaction mixture for 6h at room temperature 5 mL of MeOH were added for quenching the excess of anhydride 2. The mixture was stirred for 5 h and the product was precipitated directly from the reaction mixture solution into 1L of diethyl ether. The precipitate was filtered through a glass filter to yield 9.89 g of product as a white powder (95%). IR (cm$^{-1}$, thin film from CHCl$_3$): 2888, 1737, 1125. $^1$H-NMR (300 MHz, CDCl$_3$): δ 1.05 (s, 3), 3.38 (s, 3), 3.42 (m, 3), 3.61 (bs, ca. 600), 3.87 (t, 4, J=4.8), 4.36 (t, 2, J=4.8), 4.66 (d, 2, J=11.4), 5.44 (s, 1), 7.32 (m, 3), 7.42 (m, 2). $^{13}$C-NMR (500 MHz, CDCl$_3$): δ 17.85, 42.38, 58.87, 63.67, 64.15, 69.00, 70.50, 71.87, 73.45, 101.69, 126.14, 128.12, 128.89, 137.81, 173.87. Calcd.: [M]$^+$ m/z=5,705. Found: MALDI-TOF MS: [M]$^+$=5,694; polydispersity=1.03. Elemental Analysis (Anal.) Found: C, 53.41; H, 8.76.

8.2 PEO-Mono-[G-1]-OH$_2$

The PEO-Mono-[G-1]-Bn$_1$ (3.79 g, 0.73 mmoles) was dissolved in 25 mL of a 1:2 mixture of CH$_2$Cl$_2$ and MeOH. The catalyst (Pd/C 10%, 0.04 g) was added to the reaction mixture, followed by evacuation of the system. The reaction mixture was stirred vigorously for 6 h at room temperature under H$_2$ atmosphere. The catalyst was removed from the reaction mixture by filtration using a glass filter. The product in solution was precipitated in 500 mL of diethyl ether to yield 3.57 g of a white powder (95%). IR (cm$^{-1}$, thin film from CHCl$_3$): 3476, 2893, 1726, 1129. $^1$H-NMR (300 MHz, CDCl$_3$): δ 1.10 (s, 3), 3.37 (s, 3), 3.63 (bs, ca. 600), 4.33 (t, 2, J=4.8). $^{13}$C-NMR (500 MHz, CDCl$_3$): δ 16.97, 49.49, 56.68, 58.83, 63.16, 63.53, 67.11, 68.59, 70.35, 71.72, 84.02, 175.44. Calcd.: [M]$^+$ m/z=5,617. Found: MALDI-TOF MS: [M]$^+$=5,610; polydispersity=1.03. Anal. Found: C, 53.86; H, 9.08.

8.3 PEO-Mono-[G-2]-Bn$_2$.

The PEO-Mono-[G-1]-OH$_2$ (8.00g, 1.56 mmoles, 1.0 equiv) was dissolved in 18 mL of CH$_2$Cl$_2$. The benzylidene anhydride 2 (5.32 g, 12.48 mmoles, 8.0 equiv), and DMAP (0.30 g, 2.50 mmoles, 1.6 equiv) were added to the solution. The reaction mixture was stirred for 15 h at room temperature followed by the addition of 5 mL of MeOH into the reaction mixture for quenching the excess anhydride 2 and stirred for 7 h. The product was precipitated directly from the reaction mixture into 1L of diethyl ether. The precipitate was filtered through a glass filter to yield 7.82 g of product as a white powder (91%). IR (cm$^{-1}$, thin film from CHCl$_3$): 2888, 1737, 1096. $^1$H-NMR (300 MHz, CDCl$_3$): δ 0.95 (s, 6), 1.26 (s, 3), 3.36 (s, 3), 3.63 (bs, ca. 600), 3.79 (s, 4), 3.87 (t, 2, J=4.8), 4.12 (t, 2, J=4.8), 4.39 (s, 4), 4.58 (d, 4, J=11.4), 5.41 (s, 2), 7.32 (m, 6), 7.39 (m, 4). $^{13}$C-NMR (500 MHz, CDCl$_3$): δ, 17.68, 42.51, 46.70, 58.97, 64.15, 65.43, 68.62, 70.50, 71.86, 73.38, 101.63, 126.10, 128.04, 128.78, 137.74, 172.54, 173.16. Calcd.: [M]$^+$ m/z=6,025. Found: MALDI-TOF MS: [M]$^+$=6,020; polydispersity=1.03. Anal. Found: C, 55.10; H, 8.90.

8.4 PEO-Mono-[G-2]-OH$_4$.

The PEO-Mono-[G-2]-Bn$_2$ (3.08 g, 0.56 mmoles) was dissolved in 15 mL of a 1:2 mixture of CH$_2$Cl$_2$ and MeOH. The Pd/C catalyst (0.3 g) was added to the reaction mixture, followed by evacuation of the system. The reaction mixture was stirred vigorously for 10 h at room temperature under H$_2$ atmosphere. The catalyst was removed by filtration using a glass filter. The product in solution was precipitated in 500 mL of diethyl ether to yield 2.76 g of a white powder (93%). IR (cm$^{-1}$, thin film from CHCl$_3$): 3464, 2904, 1735, 1154. $^1$H-NMR (400 MHz, CDCl$_3$): δ 1.07 (s, 6), 1.31 (s, 3), 3.37 (s, 3), 3.46 (m, 4), 3.64 (bs, ca. 600), 3.81 (t, 8, J=5.2), 4.31 (m, 4), 4.40 (d, 2, J=10.8). $^{13}$C-NMR (500 MHz, CDCl$_3$): δ 17.08, 17.96, 46.40, 49.70, 58.95, 63.64, 64.33, 64.84, 67.39, 68.79, 70.47, 71.84, 84.15, 172.97, 174.97. Calcd.: [M]$^+$ m/z=5,849. Found: MALDI-TOF MS: [M]$^+$=5,848; polydispersity=1.03. Anal. Found: C, 55.51; H, 9.07.

8.5 PEO-Mono-[G-3]-Bn$_4$.

The PEO-Mono-[G-2]-OH$_4$ (5.58 g, 1.01 mmoles, 1.0 equiv) was dissolved in 30 mL of CH$_2$Cl$_2$. The benzylidene anhydride 2 (8.62 g, 20.20 mmoles, 20.0 equiv), and DMAP (0.25 g, 2.02 mmoles, 2.0 equiv) were added to the solution. The reaction mixture was stirred for 18 h at room temperature. For quenching the excess anhydride 2, 5 mL of MeOH were added into the reaction mixture and stirred for 8 h. The product was precipitated directly from the reaction mixture into 1 L of diethyl ether. The precipitate was filtered through a glass filter to yield 5.68 g of product as a white powder (91%). IR (cm$^{-1}$, thin film from CHCl$_3$): 2886, 1739, 1106. $^1$H-NMR (400 MHz, CDCl$_3$): δ 0.92 (s, 12), 1.04 (s, 3), 1.20 (s, 6), 3.38 (s, 3), 3.46 (m, 4), 3.64 (bs, ca. 600), 3.81 (t, 3, J=4.8), 4.06 (q, 4, J=5.2), 4.17 (t, 2, J=4.8), 4.34 (m, 8), 4.56 (d, 8, J=11.6), 5.40 (s, 4), 7.30 (m, 12), 7.38 (m, 8). $^{13}$C-NMR (400 MHz, CDCl$_3$): δ 17.18, 17.57, 17.61, 42.30, 46.34, 46.80, 58.94, 64.15, 65.06, 65.75, 70.49, 71.85, 73.35, 73.43, 101.95, 126.08, 128.02, 128.75, 137.75, 171.79, 172.01, 173.11. Calcd.: [M]$^+$ m/z=6,665. Found: MALDI-TOF MS: [M]$^+$=6,678; polydispersity=1.03. Anal. Found: C, 56.00; H, 8.44.

8.6 PEO-Mono-[G-3]OH$_8$.

The PEO-Mono-[G-3]-Bn$_4$ (2.14 g, 0.35 mmoles) was dissolved in 10 mL of a 1:2 mixture CH$_2$Cl$_2$/MeOH. The catalyst (Pd/C 10%, 0.2 g) was added to the reaction mixture. After evacuation of system, the reaction mixture was stirred vigorously for 15 h at room temperature under a H$_2$ atmosphere. The catalyst was removed by filtration of the reaction mixture through a glass filter. The product in solution was precipitated in 500 mL of diethyl ether to yield 1.84 g of a white powder (91%). IR (cm$^{-1}$, thin film from CHCl$_3$): 3455, 2885, 1737, 1106. $^1$H-NMR (300 MHz, d$_6$-DMSO): δ 1.01 (s, 12), 1.16 (s, 6), 1.19 (s, 3), 3.24 (s, 3), 3.51 (bs, ca. 600), 3.66 (s, 4), 3.74 (t, 3, J=4.8), 4.16 (m, 16), 4.63 (t, 8, J=5.4). $^{13}$C-NMR (400 MHz, d$_6$-DMSO): δ 16.68, 16.97, 17.08, 46.09, 46.30, 50.24, 58.02, 63.65, 64.06, 64.47, 68.00, 69.57, 69.77, 71.37, 171.80, 171.98, 174.03. Calcd.: [M]$^+$ m/z=6,313. Found: MALDI-TOF MS: [M]$^+$=6,302; polydispersity=1.03. Anal.: Found: C, 55.79; H, 8.75.

8.7 PEO-Mono-[G-4]-Bn$_8$.

The PEO-Mono-[G-3]-OH$_8$ (2.63 g, 0.45 mmoles, 1.0 equiv) was dissolved in 25 mL of CH$_2$Cl$_2$. The benzylidene anhydride 2 (6.14 g, 14.40 mmoles, 32.0 equiv), and DMAP (0.35 g, 2.88 mmoles, 6.4 equiv) were added to the solution. The reaction mixture was stirred for 18 h at room temperature. It was followed by the addition of 5 mL of MeOH for quenching the excess anhydride 2 and stirred for 7 h. The product was precipitated directly from the reaction mixture into 1 L of diethyl ether. The precipitate was filtered through a glass filter to yield 2.97 g of product as a white powder (89%). IR (cm$^{-1}$, thin film from CHCl$_3$): 2873, 1741, 1117. $^1$H-NMR (300 MHz, CDCl$_3$): δ 0.90 (s, 24), 1.01 (s, 6), 1.14 (s, 3), 1.19 (s, 12), 3.38 (s, 3), 3.62 (bs, ca. 600), 3.88 (t, 2, J=4.8), 4.05 (s, 6), 4.15 (m, 6), 4.33 (m, 16), 4.55 (d, 16, J=11.7), 5.38 (s, 8), 7.29 (m, 24), 7.38 (m, 16). $^{13}$C-NMR (400 MHz, CDCl$_3$): δ 17.10, 17.24, 17.58, 24.45, 46.42, 46.76, 58.92, 64.17, 64.97, 65.34, 66.04, 70.48, 71.84, 73.32, 73.38, 101.55, 126.08, 128.00, 128.73, 137.78, 171.30, 171.76, 173.07. Calcd.: [M]$^+$ m/z=7,945. Found: MALDI-TOF MS: [M]$^+$=7,950; polydispersity=1.03. Anal.: Found: C, 56.94; H, 8.19.

8.8 PEO-Mono-[G-4]-OH$_{16}$.

The PEO-Mono-[G-4]-Bn$_8$ (1.21 g, 0.16 mmoles) was dissolved in 12 mL of a 1:2 mixture CH$_2$Cl$_2$/MeOH. The catalyst (Pd/C 10%, 0.1 g) was added to the reaction mixture. After evacuation of system, the reaction mixture was stirred vigorously for 18 h at room temperature under a H$_2$ atmosphere. The catalyst was removed by filtration of the reaction mixture through a glass filter. The product in solution was precipitated in 500 mL of diethyl ether to yield 0.90 g of a white powder (83%). IR (cm$^{-1}$, thin film from CHCl$_3$): 3447, 2886, 1736, 1127. $^1$H-NMR (300 MHz, d$_6$-DMSO): δ 1.00 (s, 24), 1.16 (s, 12), 1.18 (s, 6), 1.21 (s, 3), 3.24 (s, 3), 3.51 (bs, ca. 600), 3.72 (t, 3, J=4.8), 4.15 (m, 30), 4.63 (t, 16, J=5.4). $^{13}$C-NMR (400 MHz, d$_6$-DMSO): δ 16.68, 16.83, 17.10, 46.19, 46.24, 50.21, 58.02, 63.64, 64.36, 69.77, 71.26, 171.35, 171.80, 174.01. Calcd.: [M]$^+$ m/z=7,241. Found: MALDI-TOF MS: [M]$^+$=7,240; polydispersity=1.03. Anal. Found: C, 54.34; H, 8.46.

8.9 PEO-Di-[G-1]-Bn$_2$.

The PEO diol (Mn=10,604; polydispersity=1.03; 10.00 g, 0.91 mmoles, 1.0 equiv) was dissolved in 25 mL of CH$_2$Cl$_2$. The benzylidene anhydride 2 was added (2.40 g, 5.50 mmoles, 6.0 equiv), followed by the addition of DMAP (0.67 g, 0.55 mmoles, 0.60 equiv). After stirring the reaction mixture for 6 h at room temperature, 5 mL of MeOH were added for quenching the excess of anhydride. The mixture was stirred for 5 h and the product was precipitated directly from the reaction mixture solution into 1 L of diethyl ether. The precipitate was filtered through a glass filter to yield 9.86 g of product as a white powder (95%). IR (cm$^{-1}$, thin film from CHCl$_3$): 2891, 1737, 1146. $^1$H-NMR (300 MHz, CDCl$_3$): δ 1.04 (s, 6), 3.40 (t, 6, J=5.0), 3.63 (bs, ca. 1100), 3.87 (t, 6, J=5.0), 4.35 (t, 4, J=5.0), 4.66 (d, 4, J=11.4), 5.44 (s, 2), 7.32 (m, 6), 7.41 (m, 4). $^{13}$C-NMR (500 MHz, CDCl$_3$): δ 17.80, 42.34, 56.78, 63.63, 64.11, 68.96, 70.46, 73.40, 101.65, 126.10, 128.07, 128.85, 137.77, 173.82. Calcd.: [M]$^+$ m/z=11,014. Found: MALDI-TOF MS: [M]$^+$=11,032; polydispersity=1.03. Anal. Found: C, 54.65; H, 8.82.

8.10 PEO-Di-[G-1]-OH$_4$.

The PEO-Di-[G-1]-Bn$_2$ (7.95 g, 0.70 mmoles) was dissolved in 40 mL of a 1:2 mixture of CH$_2$Cl$_2$ and MeOH. The catalyst (Pd/C 10%, 0.2 g) was added to the reaction mixture, followed by evacuation of the system. The reaction mixture was stirred vigorously for 8 h at room temperature under H$_2$ atmosphere. The catalyst was removed from the reaction mixture by filtration using a glass filter. The product in solution was precipitated in 1 L of diethyl ether to yield 7.36 g of a white powder (94%). IR (cm$^{-1}$, thin film from CHCl$_3$): 3479, 2889, 1728, 1148. $^1$H-NMR (400 MHz, CDCl$_3$): δ 1.12 (s, 6), 3.64 (bs, ca. 1100), 4.33 (t, 4, J=5.0). $^{13}$C-NMR (500 MHz, CDCl$_3$): δ 17.02, 49.52, 56.60, 63.34, 63.44, 66.64, 68.65, 70.17, 83.94, 175.45. Calcd.: [M]$^+$ m/z=10,838. Found: MALDI-TOF MS: [M]$^+$=10,838; polydispersity=1.03. Anal. Found: C, 53.16; H, 8.27.

8.11 PEO-Di-[G-2]-Bn$_4$.

The PEO-Di-[G-1]-OH$_4$ (12.19 g, 1.09 mmoles, 1.0 equiv) was dissolved in 40 mL of CH$_2$Cl$_2$. It was followed by the addition of the benzylidene anhydride 2 (7.44 g, 17.44 mmoles, 16.0 equiv) and DMAP (0.43 g, 3.49 mmoles, 3.2 equiv). After stirring the reaction mixture for 10 h at room temperature, 5 mL of MeOH were added for quenching the excess of anhydride 2. The mixture was stirred for 8 h and the product was precipitated directly from the reaction mixture solution into 1 L of diethyl ether. The precipitate was filtered through a glass filter to yield 11.74 g of product as a white powder (89%). IR (cm$^{-1}$, thin film from CHCl$_3$): 2887, 1738, 1097. $^1$H-NMR (400 MHz, CDCl$_3$): δ 0.95 (s, 12), 1.26 (s, 6), 3.64 (bs, ca. 1100), 3.81 (t, 4, J=4.8), 4.13 (t, 4, J=4.8), 4.39 (s, 8), 4.59 (d, 8, J=11.6), 5.42 (s, 4), 7.40 (m, 12), 7.47 (m, 8). $^{13}$C-NMR (500 MHz, CDCl$_3$): δ 17.55, 17.58, 42.41, 46.60, 58.86, 63.57, 64.05, 65.32, 68.52, 70.40, 71.76, 73.28, 73.37, 83.96, 101.52, 126.01, 127.94, 128.68, 137.65, 172.44, 173.06. Calcd.: [M]$^+$ m/z=11,654. Found: MALDI-TOF MS: [M]$^+$=11,631; polydispersity=1.03. Anal. Found: C, 54.70; H, 8.46.

8.12 PEO-Di-[G-2]-OH$_8$.

The PEO-Di-[G-2]-Bn$_4$ (11.45 g, 0.95 mmoles) was dissolved in 70 mL of CH$_2$Cl$_2$/MeOH (1:2) mixture. The Pd/C (10%) used as catalyst (0.5 g) was added to the reaction mixture, followed by evacuation of the system. The reaction mixture was stirred vigorously for 16 h at room temperature under H$_2$ atmosphere. The catalyst was removed from the reaction mixture by filtration using a glass filter. The product in solution was precipitated in 1 L of diethyl ether to yield 10.27 g of a white powder (92%). IR (cm$^{-1}$, thin film from CHCl$_3$): 3466, 2886, 1730, 1147. $^1$H-NMR (300 MHz, CDCl$_3$): δ 1.07 (s, 12), 1.31 (s, 6), 3.26 (m, 8), 3.40 (t, 6, J=4.8), 3.64 (bs, ca. 1100), 4.32 (m, 8), 4.40 (d, 4, J=11.1). $^{13}$C-NMR (500 MHz, CDCl$_3$): δ 17.04, 17.92, 46.35, 49.67, 56.75, 63.60, 64.28, 64.79, 67.27, 68.74, 70.42, 84.10, 172.93, 174.89. Calcd.: [M]$^+$ m/z=11,302. Found: MALDI-TOF MS: [M]$^+$=11,292; polydispersity=1.03. Anal. Found: C, 53.31; H, 8.39.

8.13 PEO-Di-[G-3]-Bn$_8$.

The PEO-Di-[G-2]-OH$_8$ (8.02 g, 0.69 mmoles, 1.0 equiv) was dissolved in 60 mL of CH$_2$Cl$_2$. It was followed by the addition of the benzylidene anhydride 2 (9.36 g, 21.95 mmoles, 32.0 equiv) and DMAP (0.54 g, 4.39 mmoles, 6.4 equiv). After stirring the reaction mixture for 15 h at room temperature, the excess of anhydride 2 was quenched by the addition of 5 mL of MeOH. The mixture was stirred for 8 h and the product was precipitated directly from the reaction mixture solution into 1 L of diethyl ether. The precipitate was filtered through a glass filter to yield 8.44 g of product as a white powder (92%). IR (cm$^{-1}$, thin film from CHCl$_3$): 2894, 1741, 1128. $^1$H-NMR (400 MHz, CDCl$_3$): 60.93 (s, 24), 1.04 (s, 6), 1.20 (s, 12), 3.46 (t, 6, J=4.8), 3.64 (bs, ca. 1100), 3.81 (t, 3, J=4.8), 4.08 (q, 6, J=5.8), 4.28 (t, 3, J=4.8), 4.34 (m, 16), 4.56 (d, 16, J=11.6), 5.40 (s, 8), 7.30 (m, 24), 7.39 (m, 16). $^{13}$C-NMR (400 MHz, CDCl$_3$): δ 17.07, 17.46, 17.50, 42.36, 46.23, 46.68, 64.04, 64.94, 65.61, 68.48, 70.37, 73.23, 73.31, 101.46, 125.97, 127.90, 128.62, 137.66, 171.67, 171.90, 172.98. Calcd.: [M]$^+$ m/z=12,934. Found: MALDI-TOF MS: [M]$^+$=12,946; polydispersity=1.03. Anal. Found: C, 56.06; H, 8.33.

8.14 PEO-Di-[G-3]-OH$_{16}$.

The PEO-Di-[G-3]-Bn$_8$ (8.10 g, 0.61 mmoles) was dissolved in 45 mL of 1:2 mixture of CH$_2$Cl$_2$/MeOH. The Pd/C (10%) used as catalyst (0.8 g) was added to the reaction mixture, followed by evacuation of the system. The reaction mixture was stirred vigorously for 18 h at room temperature under H$_2$ atmosphere. The catalyst was removed from the reaction mixture by filtration using a glass filter. The product in solution was precipitated in 1 L of diethyl ether to yield 6.82 g of a white powder (89%). IR (cm$^{-1}$, thin film from CHCl$_3$): 3461, 2886, 1735, 1104. $^1$H-NMR (500 MHz, CDCl$_3$): δ 1.07 (s, 24), 1.29 (s, 6), 1.30 (s, 12), 3.28 (t, 5, J=5.8), 3.35 (t, 5, J=5.8), 3.50 (t, 6, J=5.8), 3.64 (bs, ca. 1100), 3.78 (m, 25), 4.30 (m, 20), 4.36 (dd, 10, J=11.0, 5.0). $^{13}$C-NMR (500 MHz, d$_6$-DMSO): δ 16.71, 16.99, 17.10, 46.11, 46.32, 50.26, 62.96, 63.65, 64.09, 64.50, 65.70, 68.02, 69.78, 76.61, 83.46, 171.83, 172.01, 174.06. Calcd.: [M]$^+$ m/z=12,230. Found: MALDI-TOF MS: [M]$^+$=12,229; polydispersity=1.03. Anal. Found: C, 53.38; H, 8.19.

8.15 PEO-Di-[G-4]-Bn$_{16}$.

The PEO-Di-[G-3]-OH$_{16}$ (4.61 g, 0.37 mmoles, 1.0 equiv) was dissolved in 50 mL of CH$_2$Cl$_2$. The benzylidene anhydride 2 (9.96 g, 23.36 mmoles, 64.0 equiv) and DMAP (0.57 g, 4.67 mmoles, 12.8 equiv) were added to the solution and the reaction mixture was stirred for 18 h at room temperature. The excess of anhydride 2 was quenched by the addition of 5 mL of MeOH. The mixture was stirred for 10 h and the product was precipitated directly from the reaction mixture solution into 500 mL of diethyl ether. The precipitate was filtered through a glass filter to yield 5.01 g of product as a white powder (86%). IR (cm$^{-1}$, thin film from CHCl$_3$): 2885, 1741, 1105. $^1$H-NMR (300 MHz, CDCl$_3$): δ 0.90 (s, 48), 1.01 (s, 12), 1.14 (s, 6), 1.19 (s, 24), 3.40 (t, 10, J=5.8), 3.64 (bs, ca. 1100), 3.80 (s, 5), 3.87 (t, 3, J=5.8), 4.04 (s, 12), 4.13 (m, 12), 4.33 (dd, 32, J=11.7, 5.0), 4.54 (d, 32, 11.4), 5.38 (s, 16), 7.29 (m, 48), 7.38 (m, 32). $^{13}$C-NMR (400 MHz, CDCl$_3$): δ 17.15, 17.63, 42.50, 46.42, 46.45, 46.79, 63.68, 64.22, 64.99, 65.35, 66.07, 70.51, 73.37, 73.43, 101.60, 126.13, 128.06, 128.79, 137.81, 171.34, 171.81, 173.12. Calcd.: [M]$^+$ m/z=15,494. Found: MALDI-TOF MS: [M]$^+$=15,510, polydispersity=1.03. Anal. Found: C, 57.08; H, 7.91.

8.16 PEO-Di-[G-4]-OH$_{32}$.

The PEO-Di-[G-4]-Bn$_{16}$ (4.50 g, 0.28 mmoles) was dissolved in 30 mL of a 1:2 mixture of CH$_2$Cl$_2$ and MeOH. The Pd/C (10%) used as catalyst (0.4 g) was added to the reaction mixture, followed by evacuation of the system. The reaction mixture was stirred vigorously for 18 h at room temperature under H$_2$ atmosphere. The catalyst was removed from the reaction mixture by filtration using a glass filter. The product in solution was precipitated in 500 mL of diethyl ether to yield 3.26 g of a white powder (80%). IR (cm$^{-1}$, thin film from CHCl$_3$): 3454, 2883, 1738, 1107. $^1$H-NMR (300 MHz, d$_6$-DMSO): δ 1.00 (s, 48), 1.16 (s, 24), 1.17 (s, 12), 1.21 (s, 6), 3.27 (t, 8, J=5.8), 3.64 (bs, ca. 1100), 3.66 (s, 16), 3.74 (t, 12, J=5.0), 4.15 (m, 68), 4.63 (t, 32, J=5.4). $^{13}$C-NMR (500 MHz, d$_6$-DMSO): δ 16.71, 16.86, 17.14, 46.21, 46.27, 50.24, 62.98, 63.64, 64.14, 64.37, 65.33, 66.11, 68.01, 69.80, 76.62, 171.39, 171.83, 174.05. Calcd.: [M]$^+$ m/z=14,086. Found: MALDI-TOF MS: [M]$^+$=14,090, polydispersity=1.03. Anal. Found: C, 52.79; H, 7.70.

8.17 PEO-Tetra-[G-1]-Bn$_4$.

The four-arm PEO star (Mn=20,330; polydispersity=1.10; 10.00 g, 0.50 mmoles, 1.0 equiv) was dissolved in 30 mL of CH$_2$Cl$_2$. The benzylidene anhydride 2 (1.71 g, 4.00 mmoles, 8.0 equiv) and DMAP (0.10 g, 0.80 mmoles, 1.6 equiv) were added to the solution. The reaction mixture was stirred for 15 h at room temperature. For quenching the excess anhydride 2, 5 mL of MeOH were added to the reaction mixture and stirred for 7 h. The product was precipitated directly from the reaction mixture solution into 1 L of diethyl ether. The precipitate was filtered through a glass filter to yield 10.02 g of product as a white powder (96%). IR (cm$^{-1}$, thin film from CHCl$_3$): 2884, 1736, 1106. $^1$H-NMR (300 MHz, CDCl$_3$): δ 1.03 (s, 12), 3.39 (m, 20), 3.62 (bs,), 3.77 (s, 22), 3.86 (t, 14, J=4.5), 4.34 (t, 8, J=4.8), 4.65 (d, 8, J=10.5), 5.43 (s, 4), 7.31 (m, 12), 7.40 (m, 8). $^{13}$C-NMR (500 MHz, CDCl$_3$): δ 17.85, 42.39, 64.16, 69.01, 70.50, 73.45, 101.70, 126.15, 128.13, 128.90, 137.81, 173.88. Calcd.: [M]$^+$ m/z=21,150. Found: MALDI-TOF MS: [M]$^+$=21,139, polydispersity=1.10. Anal. Found: C, 54.42; H, 8.71.

8.18 PEO-Tetra-[G-1]-OH$_8$.

The PEO-Tetra-[G-1]-Bn$_4$ (10.40 g, 0.50 mmoles) was dissolved in 60 mL of a 1:2 CH$_2$Cl$_2$/MeOH solvent mixture. The catalyst (Pd/C 10%, 0.25 g) was added to the reaction mixture and the system was evacuated. The reaction mixture was stirred vigorously for 18 h at room temperature under H$_2$ atmosphere. The catalyst was removed from the reaction mixture by filtration using a glass filter. The product in solution was precipitated in 1 L of diethyl ether to yield 10.02 g of a white powder (98%). IR (cm$^{-1}$, thin film from CHCl$_3$): 3477, 2885, 1733, 1104. $^1$H-NMR (400 MHz, CDCl$_3$): δ 1.11 (s, 12), 3.06 (t, 10, J=4.5), 3.41 (s, 10), 3.46 (t, 10, J=4.0), 3.64 (bs, ca. 2100), 3.80 (m, 18), 4.34 (t, 8, J=4.8). $^{13}$C-NMR (500 MHz, CDCl$_3$): δ 17.01, 45.20, 49.52, 63.23, 63.60, 67.21, 68.63, 70.24, 80.10, 175.50. Calcd.: [M]$^+$ m/z=20,798. Found: MALDI-TOF MS: [M]$^+$=20,812. Anal. Found: C, 54.28; H, 8.61.

8.19 PEO-Tetra-[G-2]-Bn$_8$.

The PEO-Tetra-[G-1]-OH$_8$ (6.78 g, 0.33 mmoles, 1.0 equiv) was dissolved in 40 mL of CH$_2$Cl$_2$. It was followed by the addition of the benzylidene protected anhydride 2 (5.65 g, 13.25 mmoles, 40.0 equiv) and DMAP (0.16 g, 1.33 mmoles, 4.0 equiv) to the solution. The reaction mixture was stirred for 16 h at room temperature. 5 mL of MeOH were added to the reaction mixture and stirred for 8 h to quench the excess anhydride 2. The product was precipitated directly from the reaction mixture solution into 1 L of diethyl ether. The precipitate was filtered through a glass filter to yield 7.01 g of product as a white powder (96%). IR (cm$^{-1}$, thin film from CHCl$_3$): 2887, 1739, 1130. $^1$H-NMR (300 MHz, CDCl$_3$): δ 0.95 (s, 24), 1.26 (s, 12), 3.63 (bs, ca. 2100), 3.79 (m, 20), 3.87 (m, 8), 4.13 (t, 6, J=4.8), 4.39 (s, 16), 4.58 (d, 16, J=11.7), 5.41 (s, 8), 7.30 (m, 24), 7.38 (m, 16). $^{13}$C-NMR (500 MHz, CDCl$_3$): δ 17.50, 17.53, 42.36, 45.30, 46.55, 56.65, 63.55, 64.01, 65.27, 68.47, 70.35, 73.23, 73.31, 84.10, 101.47, 125.96, 127.89, 128.63, 137.61, 172.39, 173.01. Calcd.: [M]$^+$ m/z=22,430. Found: MALDI-TOF MS: [M]$^+$=22,397. Anal. Found: C, 55.17; H, 8.48.

8.20 PEO-Tetra [G-2]-OH$_{16}$.

The PEO-Tetra-[G-2]-Bn$_8$ (3.35 g, 0.15 mmoles) was dissolved in 16 mL of CH$_2$Cl$_2$/MeOH (1:2) solvent mixture. The Pd/C (10%) used as catalyst (0.4 g) was added to the reaction mixture. After evacuation of the system, the reaction mixture was stirred vigorously for 15 h at room temperature under H$_2$ atmosphere. The reaction mixture was filtered through a glass filter for removing the catalyst. The product in solution was precipitated in 500 mL of diethyl ether to yield 3.09 g of a white powder (95%). IR (cm$^{-1}$, thin film from CHCl$_3$): 3462, 2883, 1734, 1107. $^1$H-NMR (300 MHz, CDCl$_3$): δ 1.07 (s, 24), 1.31 (s, 12), 3.38 (m, 20), 3.64 (bs, ca. 2100), 3.83 (s, 32), 3.87 (m, 16), 4.30 (m, 16), 4.40 (d, 8, J=11.1). $^{13}$C-NMR (400 MHz, CDCl$_3$): δ 17.10, 17.95, 46.43, 49.74, 64.34, 64.88, 67.39, 68.81, 70.56, 172.98, 174.98. Calcd.: [M]$^+$ m/z=21,726. Found: MALDI-TOF MS: [M]$^+$=21,728. Anal. Found: C, 53.54; H, 8.67.

8.21 PEO-Tetra-[G-3]-Bn$_{16}$.

The PEO-Tetra-[G-2]-OH$_{16}$ (2.93 g, 0.14 mmoles, 1.0 equiv) was dissolved in 30 mL of CH$_2$Cl$_2$. The benzylidene anhydride 2 (4.67 g, 10.96 mmoles, 80.0 equiv) and DMAP (0.13 g, 1.10 mmoles, 8.0 equiv) were added to the solution. The reaction mixture was stirred for 16 h at room temperature. 5 mL of MeOH were then added to the reaction mixture to quench the excess anhydride 2 and the whole was stirred for 8 h. The product was precipitated directly from the reaction mixture solution into 500 mL of diethyl ether. The precipitate was filtered through a glass filter to yield 3.10 g of product as a white powder (92%). IR (cm$^{-1}$, thin film from CHCl$_3$): 2885, 1741, 1126. $^1$H-NMR (400 MHz, CDCl$_3$): δ 0.92 (s, 48), 1.04 (s, 12), 1.20 (s, 24), 3.63, (bs, ca. 2100), 4.07 (m, 8), 4.18 (s, 4), 4.34 (s, 32), 4.55 (d, 32, J=11.7), 5.40 (s, 16), 7.29 (m, 48), 7.38 (m, 32). $^{13}$C-NMR (400 MHz, CDCl$_3$): δ 17.23, 17.62, 17.66, 42.52, 46.40, 46.85, 64.19, 65.11, 65.80, 70.53, 73.41, 73.48, 101.65, 126.14, 128.07, 128.79, 137.81, 171.85, 173.14. Calcd.: [M]$^+$ m/z=24,663. Found: MALDI-TOF MS: [M]$^+$=24,896. Anal. Found: C, 55.53; H, 8.18.

8.22 PEO-Tetra-[G-3]-OH$_{32}$.

The PEO-Tetra-[G-3]-Bn$_{16}$ (2.87 g, 0.12 mmoles) was dissolved in 12 mL of a 1:2 CH$_2$Cl$_2$/MeOH solvent mixture. The Pd/C (10%) used as catalyst (0.3 g) was added to the reaction mixture. The system was evacuated and the reaction mixture was stirred vigorously for 18 h at room temperature under H$_2$ atmosphere. The reaction mixture was filtered through a glass filter for removing the catalyst. The product in solution was precipitated in 500 mL of diethyl ether to yield 2.10 g of a white powder (78%). IR (cm$^{-1}$, thin film from CHCl$_3$): 3455, 2885, 1737, 1124. $^1$H-NMR (400 MHz, d$_6$-DMSO): δ 1.01 (s, 48), 1.16 (s, 24), 1.19 (s, 12), 3.51 (bs, ca. 2100), 4.14 (m, 54), 4.63 (t, 32, J=5.4)). $^{13}$C-NMR (400 MHz, d$_6$-DMSO): δ 16.68, 16.95, 17.08, 46.09, 46.30, 50.24, 63.65, 64.47, 69.77, 171.81, 171.98, 174.03. Calcd.: [M]$^+$ m/z=23,582. Found: MALDI-TOF MS: [M]$^+$=23,582. Anal. Found: C, 53.59; H, 8.44.

8.23 PEO-Tetra-[G-4]-Bn$_{32}$.

The PEO-Tetra-[G-3]-OH$_{32}$ (1.94 g, 0.08 mmoles, 1.0 equiv) was dissolved in 25 mL of CH$_2$Cl$_2$. It was followed by the addition of the benzylidene anhydride 2 (4.53 g, 10.62 mmoles, 128.0 equiv) and DMAP (0.13 g, 1.06 mmoles, 12.8 equiv) into the solution. The reaction mixture was stirred for 18 h at room temperature. 5 mL of MeOH were added to the reaction mixture and stirred for 10 h to quench the excess anhydride 2. The product was precipitated directly from the reaction mixture solution into 500 mL of diethyl ether. The precipitate was filtered through a glass filter to yield 1.73 g of product as a white powder (70%). IR (cm$^{-1}$, thin film from CHCl$_3$): 2883, 1741, 1126. $^1$H-NMR (300 MHz, CDCl$_3$): δ 0.90 (s, 96), 1.01 (s, 24), 1.14 (s, 12), 1.19 (s, 48), 3.64 (bs, ca. 2100), 3.87 (t, 8, J=5.1), 4.04 (s, 28), 4.14 (m, 22), 4.34 (dd, 64, J=15.2, 3.3), 4.54 (d, 64, J=11.4), 5.38 (s, 32), 7.29 (m, 96), 7.38 (m, 64). $^{13}$C-NMR (500 MHz, CDCl$_3$): δ 17.13, 17.61, 42.48, 46.40, 46.43, 46.77, 64.97, 65.34, 66.06, 70.27, 70.50, 73.35, 73.41, 101.58, 126.11, 128.05, 128.78, 137.79, 171.33, 171.80, 173.11. Calcd.: [M]$^+$ m/z=30,110. Found: MALDI-TOF MS: [M]$^+$=30,094; polydispersity=1.08. Anal. Found: C, 56.95; H, 8.02.

8.24 PEO-Tetra [G-4]-H$_{64}$.

The PEO-Tetra-[G-4]-Bn$_{32}$ (1.54 g, 0.05 mmoles) was dissolved in 12 mL of a 1:2 CH$_2$Cl$_2$/MeOH solvent mixture. The catalyst (Pd/C 10%, 0.2 g) was added to the reaction mixture. After evacuation of the system the reaction mixture was stirred vigorously for 18 h at room temperature under H2 atmosphere. The reaction mixture was filtered through a glass filter for removing the catalyst. The product in solution was precipitated in 500 mL of diethyl ether to yield 1.19 g of a white powder (85%). IR (cm$^{-1}$, thin film from CHCl$_3$): 3456, 2883, 1737, 1108. $^1$H-NMR (300 MHz, d$_6$-DMSO): δ 1.01 (s, 96), 1.16 (s, 48), 1.17 (s, 24), 1.21 (s, 12), 3.50 (bs, ca. 2100), 3.74 (t, 12, J=5.1), 4.14 (m, 116), 4.63 (t, 64, J=5.4). $^{13}$C-NMR (500 MHz, d$_6$-DMSO): δ 17.07, 17.38, 17.49, 17.87, 46.51, 46.53, 46.65, 49.93, 64.74, 66.21, 70.49, 172.44, 174.94. Calcd.: [M]$^+$ m/z=27,294. Found: MALDI-TOF MS: [M]$^+$=27,280, polydispersity=1.10. Anal. Found: C, 54.19; H, 8.20.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A composition of matter consisting essentially of a plurality of dendrimers, wherein said composition of matter comprises a subunit having the structure:

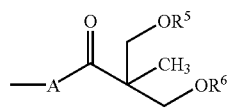

wherein said composition of matter is free of urea side products

A is a member selected from NH, S and O;

R$^5$ and R$^6$ are members independently selected from the group consisting of H, diagnostic agents, therapeutic agents, analytical agents, and moieties comprising a reactive group wherein R$^5$ and R$^6$ together with the oxygen atoms to which they are attached optionally form a structure which is a member selected from the group consisting of:

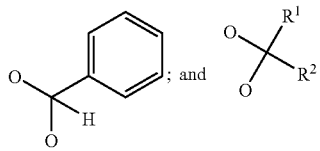

wherein
R¹ and R² are members independently selected from substituted or unsubstituted alkyl, substituted or unsubstituted heteroalkyl and substituted or unsubstituted aryl.

2. The composition of matter according to claim 1, wherein A is a component of a polymer.

3. The composition of matter according to claim 2, wherein said polymer is a member selected from the group consisting of nucleic acids, linear poly(alkylene oxides), star poly(alkylene oxides), polysaccharides, poly(amino acids) and poly(hydroxystyrene).

4. The composition of matter according to claim 3, wherein said polysaccharide is a member selected from cyclodextrin, starch, hydroxyethyl starch and dextran.

5. The composition of matter according to claim 3, wherein said poly(amino acid) comprises lysine, tyrosine, serine, cysteine, arginine, histidine and combinations thereof.

6. The composition of matter according to claim 2, wherein said polymer is a synthetic organic polymer with pendant NH groups, OH groups, SH groups and combinations thereof.

7. The composition of matter according to claim 6, wherein said synthetic organic polymer is a member selected from poly(vinylphenol), poly(hydroxymethacrylate), poly(N-2-hydroxypropylmethacrylamide), poly(diallylamine), poly(lactic acid) and poly(hydroxymethylcaprolactone), poly(4-hydroxyethylcaprolactone).

8. The composition of matter according to claim 1, wherein at least one of said $R^5$ and $R^6$ is a therapeutic agent, and wherein said therapeutic agent is a member selected from the group consisting of antiproliferative agents, proteins, anti-cancer chemotherapeutic agents, antibiotics, antivirals, and antiparasitics.

9. The composition of matter according to claim 1, wherein at least one of said $R^5$ and $R^6$ is a diagnostic agent, and wherein said diagnostic agent is a member selected from MRI contrast agents, X-ray contrast agents, CT contrast agents, PET contrast agents, ultrasonography contrast agents, fluorescent agents, chromophoric agents and radioisotopes.

10. The composition of matter according to claim 1, wherein said subunit repeats from 2 to 100 times.

11. The composition of matter according to claim 10, wherein said subunit repeats from 4 to 50 times.

12. The composition of matter according to claim 11, wherein said subunit repeats from 8 to 24 times.

13. The composition of matter according to claim 1, wherein at least one of $R^5$ and $R^6$ has the structure:

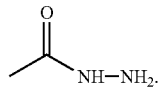

14. The composition of matter according to claim 1, wherein at least one of $R^5$ and $R^6$ has the structure:

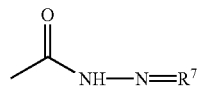

wherein, $R^7$ is a member selected from the group consisting of diagnostic agents, therapeutic agents and analytical agents.

15. The composition of matter according to claim 14, wherein $R^7$ is a doxorubicin derivative.

16. A pharmaceutical formulation comprising the composition of matter according to claim 1 and a pharmaceutically acceptable carrier.

17. A composition of matter consisting essentially of a plurality of dendrimers, wherein said composition of matter comprises a subunit having the structure:

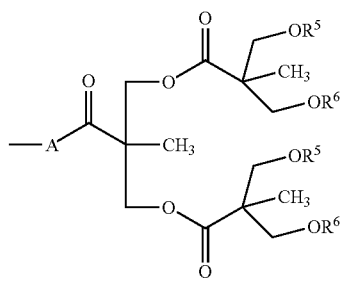

wherein
said composition of matter is free of urea side products
A is a member selected from NH, S and O;
$R^5$ and $R^6$ are members independently selected from the group consisting of H, diagnostic agents, therapeutic agents, analytical agents, and moieties comprising a reactive group
wherein $R^5$ and $R^6$ together with the oxygen atoms to which they are attached optionally form a structure which is a member selected from the group consisting of:

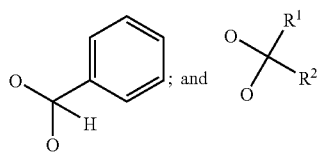

wherein
R¹ and R² are members independently selected from substituted or unsubstituted alkyl, substituted or unsubstituted heteroalkyl and substituted or unsubstituted aryl.

18. A composition of matter consisting essentially of a plurality of dendrimers, wherein said composition of matter comprises a subunit having the structure:

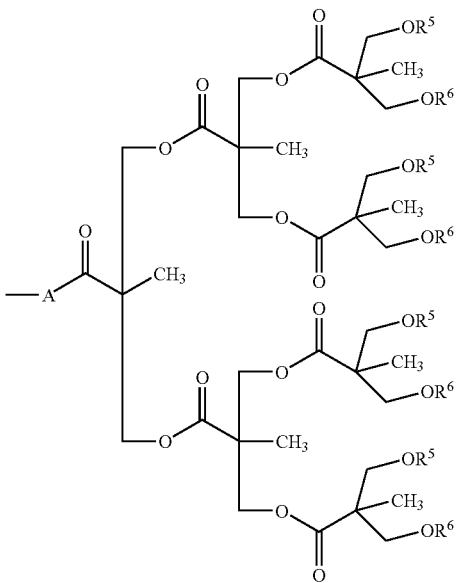

wherein
said composition of matter is free of urea side products
A is a member selected from NH, S and O;
R⁵ and R⁶ are members independently selected from the group consisting of H, diagnostic agents, therapeutic agents, analytical agents, and moieties comprising a reactive group
wherein R⁵ and R⁶ together with the oxygen atoms to which they are attached optionally form a structure which is a member selected from the group consisting of:

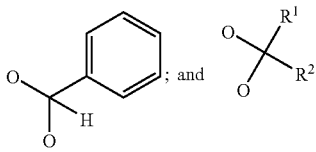

wherein
R¹ and R² are members independently selected from substituted or unsubstituted alkyl, substituted or unsubstituted heteroalkyl and substituted or unsubstituted aryl.

19. The composition of matter of claim 1, wherein said dendrimers are produced by a process comprising:
(a) forming a reaction mixture by contacting a core moiety comprising A with an acylating group in an organic solvent, said acylating group having the structure:

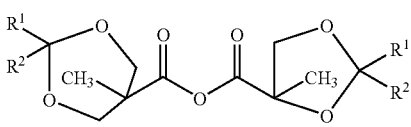

thereby acylating A, forming said dendrimer; and (b) extracting said reaction mixture with an aqueous solution, thereby removing impurities.

20. The composition of matter according to claim 19, wherein A is a component of a polymer.

21. The composition of matter according to claim 20, wherein said polymer is a member selected from the group consisting of nucleic acids, linear poly(alkylene oxides), star poly(alkylene oxides), polysaccharides, poly(amino acids) and poly(hydroxystyrene).

22. The composition of matter according to claim 19, wherein at least one of said R⁵ and R⁶ is a therapeutic agent, and wherein said therapeutic agent is a member selected from the group consisting of antiproliferative agents, proteins, anti-cancer chemotherapeutic agents, antibiotics, antivirals, and antiparasitics.

23. The composition of matter according to claim 19, wherein at least one of said R⁵ and R⁶ is a diagnostic agent, and wherein said diagnostic agent is a member selected from MRI contrast agents, X-ray contrast agents, CT contrast agents, PET contrast agents, ultrasonography contrast agents, fluorescent agents, chromophoric agents and radioisotopes.

24. The composition of matter according to claim 19, wherein said subunit repeats from 2 to 100 times.

25. The composition of matter according to claim 24, wherein said subunit repeats from 4 to 50 times.

26. The composition of matter according to claim 25, wherein said subunit repeats from 8 to 24 times.

27. The composition of matter according to claim 19, wherein at least one of R⁵ and R⁶ has the structure:

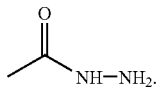

28. The composition of matter according to claim 19, wherein at least one of R⁵ and R⁶ has the structure:

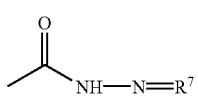

wherein, R⁷ is a member selected from the group consisting of diagnostic agents, therapeutic agents and analytical agents.

29. The composition of matter according to claim 28, wherein R⁷ is a doxorubicin derivative.

30. A pharmaceutical formulation comprising the composition of matter according to claim 19 and a pharmaceutically acceptable carrier.

31. The composition of matter according to claim 19, produced by a process which further comprises:
(c) removing said diol protecting group, thereby forming a first generation dendrimer comprising a subunit having the structure:

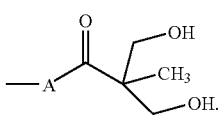

32. A composition of matter consisting essentially of a plurality of dendrimers, wherein said composition of matter comprises a subunit having the structure:

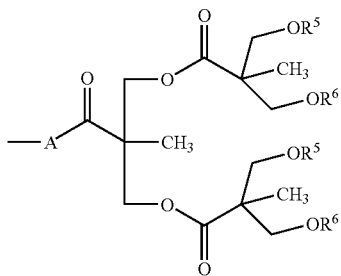

wherein
said composition of matter is free of urea side products
A is a member selected from NH, S and O;
$R^5$ and $R^6$ are members independently selected from the group consisting of H, diagnostic agents, therapeutic agents, analytical agents, and moieties comprising a reactive group
wherein $R^5$ and $R^6$ together with the oxygen atoms to which they are attached optionally form a structure which is a member selected from the group consisting of:

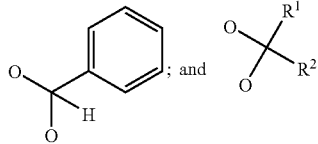

wherein
$R^1$ and $R^2$ are members independently selected from substituted or unsubstituted alkyl, substituted or unsubstituted heteroalkyl and substituted or unsubstituted aryl;
wherein said dendrimers are produced by a process comprising:
(a) contacting said first generation dendrimer according to claim 31 with an acylating group having the structure:

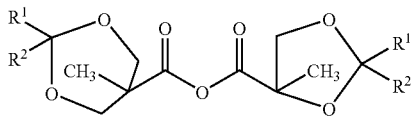

thereby acylating A, forming said dendrimer; and
(b) extracting said reaction mixture with an aqueous solution, thereby removing impurities.

33. The composition of matter according to claim 32, produced by a process which further comprises:
(c) removing said diol protecting group, thereby forming a second generation dendrimer comprising a subunit having the structure:

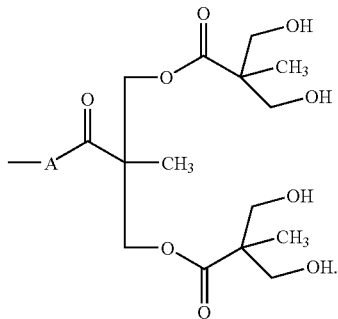

* * * * *